US011427837B2

(12) United States Patent
Corn et al.

(10) Patent No.: US 11,427,837 B2
(45) Date of Patent: Aug. 30, 2022

(54) COMPOSITIONS AND METHODS FOR ENHANCED GENOME EDITING

(71) Applicant: The Regents of the University of California, Oakland, CA (US)

(72) Inventors: Jacob Corn, Berkeley, CA (US); Christopher D. Richardson, San Francisco, CA (US); Graham Jordan Ray, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1084 days.

(21) Appl. No.: 16/067,750

(22) PCT Filed: Jan. 11, 2017

(86) PCT No.: PCT/US2017/012980
§ 371 (c)(1),
(2) Date: Jul. 2, 2018

(87) PCT Pub. No.: WO2017/123609
PCT Pub. Date: Jul. 20, 2017

(65) Prior Publication Data

US 2019/0010519 A1 Jan. 10, 2019

Related U.S. Application Data

(60) Provisional application No. 62/277,802, filed on Jan. 12, 2016.

(51) Int. Cl.

| | |
|---|---|
| ***C12N 9/22*** | (2006.01) |
| ***C12N 15/85*** | (2006.01) |
| ***C12N 15/11*** | (2006.01) |
| ***C12N 15/90*** | (2006.01) |
| ***A01K 67/027*** | (2006.01) |

(52) U.S. Cl.
CPC .......... *C12N 15/907* (2013.01); *A01K 67/027* (2013.01); *A01K 67/0271* (2013.01); *C12N 9/22* (2013.01); *C12N 15/11* (2013.01); *C12N 15/85* (2013.01); *A01K 2207/12* (2013.01); *A01K 2227/105* (2013.01); *A01K 2267/0306* (2013.01); *C12N 2310/20* (2017.05); *C12N 2800/80* (2013.01)

(58) Field of Classification Search
CPC .... C12N 15/907; C12N 2310/20; C12N 9/22; C12N 15/11; C12N 2800/80; C12N 15/85; A01K 67/027; A01K 67/0271
See application file for complete search history.

(56) References Cited

U.S. PATENT DOCUMENTS

| | | | | |
|---|---|---|---|---|
| 9,790,490 B2 * | 10/2017 | Zhang | C12N 15/10 | |
| 2011/0287545 A1 | 11/2011 | Cost et al. | | |
| 2014/0068797 A1 * | 3/2014 | Doudna | A01K 67/027 | 800/18 |
| 2014/0173783 A1 * | 6/2014 | Ainley | C12N 9/1241 | 800/320.1 |
| 2015/0071901 A1 * | 3/2015 | Liu | C12N 9/96 | 435/325 |
| 2015/0071903 A1 * | 3/2015 | Liu | C07K 14/463 | 424/94.3 |
| 2015/0079680 A1 | 3/2015 | Bradley et al. | | |
| 2015/0132269 A1 | 5/2015 | Orkin et al. | | |

FOREIGN PATENT DOCUMENTS

| | | | |
|---|---|---|---|
| WO | WO 2014/204726 | 12/2014 | |
| WO | WO-2015168404 A1 * | 11/2015 | C12N 9/22 |
| WO | WO-2016094867 A1 * | 6/2016 | A01K 67/0275 |
| WO | WO-2014204726 A9 * | 10/2016 | C12N 15/1082 |

OTHER PUBLICATIONS

Laughery et al., New vectors for simple and streamlined CRISPR-Cas9 genome editing in Saccharomyces cerevisiae. Yeast 2015; 32: 711-720 (Year: 2015).*
ThermoFisher UltraPure™ Salmon Sperm DNA Solution Cat#: 15632011 [Retrieved on Nov. 17, 2021] (Year: 2021).*
Miura et al., CRISPR/Cas9-based generation of knockdown mice by intronic insertion of artificial microRNA using longer single-stranded DNA. Scientific Reports (2015) 5:12799 (Year: 2015).*
Robert et al., Pharmacological inhibition of DNA-PK stimulates Cas9-mediated genome editing. Genome Medicine (2015) 7:93 (Year: 2015).*
Bassett, et al.; "A Genome-Wide CRISPR Library for High-Throughput Genetic Screening in *Drosophila* Cells"; Journal of Genetics and Genomics; vol. 42, pp. 301-309 (2015).
Kime, et al.; "Efficient CRISPR/Cas9-Based Genome Engineering in Human Pluripotent Stem Cells"; Current Protocols in Human Genetics; vol. 88, Unit 21.4, pp. 1-31 (Jan. 1, 2016).
Ran, et al.; "Genome engineering using the CRISPR-Cas9 system"; Nat. Protoc.; vol. 8, No. 11, pp. 2281-2308 (Nov. 2013).

(Continued)

*Primary Examiner* — Neil P Hammell
*Assistant Examiner* — Catherine Konopka
(74) *Attorney, Agent, or Firm* — Bozicevic Field & Francis, LLP; Paula A. Borden

(57) ABSTRACT

The present disclosure provides methods and compositions for enhanced editing of genomic DNA. For example, in some embodiments, a subject method is a method of editing genomic DNA of a eukaryotic cell and the method includes introducing into a eukaryotic cell a composition comprising: (a) a linearized non-homologous DNA composition and (b) a genome targeting composition (which includes a genome editing endonuclease, or a nucleic acid encoding the genome editing endonuclease). In some cases in which the genome editing endonuclease is a CRISPR/Cas endonuclease, the genome targeting composition can also include a corresponding CRISPR/Cas guide RNA.

13 Claims, 39 Drawing Sheets

Specification includes a Sequence Listing.

(56) References Cited

OTHER PUBLICATIONS

Zetsche, et al.; "Cpf1 is a single RNA-guided endonuclease of a Class 2 CRISPR-Cas system"; Cell; vol. 163, No. 3, pp. 759-771 (Oct. 22, 2015).

* cited by examiner

| | WT | Het | Hom |
|---|---|---|---|
| RNP | 40 | 60 | 0 |
| RNP+N | 0 | 40 | 60 |

Percent of Clones

| Site | N-Oligo - | N-Oligo + | Coordinate | Sequence |
|---|---|---|---|---|
| **EMX1** | **21.4** | **55.3** | Chr2:72933982 | CGATGTCACCTCCAATGACTAGG |
| **OT1** | 3.2 N/S | 2.3 N/S | Chr3:162729293 | TAATGTCACCCCCAATGACTTAG |
| **OT2** | 2.1 N/S | 1.5 N/S | Chr2:124751516 | ACAAGTCACTTCCAATGACTTAG |
| **OT3** | 1.1 N/S | 2.5 N/S | Chr11:84360095 | CGATTTCTCCTCCAATGATTCAG |
| **OT4** | 1.2 N/S | 1.6 N/S | Chr2:230900416 | TAATATTACCTCCAATGACTCGG |

HEK293 RNP Only

| Clone | WT | Deletions | Insertions |
|---|---|---|---|
| 2 | (19) | | |
| 3 | (16) | | |
| 4 | (11) | | 9bp/2bp template indel (3) |
| 5 | (19) | | |
| 6 | (19) | | |
| 7 | (18) | 216bp del (1) | |
| 8 | (12) | 21bp del (1), 295bp del (1), 433bp del (1) | |
| 9 | (7) | 3bp del (6) | |
| 10 | (15) | 7bp del (1), 21bp del (1) | |
| 11 | (16) | | |

Fig. 6 (Cont. 1)
HEK293 RNP+N-oligo
| Clone | WT | Deletions | Insertions |
|---|---|---|---|
| 1 | (1) | 3bp del (3), 5bp del (1) | 3bp ins (2), 20bp unknown ins (10) |
| 2 | | 15bp del (11) | 5bp/26bp indel (5) |
| 4 | | 7bp del (20) | |
| 5 | (2) | 5bp del (7) | 11bp/5bp indel (2), 339bp/5bp template/N-oligo indel (8) |
| 6 | | 10bp del (7) | 251bp template ins (8) |
| 7 | | | 86bp/14bp N-oligo indel (10) 20bp/1bp indel (8) |
| 8 | | 8bp del (2) | 7bp ins (10) |
| 9 | (13) | | 10bp/4bp indel (5) |
| 10 | | 19bp del (7) | 119bp template ins (7) |
| 11 | (1) | 16bp del (6) | 82bp/18bp N-oligo indel (8), 55bp/20bp N-oligo indel (1) |
HEK293 Clonal Indel Percentage
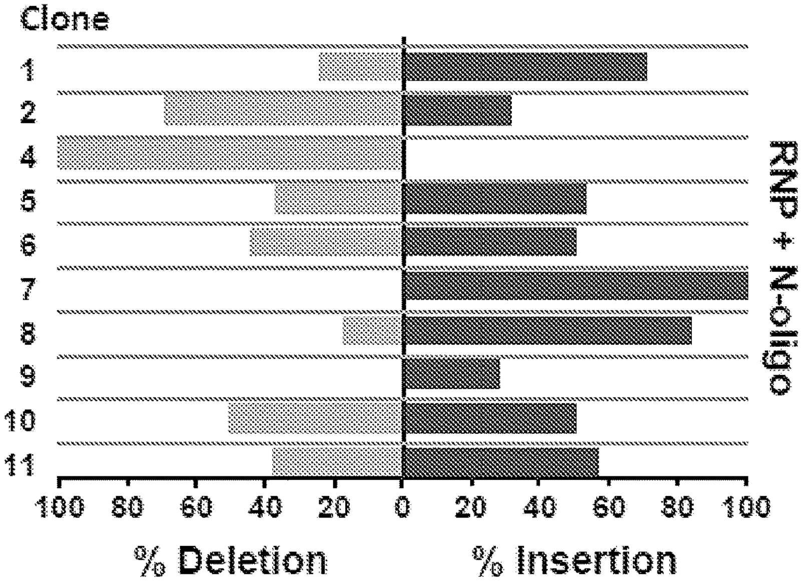

Fig. 6 (Cont. 2)

| | Treatment | WT | Deletions | Insertions |
|---|---|---|---|---|
| U2OS | RNP | (56) | 186bp del (1) | 5bp/71bp indel (1), 20bp/3bp indel (1) |
| U2OS | RNP+ N-oligo | (9) | 1-10bp del (8), 20-60bp del (5) | 8bp ins (1) |

Fig. 10A
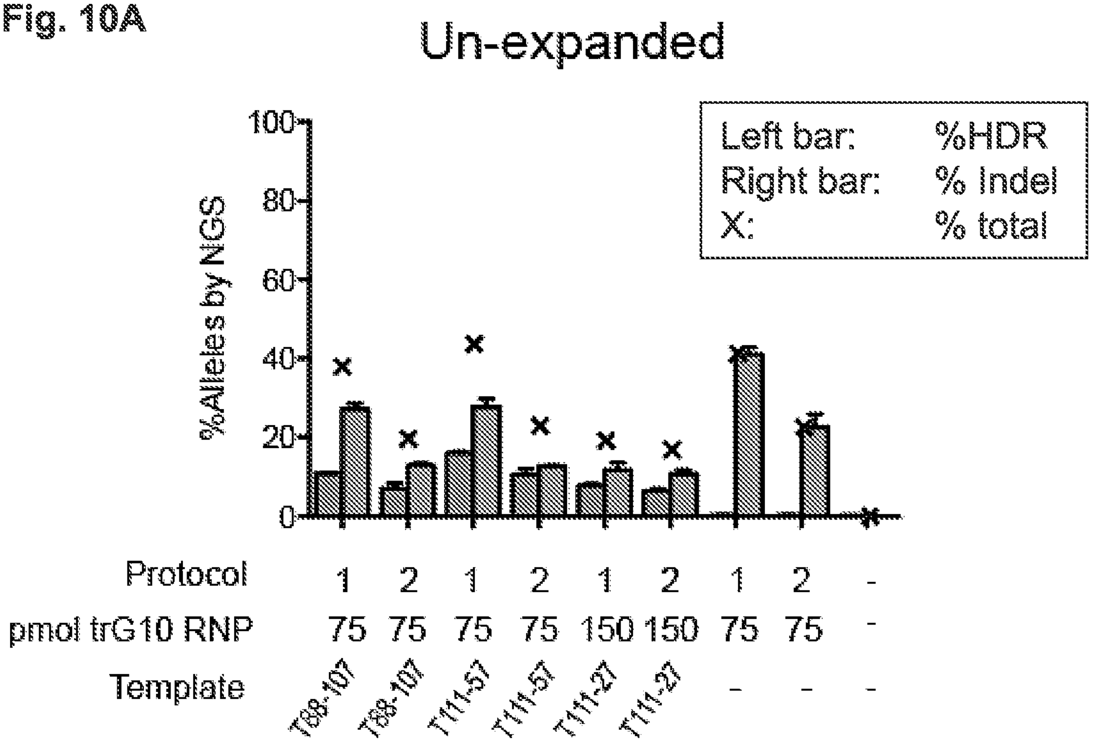
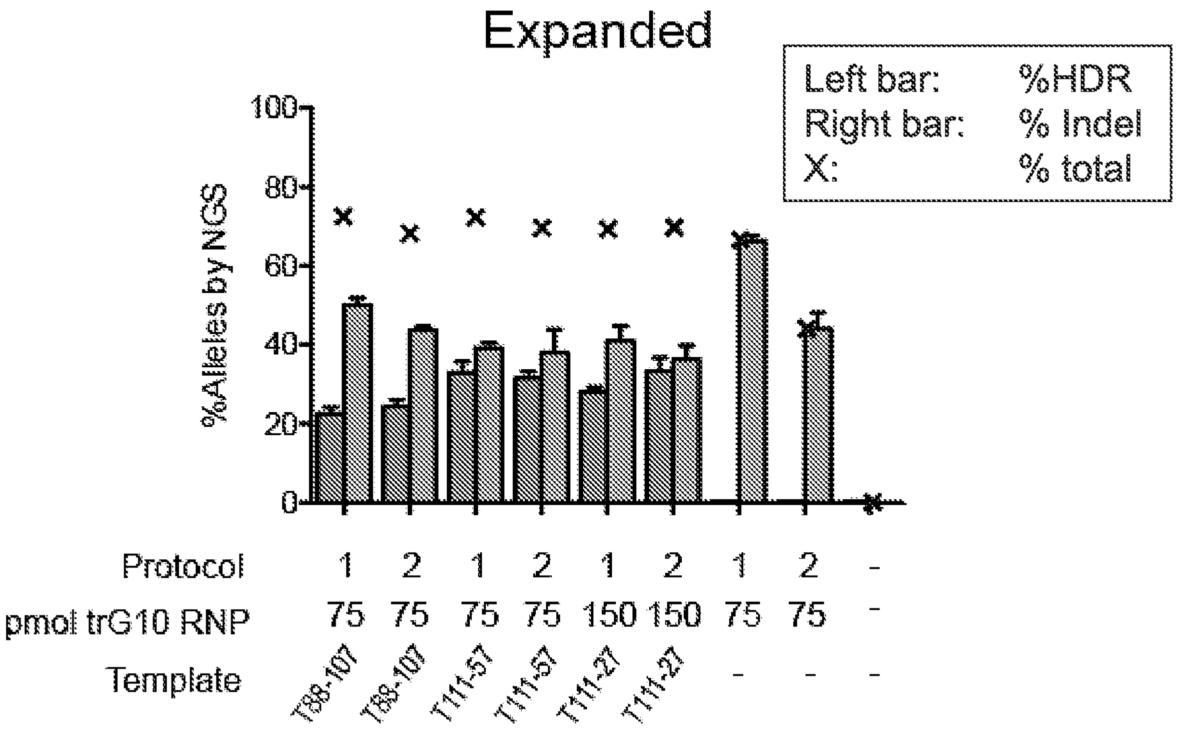

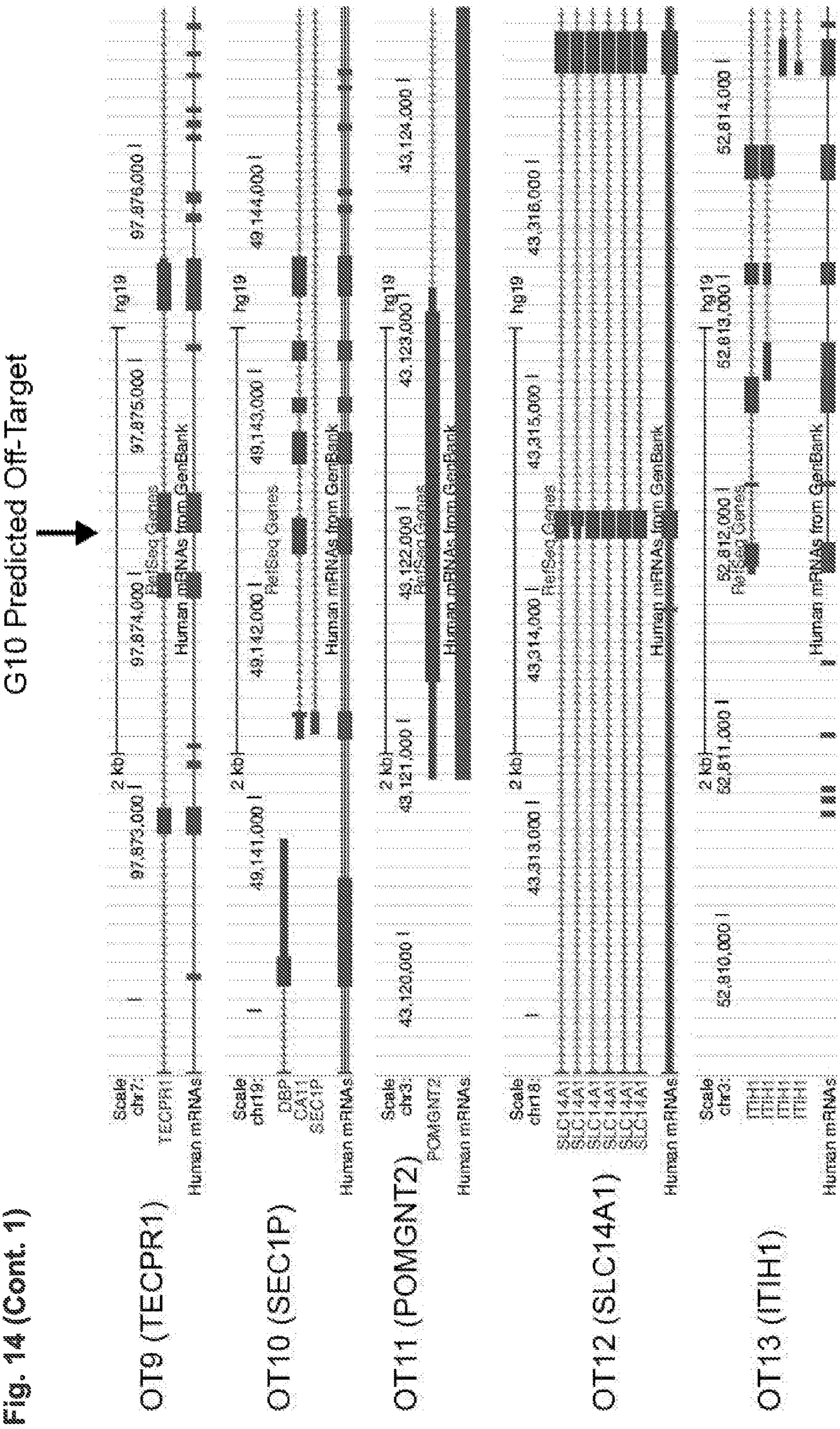
Fig. 14 (Cont. 1)

Fig. 14 (Cont. 2)
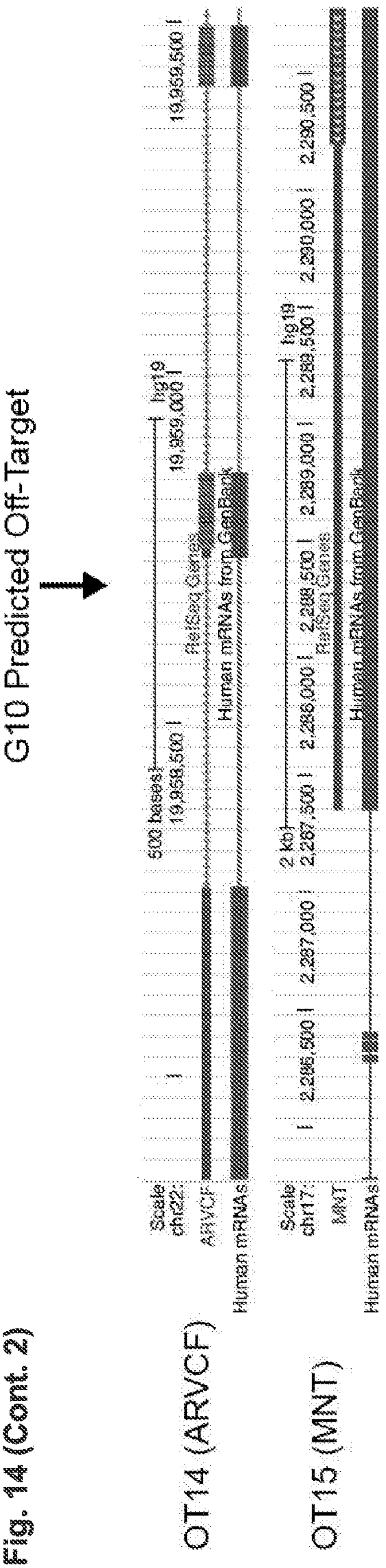

Fig. 19

| | N = 96 colonies | | | | | |
|---|---|---|---|---|---|---|
| | %WT | %Indel | %HDR | | | |
| All Alleles | 46 | 33 | 21 | | | |
| Clones with one allele | %WT/_ | %Indel/_ | %HDR/_ | | | |
| Actual | 60 | 48 | 32 | | | |
| Predicted | 71 | 55 | 37 | | | |
| Clones by genotype | % WT /WT | % WT /Indel | %WT /HDR | %Indel /Indel | %Indel /HDR | %HDR /HDR |
| Actual | 32 | 18 | 10 | 18 | 13 | 9.4 |
| Predicted | 21 | 30 | 19 | 11 | 14 | 4.3 |

Fig. 20

I. K562 Cells

| Chr | Location | Gene | Type | Reference | Mutation | %Reads[1] (edited) | % Reads[1] (unedited) |
|---|---|---|---|---|---|---|---|
| 22 | 29130813 | CHEK2 (intron) | Deletion | GAA | G | 9.56 | 5.96 |
| 7 | 148543731 | EZH2 (intron) | Insertion | C | CT | 0.67 | 0.02 |
| 7 | 148543732 | EZH2 (intron) | Insertion | A | AACAATGAACAAT TTCTCCTTTCCTCTC CTTCATTTTT | 0.67 | 0.21 |
| 10 | 43601785 | RET (intron) | Insertion | A | AGGTGTCCCCGGG GAGCAGCGTGCTT GTGTACCGCCTCAC CAGCTCCCCTGATG CAGGTACCACG | 0.74 | 0.18 |
| 10 | 72357821 | PRF1 | Insertion | C | CTGTCTCTTATACA CATCTCCGAG | 0.55 | 0.11 |
| 10 | 104353831 | SUFU (Intron) | Insertion | T | TGAGTGAGGAAAA CCCACTCAAGACAT ACTTGCAGGTGTG GATCGATCTC | 0.76 | 0.33 |
| 17 | 25541278 | Intergenic | Insertion | A | AGTGT | 2.2 | 2.32 |
| 17 | 29557005 | NF1 (Intron) | Insertion | C | CATTTCAG | 1.22 | 0 |

II. HSPCs

No indel mutations detected.

[1]Percent of reads is percent of unique sequencing reads, based on read/insert length.

Fig. 21

| | Week 16 Bone Marrow (NGS) | | | Week 16 Cellular Prevalence Estimate | | |
|---|---|---|---|---|---|---|
| **Mouse** | %HDR (p) | %indel (q) | %Unedited (r) | %HDR+ (p_) | %Indel+ (q_) | %Unedited (r_) |
| **1** | 0.91 | 57.20 | 41.88 | 1.81 | 81.68 | 66.23 |
| **2** | 6.20 | 51.07 | 42.73 | 12.02 | 76.06 | 67.20 |
| **3** | 1.60 | 45.04 | 53.36 | 3.17 | 69.80 | 78.24 |
| **4** | 1.46 | 43.05 | 55.49 | 2.90 | 67.57 | 80.19 |
| **5** | 1.40 | 42.08 | 56.52 | 2.78 | 66.45 | 81.09 |
| **6** | 1.68 | 43.91 | 54.41 | 3.33 | 68.54 | 79.22 |
| **7** | 2.88 | 41.31 | 55.81 | 5.68 | 65.55 | 80.47 |
| **Mean** | 2.30 | 46.24 | 51.46 | 4.53 | 70.81 | 76.09 |
| **SD** | 1.82 | 5.81 | 6.34 | 3.51 | 5.90 | 6.48 |

COMPOSITIONS AND METHODS FOR ENHANCED GENOME EDITING

CROSS-REFERENCE

This application is a national stage application under 35 U.S.C. § 371 of PCT/US2017/012980, filed Jan. 11, 2017, which claims the benefit of U.S. Provisional Patent Application No. 62/277,802, filed Jan. 12, 2016, which applications are incorporated herein by reference in their entirety.

INCORPORATION BY REFERENCE OF SEQUENCE LISTING PROVIDED AS A TEXT FILE

A Sequence Listing is provided herewith as a text file, "BERK-311WO_Seq_List_ST25.txt" created on Jan. 11, 2017 and having a size of 7,892 KB. The contents of the text file are incorporated by reference herein in their entirety.

INTRODUCTION

Disruption of mammalian genes holds great promise for fundamental discovery, treatment of genetic diseases, and prophylactic treatment (e.g., of HIV). Gene knockouts can be generated using a genome editing endonuclease (e.g., a zinc finger nuclease (ZFN), a transcription activator-like effector nuclease (TALEN), a CRISPR/Cas protein:guide RNA, and the like) to introduce a site specific double strand break (DSB) within a locus (e.g., gene) of interest. Clones can be screened for those in which one or more alleles have been repaired in an error-prone fashion that disrupts the open reading frame. The efficiency of this process is limited by the number of clones screened to find the desired mutation, which is itself a product of the frequency of genome cutting as well as the frequency of desired (i.e., disrupting) repair events.

There is a need in the art for methods and compositions for increasing the frequency of disrupting mutations (e.g., indels) that can be produced when using targeted genome editing nucleases.

SUMMARY

The present disclosure provides methods and compositions for enhanced editing of genomic DNA. For example, in some embodiments, a subject method is a method of editing genomic DNA of a eukaryotic cell and the method includes introducing into a eukaryotic cell a composition comprising a linearized non-homologous DNA composition and a genome targeting composition (which includes a genome editing endonuclease, or a nucleic acid encoding the genome editing endonuclease).

After a site-specific double strand break (DSB) or single strand break (SSB) within a double-stranded DNA (dsDNA) has been detected by a cell, the cell's DNA repair machinery repairs the lesion either by non-homologous end joining (NHEJ) or homology-directed recombination (HDR). NHEJ can cause an error compared to the original DNA sequence, or can be error-free. Thus, when using a genome editing endonuclease (e.g., a zinc finger nuclease, a TALEN, a class 2 CRISPR/Cas endonuclease, etc.) to induce insertion and deletion mutations (indels) in the genomic DNA of a target cell population, some of the cells repair the break without error, and no indels are therefore detected in some cells even when cleavage occurred at the targeted site.

The linearized non-homologous DNA composition of the subject methods and compositions increases the frequency of the generation of indels in targeted genomic DNA when the genomic DNA is cleaved with a genome editing endonuclease (e.g., a zinc finger nuclease, a TALEN, a class 2 CRISPR/Cas endonuclease, etc.). The inventors have discovered that including a linear non-homologous DNA composition increases the likelihood of error-prone end-joining. In other words, the presence of a linear non-homologous DNA composition decreases the rate of error-free NHEJ, and thereby increases the rate of insertions and deletions (indels) that are produced in the target DNA. Thus, in cases where one desires to edit the genomic DNA of a cell (e.g., in cases in which one wishes to generate an indel at a target position within a target genome), the inclusion of a subject linear non-homologous DNA composition can substantially increase the likelihood of success.

Provided are methods of editing a genomic DNA of a eukaryotic cell, where the method includes introducing into the eukaryotic cell a composition including: (a) a genome targeting composition including a genome editing endonuclease, or a nucleic acid encoding the genome editing endonuclease, wherein the genome editing endonuclease cleaves within a desired target sequence of the genomic DNA of the cell; and (b) a linear non-homologous DNA composition including linear DNA in an amount effective to enhance the frequency of insertions and/or deletions (indels) within the genomic DNA, where the method results in modification of the genomic DNA. In some cases, the modification of the genomic DNA is an insertion of sequence into the genomic DNA and/or a deletion of sequence from the genomic DNA.

In some cases, the genome targeting composition includes a zinc finger nuclease or a TAL-effector DNA binding domain-nuclease fusion protein (TALEN). In some cases, the genome targeting composition includes a nucleic acid encoding a zinc finger nuclease or a TAL-effector DNA binding domain-nuclease fusion protein (TALEN). In some cases, the genome targeting composition includes a ribonucleoprotein (RNP) complex including a class 2 CRISPR/Cas endonuclease complexed with a corresponding CRISPR/Cas guide RNA that hybridizes to a target sequence within the genomic DNA of the cell. In some cases, the genome targeting composition includes (i) a nucleic acid encoding a class 2 CRISPR/Cas endonuclease, and (ii) a corresponding CRISPR/Cas guide RNA, or a nucleic acid encoding the corresponding CRISPR/Cas guide RNA, wherein the CRISPR/Cas guide RNA hybridizes to a target sequence within the genomic DNA of the cell. In some cases, the class 2 CRISPR/Cas endonuclease is a type II CRISPR/Cas endonuclease. In some cases, the class 2 CRISPR/Cas endonuclease is a Cas9 polypeptide and the corresponding CRISPR/Cas guide RNA is a Cas9 guide RNA. In some cases, the class 2 CRISPR/Cas endonuclease is a type V or type VI CRISPR/Cas endonuclease. In some cases, the class 2 CRISPR/Cas polypeptide is a Cpf1 polypeptide, a C2c1 polypeptide, a C2c3 polypeptide, or a C2c2 polypeptide.

In some cases, the linearized non-homologous DNA composition includes single stranded DNA. In some cases, the linearized non-homologous DNA composition comprises double stranded DNA. In some cases, the linearized non-homologous DNA composition includes one or more of: sheared salmon sperm DNA, single stranded oligonucleotides, double stranded plasmid DNA, and a combination thereof. In some cases, the linearized non-homologous DNA composition is a homogenous DNA composition. In some cases, the linearized non-homologous DNA composition is a heterogeneous DNA composition. In some cases, modification of the genomic DNA is homozygous modification. In some cases, the introducing includes nucleofection.

Provided are methods of editing genomic DNA of a eukaryotic cell, where the method includes introducing into the eukaryotic cell a composition including: (a) a linear non-homologous DNA composition including linear DNA in an amount effective to enhance frequency of insertions and/or deletions (indels) within the genomic DNA; and (b) a ribonucleoprotein (RNP) complex comprising a class 2 CRISPR/Cas endonuclease complexed with a corresponding CRISPR/Cas guide RNA that hybridizes to a target sequence within the genomic DNA of the cell, where the class 2 CRISPR/Cas endonuclease cleaves the genomic DNA, resulting in editing of the genomic DNA.

In some cases, the class 2 CRISPR/Cas endonuclease is a type II CRISPR/Cas endonuclease. In some cases, the class 2 CRISPR/Cas endonuclease is a Cas9 polypeptide and the corresponding CRISPR/Cas guide RNA is a Cas9 guide RNA. In some cases, the Cas9 guide RNA is a single guide RNA (sgRNA). In some cases, the class 2 CRISPR/Cas endonuclease is a type V or type VI CRISPR/Cas endonuclease. In some cases, the class 2 CRISPR/Cas polypeptide is a Cpf1 polypeptide, a C2c1 polypeptide, a C2c3 polypeptide, or a C2c2 polypeptide. In some cases, the linearized non-homologous DNA composition includes single stranded DNA. In some cases, the linearized non-homologous DNA composition includes double stranded DNA. In some cases, the linearized non-homologous DNA composition includes one or more of: sheared salmon sperm DNA, single stranded oligonucleotides, double stranded plasmid DNA, and a combination thereof. In some cases, the linearized non-homologous DNA composition is a homogenous DNA composition. In some cases, the linearized non-homologous DNA composition is a heterogeneous DNA composition. In some cases, introducing includes nucleofection. In some cases, the method results in a deletion of genomic DNA.

Provided are compositions including: (a) a linear non-homologous DNA composition; and (b) a genome targeting composition that includes a genome editing endonuclease, or a nucleic acid encoding the genome editing endonuclease. In some cases, the genome targeting composition includes a zinc finger nuclease, a nucleic acid encoding a zinc finger nuclease, a TAL endonuclease, or a nucleic acid encoding a TAL endonuclease. In some cases, the genome targeting composition includes a ribonucleoprotein (RNP) complex comprising a class 2 CRISPR/Cas endonuclease complexed with a corresponding CRISPR/Cas guide RNA that has complementarity to a target sequence within a genomic DNA of a eukaryotic cell. In some cases, the genome targeting composition includes a class 2 CRISPR/Cas endonuclease, or a nucleic acid encoding the class 2 CRISPR/Cas endonuclease. In some cases, the genome targeting composition further includes: (i) a corresponding CRISPR/Cas guide RNA that has complementarity to a target sequence within a genomic DNA of a eukaryotic cell, or (ii) a nucleic acid encoding the corresponding CRISPR/Cas guide RNA. In some cases, the class 2 CRISPR/Cas endonuclease is a type II CRISPR/Cas endonuclease. In some cases, the class 2 CRISPR/Cas endonuclease is a Cas9 polypeptide and the corresponding CRISPR/Cas guide RNA is a Cas9 guide RNA. In some cases, the class 2 CRISPR/Cas endonuclease is a type V or type VI CRISPR/Cas endonuclease. In some cases, the class 2 CRISPR/Cas polypeptide is a Cpf1 polypeptide, a C2c1 polypeptide, a C2c3 polypeptide, or a C2c2 polypeptide. In some cases, the linearized non-homologous DNA composition comprises single stranded DNA. In some cases, the linearized non-homologous DNA composition comprises double stranded DNA. In some cases, the linearized non-homologous DNA composition includes one or more of: sheared salmon sperm DNA, single stranded oligonucleotides, double stranded plasmid DNA, and a combination thereof. In some cases, the linearized non-homologous DNA composition is a homogenous DNA composition. In some cases, the linearized non-homologous DNA composition is a heterogeneous DNA composition.

BRIEF DESCRIPTION OF THE DRAWINGS

FIG. 10A-10C depict data related to editing of wild-type human CD34+ HSPCs by the Cas9 RNP.

FIG. 19 depicts a table showing the zygosity of clonal colonies of $CD34^+$ HSPCs edited with the trG10 RNP.

FIG. 20 depicts a table of indel mutations at cancer-associated genes in K562 cells and HSPCs edited with the trG10 RNP, compared to unedited cells. Chr. 7, Ref A mutation (SEQ ID NO: 1174); Chr. 10, Ref A mutation (SEQ ID NO: 1175); Chr. 10, Ref C mutation (SEQ ID NO: 1176); Chr. 10, Ref T mutation (SEQ ID NO: 1177).

FIG. 21 depicts a table of estimates of cellular editing in mice engrafted with edited HSPCs, from measurement of allelic editing in bone marrow by NGS, 16 weeks post-injection.

DEFINITIONS

Figure 1A:
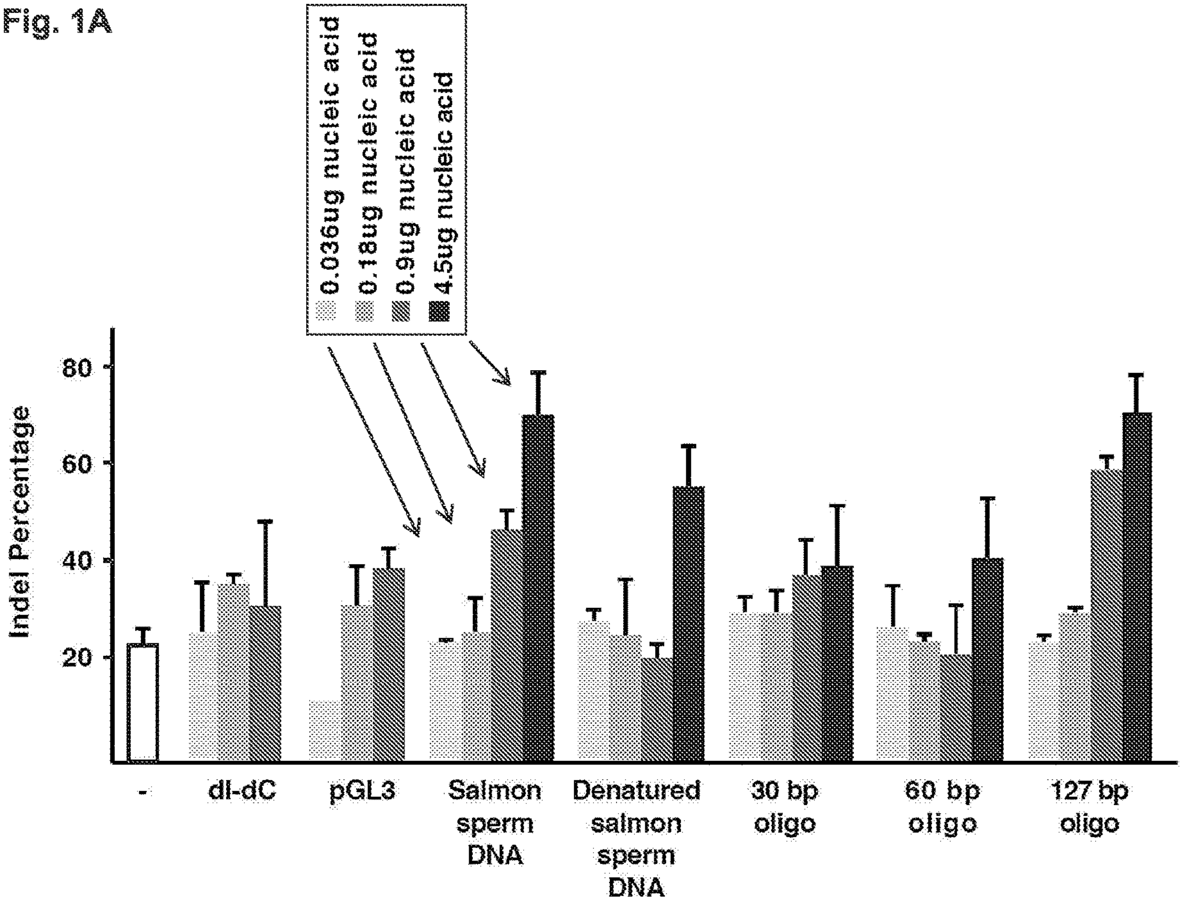
FIG. 1A-1C depict data related to the effect of linear non-homologous DNA on gene disruption in multiple cell types.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with a guide RNA, etc.): guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) (e.g., of a protein-binding segment (dsRNA duplex) of a guide RNA molecule; of a target nucleic acid base pairing with a guide RNA, etc.) is considered complementary to both a uracil (U) and to an adenine (A). For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). Temperature, wash solution salt concentration, and other conditions may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a bulge, a loop structure or hairpin structure, etc.). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656), the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489), and the like.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a Cas9 protein/guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein (and therefore the DNA and the mRNA both encode the protein), or a DNA polynucleotide may encode an RNA that is not translated into protein (e.g. tRNA, rRNA, microRNA (miRNA), a "non-coding" RNA (ncRNA), a guide RNA, etc.).

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., Cas9 polypeptide, or Cas9 polypeptide) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

The term "chimeric" as used herein as applied to a nucleic acid or polypeptide refers to two components that are defined by structures derived from different sources. For example, where "chimeric" is used in the context of a chimeric polypeptide (e.g., a chimeric Cas9 protein), the chimeric polypeptide includes amino acid sequences that are derived from different polypeptides. A chimeric polypeptide may comprise either modified or naturally-occurring polypeptide sequences (e.g., a first amino acid sequence from a modified or unmodified Cas9 protein; and a second amino acid sequence, e.g., a sequence from another species of Cas9, a sequence from a protein other than a Cas9 protein, etc.). Similarly, "chimeric" in the context of a polynucleotide encoding a chimeric polypeptide includes nucleotide sequences derived from different coding regions (e.g., a first nucleotide sequence encoding a modified or unmodified Cas9 protein; and a second nucleotide sequence encoding a polypeptide other than a Cas9 protein).

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

"Heterologous," as used herein, means a nucleotide or polypeptide sequence that is not found in the native nucleic acid or protein, respectively. For example, in a chimeric Cas9 protein, the RNA-binding domain of a naturally-occurring bacterial Cas9 polypeptide (or a variant thereof) may be fused to a heterologous polypeptide sequence (i.e. a polypeptide sequence from a protein other than Cas9 or a polypeptide sequence from another organism). The heterologous polypeptide sequence may exhibit an activity (e.g., enzymatic activity) that will also be exhibited by the chimeric Cas9 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 polypeptide, a variant Cas9 polypeptide may be fused to a heterologous polypeptide (i.e. a polypeptide other than Cas9), which exhibits an activity that will also be exhibited by the fusion variant Cas9 polypeptide. A heterologous nucleic acid sequence may be linked to a variant Cas9 polypeptide (e.g., by genetic engineering) to generate a nucleotide sequence encoding a fusion variant polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. An example of such a case is a DNA (a recombinant) encoding a wild-type protein where the DNA sequence is codon optimized for expression of the protein in a cell (e.g., a eukaryotic cell) in which the protein is not naturally found (e.g., expression of a CRISPR/Cas endonuclease in a eukaryotic cell). A codon-optimized DNA can therefore be recombinant and non-naturally occurring while the protein encoded by the DNA may have a wild type amino acid sequence.

Thus, the term "recombinant" polypeptide does not necessarily refer to a polypeptide whose amino acid sequence does not naturally occur. Instead, a "recombinant" polypeptide is encoded by a recombinant non-naturally occurring DNA sequence, but the amino acid sequence of the polypeptide can be naturally occurring ("wild type") or non-naturally occurring (e.g., a variant, a mutant, etc.). Thus, a "recombinant" polypeptide is the result of human intervention, but may have a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence (or the coding sequence can also be said to be operably linked to the promoter) if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., DNA such as genomic DNA) that includes a site ("target site" or "target sequence") targeted by a genome editing endonuclease. When the genome editing endonuclease is a CRISPR/Cas endonuclease, the target sequence is the sequence to which the guide sequence of a subject CRISPR/Cas guide RNA (e.g., a Cas9 guide RNA) will hybridize. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand" or "target strand"; while the strand of the target nucleic acid that is complementary to the "target strand" (and is therefore not complementary to the guide RNA) is referred to as the "non-target strand" or "non-complementary strand".

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. In some embodiments, a complex comprising a CRISPR/Cas protein (e.g., a Cas9 protein) and a corresponding guide RNA is used for targeted cleavage of a double stranded DNA (dsDNA), e.g., induction of a double-stranded DNA break (DSB).

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.). A "genome editing endonuclease" is an endonuclease that can be used for the editing of a cell's genome (e.g., by cleaving at a targeted location within the cell's genomic DNA). Examples of genome editing endonucleases include but are not limited to: (i) Zinc finger nucleases, (ii) TAL endonucleases, and (iii) CRISPR/Cas endonucleases. Examples of CRISPR/Cas endonucleases include class 2 CRISPR/Cas endonucleases such as: (a) type II CRISPR/Cas proteins, e.g., a Cas9 protein; (b) type V CRISPR/Cas proteins, e.g., a Cpf1 polypeptide, a C2c1 polypeptide, a C2c3 polypeptide, and the like; and (c) type VI CRISPR/Cas proteins, e.g., a C2c2 polypeptide.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

A "host cell" or "target cell" as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a subject genome targeting composition, and include the progeny of the original cell (e.g., when the cell has been transformed by the nucleic acid, or when the cells genome has been modified by the genome targeting composition). It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a subject genome targeting composition, e.g., which can include a nucleic acid, e.g., an expression vector. For example, a subject bacterial host cell can be a genetically modified bacterial host cell by virtue of introduction into a suitable bacterial host cell of an exogenous nucleic acid (e.g., a plasmid or recombinant expression vector) and a subject eukaryotic host cell can be a genetically modified eukaryotic host cell (e.g., a mammalian germ cell), by virtue of introduction into a suitable eukaryotic host cell of an exogenous nucleic acid.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5):861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al.

(1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and U.S. Pat. No. 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, e.g., humans.

In some instances, a component (e.g., a nucleic acid component (e.g., a CRISPR/Cas guide RNA); a protein component (e.g., genome editing endonuclease such as a Cas9 protein); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels; e.g., a fluorescent label) and indirectly detectable labels (indirect labels; e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^{3}H$, $^{125}I$, $^{35}S$, $^{14}C$, or $^{32}P$); an enzyme (an indirect label) (e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a protein" includes a plurality of such proteins and reference to "the cell" includes reference to one or more cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods and compositions for enhanced editing of genomic DNA. For example, in some embodiments, a subject method is a method of editing genomic DNA of a eukaryotic cell and the method includes introducing into a eukaryotic cell a composition comprising a linearized non-homologous DNA composition and a genome targeting composition (which includes a genome editing endonuclease, or a nucleic acid encoding the genome editing endonuclease).

When used in combination with a genome targeting composition (that includes a genome editing endonuclease), the linearized non-homologous DNA composition of the subject methods and compositions increases the frequency of the generation of indels in targeted genomic DNA when the genomic DNA is cleaved with a genome editing endonuclease (e.g., a zinc finger nuclease, a TALEN, a class 2 CRISPR/Cas endonuclease, etc.). The inventors have discovered that including a linear non-homologous DNA composition increases the likelihood of error-prone end-joining. In other words, the presence of a linear non-homologous DNA composition decreases the rate of error-free NHEJ, and thereby increases the rate of insertions and deletions (indels) that are produced in the target DNA. Thus, in cases where one desires to edit the genomic DNA of a cell (e.g., in cases in which one wishes to generate an indel at a target position within a target genome), the inclusion of a subject linear non-homologous DNA composition can substantially increase the likelihood of success.

A method of the present disclosure (e.g., for genome editing), using a linearized non-homologous DNA composition, provides for an increased rate of error-prone DSB repair when compared to the method carried out without using a linearized non-homologous DNA composition. For example, a method of the present disclosure (e.g., for genome editing), using a linearized non-homologous DNA composition, can provide for increased error-prone non-homologous end-joining (NHEJ) (i.e., provides for an increase in insertion and/or deletion (indel) formation in the target genome) compared to a method that does not involve use of a linearized non-homologous DNA composition.

In some cases, a method of the present disclosure (e.g., for genome editing), using a linearized non-homologous DNA composition, provides for an at least 1.1-fold (e.g., at least 1.2-fold, at least 1.5-fold, at least 2-fold, at least 2.5-fold, at least 5-fold, at least 10-fold, at least 20-fold, at least 30-fold, at least 40-fold, or at least 50-fold) increase in indel generation within the target genome, compared with the rate of indel generation when the method is carried out without using a linearized non-homologous DNA composition.

In some cases, a method of the present disclosure (e.g., for genome editing), using a linearized non-homologous DNA composition, provides for an at least 1.1-fold (e.g., at least 1.2-fold, at least 1.5-fold, at least 2-fold, at least 2.5-fold, at least 5-fold, at least 10-fold, at least 20-fold, at least 30-fold, at least 40-fold, or at least 50-fold) increase in the number of target genomic DNA molecules that exhibit an insertion and/or deletion, compared with the number of target genomic DNA molecule that exhibit an insertion and/or deletion when the method is carried out without using a linearized non-homologous DNA composition.

In some cases, a method of the present disclosure (e.g., for genome editing), using a linearized non-homologous DNA composition, provides for an at least 1.1-fold (e.g., at least 1.2-fold, at least 1.5-fold, at least 2-fold, at least 2.5-fold, at least 5-fold, at least 10-fold, at least 20-fold, at least 30-fold, at least 40-fold, or at least 50-fold) increase in the number of cells of a targeted cell population that exhibit an insertion and/or deletion in their genomic DNA, compared with the number of cells of a targeted cell population that exhibit an insertion and/or deletion in their genomic DNA when the method is carried out without using a linearized non-homologous DNA composition.

Suitable linearized non-homologous DNA compositions and genome targeting compositions are described herein.

Linearized Non-Homologous DNA Composition

In some cases, a linearized non-homologous DNA composition is homogeneous (i.e., includes multiple copies on one particular DNA, e.g., an oligonucleotide). In some cases, a linearized non-homologous DNA composition is heterogeneous (i.e., includes a mixture of different DNAs, e.g., different oligonucleotides with different sequences, salmon sperm DNA, etc.).

Any convenient DNA can be used in a subject linearized non-homologous DNA composition (e.g., taking into account the detailed descriptions below related to the terms "non-homologous" and "linear"). Examples include but are not limited to, sheared (e.g., physically sheared, sonicated, digested, etc.) DNA (e.g., animal DNA, human DNA) such as sperm DNA (e.g., sheared salmon sperm DNA), single stranded oligonucleotides (e.g., having lengths as described below), double stranded linearized plasmid DNA, and the like.

In some cases, a subject linearized non-homologous DNA composition includes a linear DNA molecule (single or double stranded) that comprises the sequence CCTAGCTGAGTGAGCTAGTCA (SEQ ID NO: 1191) (e.g., in some cases in which it is desirable to insert a stop codon into a coding sequence).

In some cases, a subject linearized non-homologous DNA composition includes a linear DNA molecule (e.g., single stranded, double stranded, or in some cases a mix of single and double stranded) that is 80 or more nucleotides in length (e.g., 90 or more, 100 or more, 110 or more, or 120 or more nucleotides in length)(base pairs in length when referring to a double stranded molecule). In some cases, a subject linearized non-homologous DNA composition does not include (or is substantially free of) linear DNA molecules (e.g., single stranded, double stranded, or in some cases a mix of single and double stranded) that are less than 80 nucleotides in length (e.g., less than 90, less than 100, less than 110, or less than 120 nucleotides in length)(base pairs in length when referring to a double stranded molecule). By substantially free in this context is meant that less than 1% of the DNA of the composition is less than 80 nucleotides in length (e.g., less than 90, less than 100, less than 110, or less than 120 nucleotides in length)(base pairs in length when referring to a double stranded molecule).

In some cases, a subject linearized non-homologous DNA composition includes a linear DNA molecule (e.g., single stranded, double stranded, or in some cases a mix of single and double stranded) that is 3,000 or more nucleotides in length (e.g., 4,000 or more, 5,000 or more, 6,000 or more, 7,000 or more, 8,000 or more, or 9,000 or more nucleotides in length)(base pairs in length when referring to a double stranded molecule). In some cases, a subject linearized non-homologous DNA composition does not include (or is substantially free of) linear DNA molecules (e.g., single stranded, double stranded, or in some cases a mix of single and double stranded) that are less than 8,000 nucleotides in length (e.g., less than 7,000, less than 6,000, or less than 5,000 nucleotides in length)(base pairs in length when referring to a double stranded molecule). By substantially free in this context is meant that less than 1% of the DNA of the composition is less than 8,000 nucleotides in length (e.g., less than 7,000, less than 6,000, or less than 5,000 nucleotides in length)(base pairs in length when referring to a double stranded molecule).

In some cases, a subject linearized non-homologous DNA composition includes a linear DNA molecule (e.g., single stranded, double stranded, or in some cases a mix of single and double stranded) having a length in a range of from 100 to 14,000 nucleotides (nt) (e.g., from 100 to 13,000, from 100 to 12,000, from 100 to 11,000, from 100 to 10,000, from 100 to 9,000, from 100 to 8,000, from 100 to 7,000, from 100 to 6,000, from 100 to 5,000, from 100 to 4,000, from 100 to 3,000, from 100 to 2,000, from 100 to 1,000, from 100 to 800, from 100 to 600, from 100 to 500, from 100 to 400, from 100 to 300, from 200 to 14,000, from 200 to 13,000, from 200 to 12,000, from 200 to 11,000, from 200 to 10,000, from 200 to 9,000, from 200 to 8,000, from 200 to 7,000, from 200 to 6,000, from 200 to 5,000, from 200 to 4,000, from 200 to 3,000, from 200 to 2,000, from 200 to 1,000, from 200 to 800, from 200 to 600, from 200 to 500, from 200 to 400, from 200 to 300, from 500 to 14,000, from 500 to 13,000, from 500 to 12,000, from 500 to 11,000, from 500 to 10,000, from 500 to 9,000, from 500 to 8,000, from 500 to 7,000, from 500 to 6,000, from 500 to 5,000, from 500 to 4,000, from 500 to 3,000, from 500 to 2,000, from 500 to 1,000, from 500 to 800, from 500 to 600, from 800 to 14,000, from 800 to 13,000, from 800 to 12,000, from 800 to 11,000, from 800 to 10,000, from 800 to 9,000, from 800 to 8,000, from 800 to 7,000, from 800 to 6,000, from 800 to 5,000, from 800 to 4,000, from 800 to 3,000, from 800 to 2,000, from 800 to 1,000, from 1,000 to 14,000, from 1,000 to 13,000, from 1,000 to 12,000, from 1,000 to 11,000, from 1,000 to 10,000, from 1,000 to 9,000, from 1,000 to 8,000, from 1,000 to 7,000, from 1,000 to 6,000, from 1,000 to 5,000, from 1,000 to 4,000, from 1,000 to 3,000, from 1,000 to 2,000, from 3,000 to 14,000, from 3,000 to 13,000, from 3,000 to 12,000, from 3,000 to 11,000, from 3,000 to 10,000, from 3,000 to 9,000, from 3,000 to 8,000, from 3,000 to 7,000, from 3,000 to 6,000, from 3,000 to 5,000, from 3,000 to 4,000, from 5,000 to 14,000, from 5,000 to 13,000, from 5,000 to 12,000, from 5,000 to 11,000, from 5,000 to 10,000, from 5,000 to 9,000, from 5,000 to 8,000, from 5,000 to 7,000, from 5,000 to 6,000, from 7,000 to 14,000, from 7,000 to 13,000, from 7,000 to 12,000, from 7,000 to 11,000, from 7,000 to 10,000, from 7,000 to 9,000, or from 7,000 to 8,000 nucleotides) (base pairs when referring to a double stranded molecule).

"Non-Homologous"

A linearized non-homologous DNA composition includes DNA that is non-homologous to the targeted locus of a target genomic DNA. By "non-homologous" as used in this context, it is meant that a subject linearized non-homologous DNA composition does not include homology arms, e.g., it is free of a 5' (upstream) homology arm and/or free of a 3' (downstream) homology arm (relative to the target site of the targeted genomic DNA). In some cases, a non-homologous DNA composition does not include a 5' homology arm. In some cases, a non-homologous DNA composition does not include a 3' homology arm. In some cases, a non-homologous DNA composition does not include a 3' homology arm and does not include a 5' homology arm. In some cases, a non-homologous DNA composition is free of at least one of: a 5' homology arm and a 3' homology arm. In some cases, a non-homologous DNA composition is free of a 5' homology arm and free of a 3' homology arm.

As used in the art in methods that employ homologous recombination, a donor nucleotide sequence (i.e., a sequence to be incorporated into the target DNA) is flanked by regions ("homology arms") that have homology to the regions flanking the target site in the chromosome. Homology arms provide for homologous recombination between the donor DNA molecule (a donor DNA template) and the target DNA molecule. Generally speaking, the extent of homology between corresponding homology arms must be sufficient to allow homologous recombination to occur. Factors affecting whether homologous recombination can occur are the sequence identity between the corresponding homology arms and the base-pair size of the homology arms. Typically, at least 80% sequence identity is required between corresponding homology arms for homologous recombination to occur (e.g., at least 85%, at least 90%, at least 95%, at least 98%, or in some cases 100%. Typically, the size of each homology arm is 50 bp or more (e.g., 75 bp or more, 100 bp or more, 200 bp or more, 300 bp or more, 500 bp or more, 1000 bp or more, etc.). There is no particular upper limit for the size of a homology arm although in practice this may be governed by the size of the donor DNA molecule, which typically would have at least two homology arms (an upstream and a downstream homology arm, meaning one homology arm upstream of the target site and one homology arm downstream of the target site). Homology arms can be as large as 1 kb, or up to 2 kb, up to 5 kb, up to 10 kb, even up to 50 kb.

It is recognized that in some cases, all or some portion of the DNA molecules of a linearized non-homologous DNA composition may have some homology to a stretch of nucleotides flanking the target site of the target DNA. Thus, the phrase "a subject linearized non-homologous DNA composition does not include homology arms" means that a subject linearized non-homologous DNA composition is free of DNA that has 80% or more (e.g., 85% or more, 90% or more, 95% or more, 98% or more, or 99% or more) sequence identity over 50 or more contiguous nucleotides (nt) (e.g., 75 or more nt, 100 or more nt, 250 or more nt, or 500 or more nt) flanking (adjacent to) the target site of the genomic DNA. In other words, a subject linearized non-homologous DNA composition can be free of DNA that has 80% or more (e.g., 85% or more, 90% or more, 95% or more, 98% or more, or 99% or more) sequence identity over the 50 or more contiguous nucleotides (nt) (e.g., 75 or more nt, 100 or more nt, 250 or more nt, or 500 or more nt) upstream and adjacent to the target site of the genomic DNA; and is free of DNA that has 80% or more (e.g., 85% or more, 90% or more, 95% or more, 98% or more, or 99% or more) sequence identity over 50 or more contiguous nucleotides (nt) (e.g., 75 or more nt, 100 or more nt, 250 or more nt, or 500 or more nt) downstream and adjacent to the target site of the genomic DNA.

In some cases, a subject linearized non-homologous DNA composition is free of DNA that has 85% or more (e.g., 90% or more, 95% or more, 98% or more, or 99% or more) sequence identity over 50 or more contiguous nucleotides (nt) (e.g., 75 or more nt, 100 or more nt, 250 or more nt, or 500 or more nt) flanking (adjacent to) the target site of the genomic DNA. In other words, a subject linearized non-homologous DNA composition is free of DNA that has 85% or more (e.g., 90% or more, 95% or more, 98% or more, or 99% or more) sequence identity over 50 or more contiguous nucleotides (nt) (e.g., 75 or more nt, 100 or more nt, 250 or more nt, or 500 or more nt) upstream and adjacent to the target site of the genomic DNA; and is free of DNA that has 90% or more (e.g., 95% or more, 98% or more, or 99% or more) sequence identity over 50 or more contiguous nucleotides (nt) (e.g., 75 or more nt, 100 or more nt, 250 or more nt, or 500 or more nt) downstream and adjacent to the target site of the genomic DNA.

In some cases, a subject linearized non-homologous DNA composition is free of DNA that has 90% or more (e.g., 95% or more, 98% or more, or 99% or more) sequence identity over 50 or more contiguous nucleotides (nt) (e.g., 75 or more nt, 100 or more nt, 250 or more nt, or 500 or more nt) flanking (adjacent to) the target site of the genomic DNA. In other words, a subject linearized non-homologous DNA composition is free of DNA that has 90% or more (e.g., 95% or more, 98% or more, or 99% or more) sequence identity over 50 or more contiguous nucleotides (nt) (e.g., 75 or more nt, 100 or more nt, 250 or more nt, or 500 or more nt) upstream and adjacent to the target site of the genomic DNA; and is free of DNA that has 90% or more (e.g., 95% or more, 98% or more, or 99% or more) sequence identity over 50 or more contiguous nucleotides (nt) (e.g., 75 or more nt, 100 or more nt, 250 or more nt, or 500 or more nt) downstream and adjacent to the target site of the genomic DNA.

In some cases, a subject linearized non-homologous DNA composition is free of DNA that has 95% or more (e.g., 98% or more, or 99% or more) sequence identity over 50 or more contiguous nucleotides (nt) (e.g., 75 or more nt, 100 or more nt, 250 or more nt, or 500 or more nt) flanking (adjacent to) the target site of the genomic DNA. In other words, a subject linearized non-homologous DNA composition is free of DNA that has 95% or more (e.g., 98% or more, or 99% or more) sequence identity over 50 or more contiguous nucleotides (nt) (e.g., 75 or more nt, 100 or more nt, 250 or more nt, or 500 or more nt) upstream and adjacent to the target site of the genomic DNA; and is free of DNA that has 95% or more (e.g., 98% or more, or 99% or more) sequence identity over 50 or more contiguous nucleotides (nt) (e.g., 75 or more nt, 100 or more nt, 250 or more nt, or 500 or more nt) downstream and adjacent to the target site of the genomic DNA.

In some cases, a subject linearized non-homologous DNA composition is free of DNA that has 80% or more (e.g., 85% or more, 90% or more, 95% or more, 98% or more, or 99% or more) sequence identity over the 50 nucleotides (nt) flanking (adjacent to) the target site of the genomic DNA. In other words, a subject linearized non-homologous DNA composition is free of DNA that has 80% or more (e.g., 85% or more, 90% or more, 95% or more, 98% or more, or 99% or more) sequence identity over the 50 nucleotides (nt) upstream and adjacent to the target site of the genomic DNA; and is free of DNA that has 80% or more (e.g., 85% or more, 90% or more, 95% or more, 98% or more, or 99% or more) sequence identity over the 50 nucleotides (nt) downstream and adjacent to the target site of the genomic DNA.

In some cases, a subject linearized non-homologous DNA composition is free of DNA that has 85% or more (e.g., 90% or more, 95% or more, 98% or more, or 99% or more) sequence identity over the 50 nucleotides (nt) flanking (adjacent to) the target site of the genomic DNA. In other words, a subject linearized non-homologous DNA composition is free of DNA that has 85% or more (e.g., 90% or more, 95% or more, 98% or more, or 99% or more) sequence identity over the 50 nucleotides (nt) upstream and adjacent to the target site of the genomic DNA; and is free of DNA that has 85% or more (e.g., 90% or more, 95% or more, 98% or more, or 99% or more) sequence identity over the 50 nucleotides (nt) downstream and adjacent to the target site of the genomic DNA.

In some cases, a subject linearized non-homologous DNA composition is free of DNA that has 90% or more (e.g., 95% or more, 98% or more, or 99% or more) sequence identity over the 50 nucleotides (nt) flanking (adjacent to) the target site of the genomic DNA. In other words, a subject linearized non-homologous DNA composition is free of DNA that has 90% or more (e.g., 95% or more, 98% or more, or 99% or more) sequence identity over the 50 nt upstream and adjacent to the target site of the genomic DNA; and is free of DNA that has 90% or more (e.g., 95% or more, 98% or more, or 99% or more) sequence identity over the 50 nt downstream and adjacent to the target site of the genomic DNA.

In some cases, a subject linearized non-homologous DNA composition is free of DNA that has 95% or more (e.g., 98% or more, or 99% or more) sequence identity over the 50 nucleotides (nt) flanking (adjacent to) the target site of the genomic DNA. In other words, a subject linearized non-homologous DNA composition is free of DNA that has 95% or more (e.g., 98% or more, or 99% or more) sequence identity over the 50 nt upstream and adjacent to the target site of the genomic DNA; and is free of DNA that has 95% or more (e.g., 98% or more, or 99% or more) sequence identity over the 50 nt downstream and adjacent to the target site of the genomic DNA.

In some cases, a subject linearized non-homologous DNA composition is free of DNA that has 80% or more (e.g., 85% or more, 90% or more, 95% or more, 98% or more, or 99% or more) sequence identity over 100 or more contiguous nucleotides (nt) (e.g., 250 or more nt, or 500 or more nt) flanking (adjacent to) the target site of the genomic DNA. In other words, a subject linearized non-homologous DNA composition can be free of DNA that has 80% or more (e.g., 85% or more, 90% or more, 95% or more, 98% or more, or 99% or more) sequence identity over the 100 or more contiguous nucleotides (nt) (e.g., 250 or more nt, or 500 or more nt) upstream and adjacent to the target site of the genomic DNA; and is free of DNA that has 80% or more (e.g., 85% or more, 90% or more, 95% or more, 98% or more, or 99% or more) sequence identity over 100 or more contiguous nucleotides (nt) (e.g., 250 or more nt, or 500 or more nt) downstream and adjacent to the target site of the genomic DNA.

In some cases, a subject linearized non-homologous DNA composition is free of DNA that has 85% or more (e.g., 90% or more, 95% or more, 98% or more, or 99% or more) sequence identity over 100 or more contiguous nucleotides (nt) (e.g., 250 or more nt, or 500 or more nt) flanking (adjacent to) the target site of the genomic DNA. In other words, a subject linearized non-homologous DNA composition is free of DNA that has 85% or more (e.g., 90% or more, 95% or more, 98% or more, or 99% or more) sequence identity over 100 or more contiguous nucleotides (nt) (e.g., 250 or more nt, or 500 or more nt) upstream and adjacent to the target site of the genomic DNA; and is free of DNA that has 90% or more (e.g., 95% or more, 98% or more, or 99% or more) sequence identity over 100 or more contiguous nucleotides (nt) (e.g., 250 or more nt, or 500 or more nt) downstream and adjacent to the target site of the genomic DNA.

In some cases, a subject linearized non-homologous DNA composition is free of DNA that has 90% or more (e.g., 95% or more, 98% or more, or 99% or more) sequence identity over 100 or more contiguous nucleotides (nt) (e.g., 250 or more nt, or 500 or more nt) flanking (adjacent to) the target site of the genomic DNA. In other words, a subject linearized non-homologous DNA composition is free of DNA that has 90% or more (e.g., 95% or more, 98% or more, or 99% or more) sequence identity over 100 or more contiguous nucleotides (nt) (e.g., 250 or more nt, or 500 or more nt) upstream and adjacent to the target site of the genomic DNA; and is free of DNA that has 90% or more (e.g., 95% or more, 98% or more, or 99% or more) sequence identity over 100 or more contiguous nucleotides (nt) (e.g., 250 or more nt, or 500 or more nt) downstream and adjacent to the target site of the genomic DNA.

In some cases, a subject linearized non-homologous DNA composition is free of DNA that has 95% or more (e.g., 98% or more, or 99% or more) sequence identity over 100 or more contiguous nucleotides (nt) (e.g., 250 or more nt, or 500 or more nt) flanking (adjacent to) the target site of the genomic DNA. In other words, a subject linearized non-homologous DNA composition is free of DNA that has 95% or more (e.g., 98% or more, or 99% or more) sequence identity over 100 or more contiguous nucleotides (nt) (e.g., 250 or more nt, or 500 or more nt) upstream and adjacent to the target site of the genomic DNA; and is free of DNA that has 95% or more (e.g., 98% or more, or 99% or more) sequence identity over 100 or more contiguous nucleotides (nt) (e.g., 250 or more nt, or 500 or more nt) downstream and adjacent to the target site of the genomic DNA.

In some cases, a subject linearized non-homologous DNA composition is free of DNA that has 80% or more (e.g., 85% or more, 90% or more, 95% or more, 98% or more, or 99% or more) sequence identity over the 100 nucleotides (nt) flanking (adjacent to) the target site of the genomic DNA. In other words, a subject linearized non-homologous DNA composition is free of DNA that has 80% or more (e.g., 85% or more, 90% or more, 95% or more, 98% or more, or 99% or more) sequence identity over the 100 nucleotides (nt) upstream and adjacent to the target site of the genomic DNA; and is free of DNA that has 80% or more (e.g., 85% or more, 90% or more, 95% or more, 98% or more, or 99% or more) sequence identity over the 100 nucleotides (nt) downstream and adjacent to the target site of the genomic DNA.

In some cases, a subject linearized non-homologous DNA composition is free of DNA that has 85% or more (e.g., 90% or more, 95% or more, 98% or more, or 99% or more) sequence identity over the 100 nucleotides (nt) flanking (adjacent to) the target site of the genomic DNA. In other words, a subject linearized non-homologous DNA composition is free of DNA that has 85% or more (e.g., 90% or more, 95% or more, 98% or more, or 99% or more) sequence identity over the 100 nucleotides (nt) upstream and adjacent to the target site of the genomic DNA; and is free of DNA that has 85% or more (e.g., 90% or more, 95% or more, 98% or more, or 99% or more) sequence identity over the 100 nucleotides (nt) downstream and adjacent to the target site of the genomic DNA.

In some cases, a subject linearized non-homologous DNA composition is free of DNA that has 90% or more (e.g., 95% or more, 98% or more, or 99% or more) sequence identity over the 100 nucleotides (nt) flanking (adjacent to) the target site of the genomic DNA. In other words, a subject linearized non-homologous DNA composition is free of DNA that has 90% or more (e.g., 95% or more, 98% or more, or 99% or more) sequence identity over the 100 nt upstream and adjacent to the target site of the genomic DNA; and is free of DNA that has 90% or more (e.g., 95% or more, 98% or more, or 99% or more) sequence identity over the 100 nt downstream and adjacent to the target site of the genomic DNA.

In some cases, a subject linearized non-homologous DNA composition is free of DNA that has 95% or more (e.g., 98% or more, or 99% or more) sequence identity over the 100 nucleotides (nt) flanking (adjacent to) the target site of the genomic DNA. In other words, a subject linearized non-homologous DNA composition is free of DNA that has 95% or more (e.g., 98% or more, or 99% or more) sequence identity over the 100 nt upstream and adjacent to the target site of the genomic DNA; and is free of DNA that has 95% or more (e.g., 98% or more, or 99% or more) sequence identity over the 100 nt downstream and adjacent to the target site of the genomic DNA.

In some cases, a subject linearized non-homologous DNA composition is free of DNA that has 80% or more (e.g., 85% or more, 90% or more, 95% or more, 98% or more, or 99% or more) sequence identity over 250 or more contiguous nucleotides (nt) (e.g., 500 or more nt) flanking (adjacent to) the target site of the genomic DNA. In other words, a subject linearized non-homologous DNA composition can be free of DNA that has 80% or more (e.g., 85% or more, 90% or more, 95% or more, 98% or more, or 99% or more) sequence identity over the 250 or more contiguous nucleotides (nt) (e.g., 500 or more nt) upstream and adjacent to the target site of the genomic DNA; and is free of DNA that has 80% or more (e.g., 85% or more, 90% or more, 95% or more, 98% or more, or 99% or more) sequence identity over 250 or more contiguous nucleotides (nt) (e.g., 500 or more nt) downstream and adjacent to the target site of the genomic DNA.

In some cases, a subject linearized non-homologous DNA composition is free of DNA that has 85% or more (e.g., 90% or more, 95% or more, 98% or more, or 99% or more) sequence identity over 250 or more contiguous nucleotides (nt) (e.g., 500 or more nt) flanking (adjacent to) the target site of the genomic DNA. In other words, a subject linearized non-homologous DNA composition is free of DNA that has 85% or more (e.g., 90% or more, 95% or more, 98% or more, or 99% or more) sequence identity over 250 or more contiguous nucleotides (nt) (e.g., 500 or more nt) upstream and adjacent to the target site of the genomic DNA; and is free of DNA that has 90% or more (e.g., 95% or more, 98% or more, or 99% or more) sequence identity over 250 or more contiguous nucleotides (nt) (e.g., 500 or more nt) downstream and adjacent to the target site of the genomic DNA.

In some cases, a subject linearized non-homologous DNA composition is free of DNA that has 90% or more (e.g., 95% or more, 98% or more, or 99% or more) sequence identity over 250 or more contiguous nucleotides (nt) (e.g., 500 or more nt) flanking (adjacent to) the target site of the genomic DNA. In other words, a subject linearized non-homologous DNA composition is free of DNA that has 90% or more (e.g., 95% or more, 98% or more, or 99% or more) sequence identity over 250 or more contiguous nucleotides (nt) (e.g., 500 or more nt) upstream and adjacent to the target site of the genomic DNA; and is free of DNA that has 90% or more (e.g., 95% or more, 98% or more, or 99% or more) sequence identity over 250 or more contiguous nucleotides (nt) (e.g., 500 or more nt) downstream and adjacent to the target site of the genomic DNA.

In some cases, a subject linearized non-homologous DNA composition is free of DNA that has 95% or more (e.g., 98% or more, or 99% or more) sequence identity over 250 or more contiguous nucleotides (nt) (e.g., 500 or more nt) flanking (adjacent to) the target site of the genomic DNA. In other words, a subject linearized non-homologous DNA composition is free of DNA that has 95% or more (e.g., 98% or more, or 99% or more) sequence identity over 250 or more contiguous nucleotides (nt) (e.g., 500 or more nt) upstream and adjacent to the target site of the genomic DNA; and is free of DNA that has 95% or more (e.g., 98% or more, or 99% or more) sequence identity over 250 or more contiguous nucleotides (nt) (e.g., 500 or more nt) downstream and adjacent to the target site of the genomic DNA.

In some cases, a subject linearized non-homologous DNA composition is free of DNA that has 80% or more (e.g., 85% or more, 90% or more, 95% or more, 98% or more, or 99% or more) sequence identity over the 250 nucleotides (nt) flanking (adjacent to) the target site of the genomic DNA. In other words, a subject linearized non-homologous DNA composition is free of DNA that has 80% or more (e.g., 85% or more, 90% or more, 95% or more, 98% or more, or 99% or more) sequence identity over the 250 nucleotides (nt) upstream and adjacent to the target site of the genomic DNA; and is free of DNA that has 80% or more (e.g., 85% or more, 90% or more, 95% or more, 98% or more, or 99% or more) sequence identity over the 250 nucleotides (nt) downstream and adjacent to the target site of the genomic DNA.

In some cases, a subject linearized non-homologous DNA composition is free of DNA that has 85% or more (e.g., 90% or more, 95% or more, 98% or more, or 99% or more) sequence identity over the 250 nucleotides (nt) flanking (adjacent to) the target site of the genomic DNA. In other words, a subject linearized non-homologous DNA composition is free of DNA that has 85% or more (e.g., 90% or more, 95% or more, 98% or more, or 99% or more) sequence identity over the 250 nucleotides (nt) upstream and adjacent to the target site of the genomic DNA; and is free of DNA that has 85% or more (e.g., 90% or more, 95% or more, 98% or more, or 99% or more) sequence identity over the 250 nucleotides (nt) downstream and adjacent to the target site of the genomic DNA.

In some cases, a subject linearized non-homologous DNA composition is free of DNA that has 90% or more (e.g., 95% or more, 98% or more, or 99% or more) sequence identity over the 250 nucleotides (nt) flanking (adjacent to) the target site of the genomic DNA. In other words, a subject linearized non-homologous DNA composition is free of DNA that has 90% or more (e.g., 95% or more, 98% or more, or 99% or more) sequence identity over the 250 nt upstream and adjacent to the target site of the genomic DNA; and is free of DNA that has 90% or more (e.g., 95% or more, 98% or more, or 99% or more) sequence identity over the 250 nt downstream and adjacent to the target site of the genomic DNA.

In some cases, a subject linearized non-homologous DNA composition is free of DNA that has 95% or more (e.g., 98% or more, or 99% or more) sequence identity over the 250 nucleotides (nt) flanking (adjacent to) the target site of the genomic DNA. In other words, a subject linearized non-homologous DNA composition is free of DNA that has 95% or more (e.g., 98% or more, or 99% or more) sequence identity over the 250 nt upstream and adjacent to the target site of the genomic DNA; and is free of DNA that has 95% or more (e.g., 98% or more, or 99% or more) sequence identity over the 250 nt downstream and adjacent to the target site of the genomic DNA.

In some cases, a subject linearized non-homologous DNA composition is free of DNA that has 85% or more (e.g., 90% or more, 95% or more, 98% or more, or 99% or more) sequence identity over a 200 nucleotide (nt) stretch anywhere in the target genome. In some cases, a subject linearized non-homologous DNA composition is free of DNA that has 90% or more (e.g., 95% or more, 98% or more, or 99% or more) sequence identity over a 200 nucleotide (nt) stretch anywhere in the target genome. In some cases, a subject linearized non-homologous DNA composition is free of DNA that has 95% or more (e.g., 98% or more, or 99% or more) sequence identity over a 200 nucleotide (nt) stretch anywhere in the target genome.

In some cases, a subject linearized non-homologous DNA composition is free of DNA that has 85% or more (e.g., 90% or more, 95% or more, 98% or more, or 99% or more) sequence identity over a 500 nucleotide (nt) stretch anywhere in the target genome. In some cases, a subject linearized non-homologous DNA composition is free of DNA that has 90% or more (e.g., 95% or more, 98% or more, or 99% or more) sequence identity over a 500 nucleotide (nt) stretch anywhere in the target genome. In some cases, a subject linearized non-homologous DNA composition is free of DNA that has 95% or more (e.g., 98% or more, or 99% or more) sequence identity over a 500 nucleotide (nt) stretch anywhere in the target genome.

In some cases, (e.g., in any of the above scenarios of this "non-homologous" section), a subject linearized non-homologous DNA composition includes a linear DNA that includes a region of microhomology. For example, the inventors have discovered that in some cases, when a linear DNA molecule of a subject non-homologous DNA composition includes a short stretch of homology with the target DNA near the target locus, capture of sequence from the linear DNA molecule (e.g., insertion of sequence from the linear DNA molecule) can increase. In other words, the likelihood of an insertion can be increased relative to the likelihood of a deletion). Thus, in some cases, a subject non-homologous DNA composition includes a linear DNA molecule that includes a stretch of microhomology to the target locus (e.g., despite not having a 5' homology arm and/or a 3' homology arm, as described above in this section).

By "region of microhomology" is meant a stretch of nucleotides of a linear DNA molecule (double or single stranded) of a non-homologous DNA composition that has homology to a stretch of nucleotides at or near the target site in the genome. Such a stretch of nucleotides (within the linear DNA molecule of a non-homologous DNA composition) can have a length in a range of from 2 to 40 nucleotides (nt) (2 to 40 base pairs (bp) if double stranded) (e.g., 2 to 35 nt, 2 to 25 nt, 2 to 20 nt, 2 to 15 nt, 2 to 10 nt, 3 to 40 nt, 3 to 35 nt, 3 to 25 nt, 3 to 20 nt, 3 to 15 nt, 3 to 10 nt, 5 to 40 nt, 5 to 35 nt, 5 to 25 nt, 5 to 20 nt, 5 to 15 nt, 5 to 10 nt, 10 to 40 nt, 10 to 35 nt, 10 to 30 nt, 10 to 25 nt, 10 to 20 nt, 10 to 15 nt, 15 to 40 nt, 15 to 35 nt, 15 to 30 nt, 15 to 25 nt, 15 to 20 nt, 20 to 40 nt, 20 to 35 nt, 20 to 30 nt, 20 to 25 nt, 25 to 40 nt, 25 to 35 nt, 25 to 30 nt, 30 to 40 nt, or 30 to 35 nt) (e.g., 2 to 35 bp, 2 to 25 bp, 2 to 20 bp, 2 to 15 bp, 2 to 10 bp, 3 to 40 bp, 3 to 35 bp, 3 to 25 bp, 3 to 20 bp, 3 to 15 bp, 3 to 10 bp, 5 to 40 bp, 5 to 35 bp, 5 to 25 bp, 5 to 20 bp, 5 to 15 bp, 5 to 10 bp, 10 to 40 bp, 10 to 35 bp, 10 to 30 bp, 10 to 25 bp, 10 to 20 bp, 10 to 15 bp, 15 to 40 bp, 15 to 35 bp, 15 to 30 bp, 15 to 25 bp, 15 to 20 bp, 20 to 40 bp, 20 to 35 bp, 20 to 30 bp, 20 to 25 bp, 25 to 40 bp, 25 to 35 bp, 25 to 30 bp, 30 to 40 bp, or 30 to 35 bp) and the complementarity (sequence identity) can be 90% or more over that stretch (e.g., 95% or more, 97% or more, 98% or more, 99% or more, or 100% sequence identity over that stretch).

For example, in some cases, a linear DNA molecule (double or single stranded) of a non-homologous DNA composition includes a stretch of nucleotides having 90% or more sequence identity with nucleotides at or near the target site of the genome and the stretch of nucleotides has a length in a range of from 2 to 40 nucleotides (nt) (2 to 40 base pairs (bp) if double stranded) (e.g., 2 to 35 nt, 2 to 25 nt, 2 to 20 nt, 2 to 15 nt, 2 to 10 nt, 3 to 40 nt, 3 to 35 nt, 3 to 25 nt, 3 to 20 nt, 3 to 15 nt, 3 to 10 nt, 5 to 40 nt, 5 to 35 nt, 5 to 25 nt, 5 to 20 nt, 5 to 15 nt, 5 to 10 nt, 10 to 40 nt, 10 to 35 nt, 10 to 30 nt, 10 to 25 nt, 10 to 20 nt, 10 to 15 nt, 15 to 40 nt, 15 to 35 nt, 15 to 30 nt, 15 to 25 nt, 15 to 20 nt, 20 to 40 nt, 20 to 35 nt, 20 to 30 nt, 20 to 25 nt, 25 to 40 nt, 25 to 35 nt, 25 to 30 nt, 30 to 40 nt, 30 to 35 nt). In some cases, a linear DNA molecule (double or single stranded) of a non-homologous DNA composition includes a stretch of nucleotides having 95% or more sequence identity with nucleotides at or near the target site of the genome and the stretch of nucleotides has a length in a range of from 2 to 40 nucleotides (nt) (2 to 40 base pairs (bp) if double stranded) (e.g., 2 to 35 nt, 2 to 25 nt, 2 to 20 nt, 2 to 15 nt, 2 to 10 nt, 3 to 40 nt, 3 to 35 nt, 3 to 25 nt, 3 to 20 nt, 3 to 15 nt, 3 to 10 nt, 5 to 40 nt, 5 to 35 nt, 5 to 25 nt, 5 to 20 nt, 5 to 15 nt, 5 to 10 nt, 10 to 40 nt, 10 to 35 nt, 10 to 30 nt, 10 to 25 nt, 10 to 20 nt, 10 to 15 nt, 15 to 40 nt, 15 to 35 nt, 15 to 30 nt, 15 to 25 nt, 15 to 20 nt, 20 to 40 nt, 20 to 35 nt, 20 to 30 nt, 20 to 25 nt, 25 to 40 nt, 25 to 35 nt, 25 to 30 nt, 30 to 40 nt, 30 to 35 nt). In some cases, a linear DNA molecule (double or single stranded) of a non-homologous DNA composition includes a stretch of nucleotides having 98% or more sequence identity with nucleotides at or near the target site of the genome and the stretch of nucleotides has a length in a range of from 2 to 40 nucleotides (nt) (2 to 40 base pairs (bp) if double stranded) (e.g., 2 to 35 nt, 2 to 25 nt, 2 to 20 nt, 2 to 15 nt, 2 to 10 nt, 3 to 40 nt, 3 to 35 nt, 3 to 25 nt, 3 to 20 nt, 3 to 15 nt, 3 to 10 nt, 5 to 40 nt, 5 to 35 nt, 5 to 25 nt, 5 to 20 nt, 5 to 15 nt, 5 to 10 nt, 10 to 40 nt, 10 to 35 nt, 10 to 30 nt, 10 to 25 nt, 10 to 20 nt, 10 to 15 nt, 15 to 40 nt, 15 to 35 nt, 15 to 30 nt, 15 to 25 nt, 15 to 20 nt, 20 to 40 nt, 20 to 35 nt, 20 to 30 nt, 20 to 25 nt, 25 to 40 nt, 25 to 35 nt, 25 to 30 nt, 30 to 40 nt, 30 to 35 nt). In some cases, a linear DNA molecule (double or single stranded) of a non-homologous DNA composition includes a stretch of nucleotides having 100% sequence identity with nucleotides at or near the target site of the genome and the stretch of nucleotides has a length in a range of from 2 to 40 nucleotides (nt) (2 to 40 base pairs (bp) if double stranded) (e.g., 2 to 35 nt, 2 to 25 nt, 2 to 20 nt, 2 to 15 nt, 2 to 10 nt, 3 to 40 nt, 3 to 35 nt, 3 to 25 nt, 3 to 20 nt, 3 to 15 nt, 3 to 10 nt, 5 to 40 nt, 5 to 35 nt, 5 to 25 nt, 5 to 20 nt, 5 to 15 nt, 5 to 10 nt, 10 to 40 nt, 10 to 35 nt, 10 to 30 nt, 10 to 25 nt, 10 to 20 nt, 10 to 15 nt, 15 to 40 nt, 15 to 35 nt, 15 to 30 nt, 15 to 25 nt, 15 to 20 nt, 20 to 40 nt, 20 to 35 nt, 20 to 30 nt, 20 to 25 nt, 25 to 40 nt, 25 to 35 nt, 25 to 30 nt, 30 to 40 nt, 30 to 35 nt).

For example, in some cases, a linear DNA molecule (double or single stranded) of a non-homologous DNA composition includes a stretch of nucleotides having 90% or more sequence identity with nucleotides at or near the target site of the genome and the stretch of nucleotides has a length in a range of from 5 to 30 nucleotides (nt) (e.g., 5 to 25 nt, 5 to 20 nt, 5 to 15 nt, 5 to 10 nt, 10 to 30 nt, 10 to 25 nt, 10 to 20 nt, 10 to 15 nt, 15 to 30 nt, 15 to 25 nt, 15 to 20 nt, 20 to 30 nt, 20 to 25 nt, or 25 to 30 nt). In some cases, a linear DNA molecule (double or single stranded) of a non-homologous DNA composition includes a stretch of nucleotides having 95% or more sequence identity with nucleotides at or near the target site of the genome and the stretch of nucleotides has a length in a range of from 5 to 30 nucleotides (nt) (e.g., 5 to 25 nt, 5 to 20 nt, 5 to 15 nt, 5 to 10 nt, 10 to 30 nt, 10 to 25 nt, 10 to 20 nt, 10 to 15 nt, 15 to 30 nt, 15 to 25 nt, 15 to 20 nt, 20 to 30 nt, 20 to 25 nt, or 25 to 30 nt). In some cases, a linear DNA molecule (double or single stranded) of a non-homologous DNA composition includes a stretch of nucleotides having 98% or more sequence identity with nucleotides at or near the target site of the genome and the stretch of nucleotides has a length in a range of from 5 to 30 nucleotides (nt) (e.g., 5 to 25 nt, 5 to 20 nt, 5 to 15 nt, 5 to 10 nt, 10 to 30 nt, 10 to 25 nt, 10 to 20 nt, 10 to 15 nt, 15 to 30 nt, 15 to 25 nt, 15 to 20 nt, 20 to 30 nt, 20 to 25 nt, or 25 to 30 nt). In some cases, a linear DNA molecule (double or single stranded) of a non-homologous DNA composition includes a stretch of nucleotides having 100% sequence identity with nucleotides at or near the target site of the genome and the stretch of nucleotides has a length in a range of from 5 to 30 nucleotides (nt) (e.g., 5 to 25 nt, 5 to 20 nt, 5 to 15 nt, 5 to 10 nt, 10 to 30 nt, 10 to 25 nt, 10 to 20 nt, 10 to 15 nt, 15 to 30 nt, 15 to 25 nt, 15 to 20 nt, 20 to 30 nt, 20 to 25 nt, or 25 to 30 nt).

For example, in some cases, a linear DNA molecule (double or single stranded) of a non-homologous DNA composition includes a stretch of nucleotides having 90% or more sequence identity with nucleotides at or near the target site of the genome and the stretch of nucleotides has a length in a range of from 2 to 30 nucleotides (nt) (e.g., 2 to 25 nt, 2 to 20 nt, 2 to 15 nt, 2 to 10 nt, 3 to 30 nt, 3 to 25 nt, 3 to 20 nt, 3 to 15 nt, 3 to 10 nt, 5 to 30 nt, 5 to 25 nt, 5 to 20 nt, 5 to 15 nt, 5 to 10 nt, 10 to 30 nt, 10 to 25 nt, 10 to 20 nt, 10 to 15 nt, 15 to 30 nt, 15 to 25 nt, 15 to 20 nt, 20 to 30 nt, 20 to 25 nt, or 25 to 30 nt). In some cases, a linear DNA molecule (double or single stranded) of a non-homologous DNA composition includes a stretch of nucleotides having 95% or more sequence identity with nucleotides at or near the target site of the genome and the stretch of nucleotides has a length in a range of from 2 to 30 nucleotides (nt) (e.g., 2 to 25 nt, 2 to 20 nt, 2 to 15 nt, 2 to 10 nt, 3 to 30 nt, 3 to 25 nt, 3 to 20 nt, 3 to 15 nt, 3 to 10 nt, 5 to 30 nt, 5 to 25 nt, 5 to 20 nt, 5 to 15 nt, 5 to 10 nt, 10 to 30 nt, 10 to 25 nt, 10 to 20 nt, 10 to 15 nt, 15 to 30 nt, 15 to 25 nt, 15 to 20 nt, 20 to 30 nt, 20 to 25 nt, or 25 to 30 nt). In some cases, a linear DNA molecule (double or single stranded) of a non-homologous DNA composition includes a stretch of nucleotides having 98% or more sequence identity with nucleotides at or near the target site of the genome and the stretch of nucleotides has a length in a range of from 2 to 30 nucleotides (nt) (e.g., 2 to 25 nt, 2 to 20 nt, 2 to 15 nt, 2 to 10 nt, 3 to 30 nt, 3 to 25 nt, 3 to 20 nt, 3 to 15 nt, 3 to 10 nt, 5 to 30 nt, 5 to 25 nt, 5 to 20 nt, 5 to 15 nt, 5 to 10 nt, 10 to 30 nt, 10 to 25 nt, 10 to 20 nt, 10 to 15 nt, 15 to 30 nt, 15 to 25 nt, 15 to 20 nt, 20 to 30 nt, 20 to 25 nt, or 25 to 30 nt). In some cases, a linear DNA molecule (double or single stranded) of a non-homologous DNA composition includes a stretch of nucleotides having 100% sequence identity with nucleotides at or near the target site of the genome and the stretch of nucleotides has a length in a range of from 2 to 30 nucleotides (nt) (e.g., 2 to 25 nt, 2 to 20 nt, 2 to 15 nt, 2 to 10 nt, 3 to 30 nt, 3 to 25 nt, 3 to 20 nt, 3 to 15 nt, 3 to 10 nt, 5 to 30 nt, 5 to 25 nt, 5 to 20 nt, 5 to 15 nt, 5 to 10 nt, 10 to 30 nt, 10 to 25 nt, 10 to 20 nt, 10 to 15 nt, 15 to 30 nt, 15 to 25 nt, 15 to 20 nt, 20 to 30 nt, 20 to 25 nt, or 25 to 30 nt).

"Linear"

A linearized non-homologous DNA composition includes DNA that is linear. It is recognized that in some cases, a small portion of the DNA molecules may circularize, or that a subject linearized non-homologous DNA composition might include a small portion of contaminating circularized DNA molecules. A substantial portion of the DNA of a linearized non-homologous DNA composition is linearized (i.e., non-circular, i.e., the DNA molecules have free 5' and 3' ends). In some cases, less than 10% (e.g., less than 8%, 6%, 5%, 4%, 3%, 2%, 1%, or 0.5%) of the DNA of a subject linearized non-homologous DNA composition is circular DNA. In some cases, less than 3% (e.g., less than 2%, 1%, or 0.5%) of the DNA of a subject linearized non-homologous DNA composition is circular DNA. In some cases, a subject linearized non-homologous DNA composition is substantially free of circular DNA. By substantially free is meant 0.5% or less of the DNA of a subject linearized non-homologous DNA composition is circular. In some case, none of the DNA of a subject linearized non-homologous DNA composition is circular.

In some cases, 90% or more (e.g., 92% or more, 93% or more, 94% or more, 95% or more, 96% or more, 97% or more, 98% or more, 99% or more, 99.5% or more, or 100%) of the DNA of a subject linearized non-homologous DNA composition is linear. In some cases, 95% or more (e.g., 96% or more, 97% or more, 98% or more, 99% or more, 99.5% or more, or 100%) of the DNA of a subject linearized non-homologous DNA composition is linear. In some cases, substantially all of the DNA of a subject linearized non-homologous DNA composition is linear. By substantially all is meant that 99.5% or more of the DNA of a subject linearized non-homologous DNA composition is linear. In some cases, 100% of the DNA of a subject linearized non-homologous DNA composition is linear.

In some cases, 90% or more (e.g., 92% or more, 93% or more, 94% or more, 95% or more, 96% or more, 97% or more, 98% or more, 99% or more, 99.5% or more, or 100%) of the DNA of a subject linearized non-homologous DNA composition has free 5' and 3' ends. In some cases, 95% or more (e.g., 96% or more, 97% or more, 98% or more, 99% or more, 99.5% or more, or 100%) of the DNA of a subject linearized non-homologous DNA composition has free 5' and 3' ends. In some cases, substantially all of the DNA of a subject linearized non-homologous DNA composition has free 5' and 3' ends. By substantially all is meant that 99.5% or more of the DNA of a subject linearized non-homologous DNA composition has free 5' and 3' ends. In some cases, 100% of the DNA of a subject linearized non-homologous DNA composition has free 5' and 3' ends.

In some cases, 90% or more (e.g., 92% or more, 93% or more, 94% or more, 95% or more, 96% or more, 97% or more, 98% or more, 99% or more, 99.5% or more, or 100%) of the DNA of a subject linearized non-homologous DNA composition has a free 5' end. In some cases, 95% or more (e.g., 96% or more, 97% or more, 98% or more, 99% or more, 99.5% or more, or 100%) of the DNA of a subject linearized non-homologous DNA composition has a free 5' end. In some cases, substantially all of the DNA of a subject linearized non-homologous DNA composition has a free 5' end. By substantially all is meant that 99.5% or more of the DNA of a subject linearized non-homologous DNA composition has a free 5' end. In some cases, 100% of the DNA of a subject linearized non-homologous DNA composition has a free 5' end.

In some cases, 90% or more (e.g., 92% or more, 93% or more, 94% or more, 95% or more, 96% or more, 97% or more, 98% or more, 99% or more, 99.5% or more, or 100%) of the DNA of a subject linearized non-homologous DNA composition has a free 3' end. In some cases, 95% or more (e.g., 96% or more, 97% or more, 98% or more, 99% or more, 99.5% or more, or 100%) of the DNA of a subject linearized non-homologous DNA composition has a free 3' end. In some cases, substantially all of the DNA of a subject linearized non-homologous DNA composition has a free 3' end. By substantially all is meant that 99.5% or more of the DNA of a subject linearized non-homologous DNA composition has a free 3' end. In some cases, 100% of the DNA of a subject linearized non-homologous DNA composition has a free 3' end.

Genome Targeting Composition

A genome targeting composition is a composition that includes a genome editing nuclease that is (or can be) targeted to a desired sequence within a target genome. A genome editing nuclease is an endonuclease capable of cleaving the phosphodiester bond within a polynucleotide chain at a designated specific site within a selected genomic target DNA (e.g., causing a double-stranded break (DSB)) without damaging the bases. In some embodiments, the genome editing nuclease binds a native or endogenous recognition sequence. In some embodiments, the genome editing nuclease is a modified endonuclease that binds a non-native or exogenous recognition sequence and does not bind a native or endogenous recognition sequence.

Examples of suitable genome editing nucleases include but are not limited to zinc finger nucleases, TAL-effector DNA binding domain-nuclease fusion proteins (transcription activator-like effector nucleases (TALENs)), and CRISPR/Cas endonucleases (e.g., class 2 CRISPR/Cas endonucleases such as a type II, type V, or type VI CRISPR/Cas endonucleases). Thus, in some embodiments, a genome targeting composition can include one or more genome editing nucleases selected from: a zinc finger nuclease, a TAL-effector DNA binding domain-nuclease fusion protein (TALEN), and a CRISPR/Cas endonuclease (e.g., a class 2 CRISPR/Cas endonuclease such as a type II, type V, or type VI CRISPR/Cas endonuclease). In some cases, a genome targeting composition includes a zinc finger nuclease or a TALEN. In some cases, a genome targeting composition includes a class 2 CRISPR/Cas endonuclease. In some cases, a genome targeting composition includes a class 2 type II CRISPR/Cas endonuclease (e.g., a Cas9 protein). In some cases, a genome targeting composition includes a class 2 type V CRISPR/Cas endonuclease (e.g., a Cpf1 protein, a C2c1 protein, or a C2c3 protein). In some cases, a genome targeting composition includes a class 2 type VI CRISPR/Cas endonuclease (e.g., a C2c2 protein).

As described in more detail below, a CRISPR/Cas endonuclease interacts with (binds to) a corresponding guide RNA to form a ribonucleoprotein (RNP) complex that is targeted to a particular site in a target genome via base pairing between the guide RNA and a target sequence within the target genome. A guide RNA includes a nucleotide sequence (a guide sequence) that is complementary to a sequence (the target site) of a target nucleic acid. Thus, when a subject genome targeting composition includes a CRISPR/Cas endonuclease (e.g., a class 2 CRISPR/Cas endonuclease), it must also include a corresponding guide RNA when being used in a method to cleave a target DNA. However, because the guide RNA can be readily modified in order to target any desired sequence within a target genome, in some cases, a composition includes only the CRISPR/Cas endonuclease (or a nucleic acid encoding the CRISPR/Cas endonuclease) until a user adds the desired corresponding guide RNA (or a nucleic acid encoding the corresponding guide RNA).

The components of a subject genome targeting composition can be delivered (introduced into a cell) as DNA, RNA, or protein. For example, when the composition includes a class 2 CRISPR/Cas endonuclease (e.g., Cas9, Cpf1, etc.) and a corresponding guide RNA (e.g., a Cas9 guide RNA, a Cpf1 guide RNA, etc.), the endonuclease and guide RNA can be delivered (introduced into the cell) as an RNP complex (i.e., a pre-assembled complex of the CRISPR/Cas endonuclease and the corresponding CRISPR/Cas guide RNA). Thus, a class 2 CRISPR/Cas endonuclease can be introduced into a cell as a protein. Alternatively, a class 2 CRISPR/Cas endonuclease can be introduced into a cell as a nucleic acid (DNA and/or RNA) encoding the endonuclease. A CRISPR/Cas guide RNA can be introduced into a cell as RNA, or as DNA encoding the guide RNA. Likewise, a zinc finger nuclease and/or a TALEN can be introduced into a cell as a protein or alternatively as a nucleic acid (DNA and/or RNA) encoding the protein.

In some cases, a genome editing nuclease is a fusion protein that is fused to a heterologous polypeptide (also referred to as a “fusion partner”). In some cases, a genome editing nuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.). In some embodiments, a genome editing nuclease is fused to an amino acid sequence (a fusion partner) that provides a tag (i.e., the fusion partner is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the fusion partner can provide for increased or decreased stability (i.e., the fusion partner can be a stability control peptide, e.g., a degron, which in some cases is controllable (e.g., a temperature sensitive or drug controllable degron sequence).

In some cases, a genome editing nuclease is conjugated (e.g., fused) to a polypeptide permeant domain to promote uptake by the cell (i.e., the fusion partner promotes uptake by a cell). A number of permeant domains are known in the art and may be used, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 1080). As another example, the permeant peptide can comprise the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4 (2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site can be determined by routine experimentation.

In some cases, a genome editing nuclease includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., a genome editing nuclease, e.g., a Cas9 protein). In some embodiments, a PTD is covalently linked to the carboxyl terminus of a polypeptide (e.g., a genome editing nuclease, e.g., a Cas9 protein). In some cases, the PTD is inserted internally in the genome editing nuclease (e.g., Cas9 protein) (i.e., is not at the N- or C-terminus of the genome editing nuclease). In some cases, a subject genome editing nuclease (e.g., Cas9 protein) includes (is conjugated to, is fused to) one or more PTDs (e.g., two or more, three or more, four or more PTDs). In some cases a PTD includes a nuclear localization signal (NLS) (e.g., in some cases 2 or more, 3 or more, 4 or more, or 5 or more NLSs).

In some cases, a genome editing nuclease (e.g., Cas9 protein) includes one or more NLSs (e.g., 2 or more, 3 or more, 4 or more, or 5 or more NLSs). In some embodiments, a PTD is covalently linked to a nucleic acid (e.g., a CRISPR/Cas guide RNA, a polynucleotide encoding a CRISPR/Cas guide RNA, a polynucleotide encoding a class 2 CRISPR/Cas endonuclease such as a Cas9 protein or a type V or type VI CRISPR/Cas protein, etc.). Examples of PTDs include but are not limited to a minimal undecapeptide protein transduction domain (corresponding to residues 47-57 of HIV-1 TAT comprising YGRKKRRQRRR; SEQ ID NO:1076); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:1077); Transportan GWTLNSAGYLLGKINLKALAALAKKIL (SEQ ID NO:1078); KALAWEAKLAKALAKALAKHLAKALAKALKCEA (SEQ ID NO:1079); and RQIKIWFQNRRMKWKK (SEQ ID NO:1080). Exemplary PTDs include but are not limited to, YGRKKRRQRRR (SEQ ID NO:1081), RKKRRQRRR (SEQ ID NO:1082); an arginine homopolymer of from 3 arginine residues to 50 arginine residues; Exemplary PTD domain amino acid sequences include, but are not limited to, any of the following: YGRKKRRQRRR (SEQ ID NO:1083); RKKRRQRR (SEQ ID NO:1084); YARAAARQARA (SEQ ID NO:1085); THRLPRRRRRR (SEQ ID NO:1086); and GGRRARRRRRR (SEQ ID NO:1087). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

A genome editing nuclease (e.g., Cas9 protein) can have multiple (1 or more, 2 or more, 3 or more, etc.) fusion partners in any combination of the above. As an illustrative example, a genome editing nuclease (e.g., Cas9 protein) can have a fusion partner that provides for tagging (e.g., GFP), and can also have a subcellular localization sequence (e.g., one or more NLSs). In some cases, such a fusion protein might also have a tag for ease of tracking and/or purification (e.g., a histidine tag, e.g., a 6×His tag; a hemagglutinin (HA) tag; a FLAG tag; a Myc tag; and the like). As another illustrative example, genome editing nuclease (e.g., Cas9 protein) can have one or more NLSs (e.g., two or more, three or more, four or more, five or more, 1, 2, 3, 4, or 5 NLSs). In some cases a fusion partner (or multiple fusion partners, e.g., 1, 2, 3, 4, or 5 fusion partners; e.g., an NLS, a tag, a fusion partner providing an activity, etc.) is located at or near the C-terminus of the genome editing nuclease (e.g., Cas9 protein). In some cases a fusion partner (or multiple fusion partners, e.g., 1, 2, 3, 4, or 5 fusion partners; e.g., an NLS, a tag, a fusion partner providing an activity, etc.) is located at the N-terminus of the genome editing nuclease (e.g., Cas9 protein). In some cases the genome editing nuclease (e.g., Cas9 protein) has a fusion partner (or multiple fusion partners, e.g., 1, 2, 3, 4, or 5 fusion partners; e.g., an NLS, a tag, a fusion partner providing an activity, etc.) at both the N-terminus and C-terminus.

Zinc Finger Nucleases (ZFNs)

In some embodiments, a subject genome editing nuclease is a zinc-finger nuclease (ZFN). ZFNs are engineered double-strand break inducing proteins comprised of a zinc finger DNA binding domain and a double strand break inducing agent domain Engineered ZFNs consist of two zinc finger arrays (ZFAs), each of which is fused to a single subunit of a non-specific endonuclease, such as the nuclease domain from the FokI enzyme, which becomes active upon dimerization. Typically, a single ZFA consists of 3 or 4 zinc finger domains, each of which is designed to recognize a specific nucleotide triplet (GGC, GAT, etc.). Thus, ZFNs composed of two "3-finger" ZFAs are capable of recognizing an 18 base pair target site; an 18 base pair recognition sequence is generally unique, even within large genomes such as those of humans and plants. By directing the co-localization and dimerization of two FokI nuclease monomers, ZFNs generate a functional site-specific endonuclease that creates a double-stranded break (DSB) in DNA at the targeted locus.

Useful zinc-finger nucleases include those that are known and those that are engineered to have specificity for one or more desired target sites (TS). Zinc finger domains are amenable for designing polypeptides which specifically bind a selected polynucleotide recognition sequence, for example, within the target site of the host cell genome. ZFNs consist of an engineered DNA-binding zinc finger domain linked to a non-specific endonuclease domain, for example nuclease domain from a Type Hs endonuclease such as HO or FokI. Alternatively, engineered zinc finger DNA binding domains can be fused to other double-strand break inducing agents or derivatives thereof that retain DNA nicking/cleaving activity. For example, this type of fusion can be used to direct the double-strand break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, or a derivative thereof that retains DNA nicking and/or cleaving activity. Additional functionalities can be fused to the zinc-finger binding domain, including transcriptional activator domains, transcription repressor domains, and methylases. In some embodiments, dimerization of nuclease domain is required for cleavage activity.

Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. Useful designer zinc finger modules include those that recognize various GNN and ANN triplets (Dreier, et al., (2001) J Biol Chem 276:29466-78; Dreier, et al., (2000) J Mol Biol 303:489-502; Liu, et al., (2002) J Biol Chem 277:3850-6), as well as those that recognize various CNN or TNN triplets (Dreier, et al., (2005) J Biol Chem 280:35588-97; Jamieson, et al., (2003) Nature Rev Drug Discov 2:361-8). See also, Durai, et al., (2005) Nucleic Acids Res 33:5978-90; Segal, (2002) Methods 26:76-83; Porteus and Carroll, (2005) Nat Biotechnol 23:967-73; Pabo, et al., (2001) Ann Rev Biochem 70:313-40; Wolfe, et al., (2000) Ann Rev Biophys Biomol Struct 29:183-212; Segal and Barbas, (2001) Curr Opin Biotechnol 12:632-7; Segal, et al., (2003) Biochemistry 42:2137-48; Beerli and Barbas, (2002) Nat Biotechnol 20:135-41; Carroll, et al., (2006) Nature Protocols 1:1329; Ordiz, et al., (2002) Proc Natl Acad Sci USA 99:13290-5; Guan, et al., (2002) Proc Natl Acad Sci USA 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242. Useful zinc-finger nucleases also include those described in WO03/080809; WO05/014791; WO05/084190; WO08/021207; WO09/042186; WO09/054985; and WO10/065123.

If the genome editing endonuclease to be utilized is a zinc finger nuclease, optimal target sites may be selected using a number of publicly available online resources. See, e.g., Reyon et al., BMC Genomics 12:83 (2011), which is hereby incorporated by reference in its entirety. For example, Oligomerized Pool Engineering (OPEN) is a highly robust and publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a pre-constructed randomized pool of candidate ZFAs is screened to identify those with high affinity and specificity for a desired target sequence. ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome currently includes a total of more than 11.6 million potential ZFN target sites, mapped within the fully sequenced genomes of seven model organisms; *Saccharomyces cerevisiae, Chlamydomonas reinhardtii, Arabidopsis thaliana, Drosophila melanogaster, Danio rerio, Caenorhabditis elegans*, and *Homo sapiens*. Additional model organisms, including three plant species; *Glycine max* (soybean), *Oryza sativa* (rice), *Zea mays* (maize), and three animal species *Tribolium castaneum* (red flour beetle), *Mus musculus* (mouse), *Rattus norvegicus* (brown rat) can also be used. ZFNGenome provides information about each potential ZFN target site, including its chromosomal location and position relative to transcription initiation site(s). Users can query ZFNGenome using several different criteria (e.g., gene ID, transcript ID, target site sequence).

For more information on ZFNs, refer to U.S. Pat. No. 8,685,737, which is hereby incorporated by reference in its entirety.

TALENs

In some embodiments, a subject genome editing nuclease is a TAL-effector DNA binding domain-nuclease fusion protein (TALEN). A TAL effector comprises a DNA binding domain that interacts with DNA in a sequence-specific manner through one or more tandem repeat domains. The repeated sequence typically comprises 34 amino acids, and the repeats are typically 91-100% homologous with each other. Polymorphism of the repeats is usually located at positions 12 and 13, and there appears to be a one-to-one correspondence between the identity of repeat variable-diresidues at positions 12 and 13 with the identity of the contiguous nucleotides in the TAL-effector's target sequence.

The TAL-effector DNA binding domain can be engineered to bind to a desired target sequence, and fused to a nuclease domain, e.g., from a type II restriction endonuclease, typically a nonspecific cleavage domain from a type II restriction endonuclease such as Fold (see e.g., Kim et al. (1996) Proc. Natl. Acad. Sci. USA 93:1156-1160). Other useful endonucleases may include, for example, HhaI, HindIII, Nod, BbvCI, EcoRI, BglI, and AlwI. Thus, in some embodiments, a TALEN comprises a TAL effector domain comprising a plurality of TAL effector repeat sequences that, in combination, bind to a specific nucleotide sequence in the target DNA sequence, such that the TALEN cleaves the target DNA within or adjacent to the specific nucleotide sequence. Suitable TALENs include those described in WO10/079430 and U.S. Patent Application Publication No. 2011/0145940.

In some embodiments, the TAL effector domain that binds to a specific nucleotide sequence within the target DNA can comprise 10 or more DNA binding repeats, and in some cases 15 or more DNA binding repeats. In some embodiments, each DNA binding repeat comprises a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

If the genome editing endonuclease to be utilized is a TALEN, in some embodiments, optimal target sites may be selected in accordance with the methods described by Sanjana et al., Nature Protocols, 7:171-192 (2012), which is hereby incorporated by reference in its entirety. In brief, TALENs function as dimers, and a pair of TALENs, referred to as the left and right TALENs, target sequences on opposite strands of DNA. TALENs can be engineered as a fusion of the TALE DNA-binding domain and a monomeric Fold catalytic domain. To facilitate FokI dimerization, the left and right TALEN target sites can be chosen with a spacing of approximately 14-20 bases. Therefore, for a pair of TALENs, each targeting 20-bp sequences, an optimal target site can have the form 5'-$TN^{19}N^{14-20}N^{19}A$-3', where the left TALEN targets 5'-$TN^{19}$-3' and the right TALEN targets the antisense strand of 5'-$N^{19}A$-3' (N=A, G, T or C).

For more information on TALENs, refer to U.S. Pat. No. 8,685,737, which is hereby incorporated by reference in its entirety.

Class 2 CRISPR/Cas Endonucleases

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In some embodiments, a genome editing nuclease of a genome targeting composition of the present disclosure is a class 2 CRISPR/Cas endonuclease. Thus in some cases, a subject genome targeting composition includes a class 2 CRISPR/Cas endonuclease (or a nucleic encoding the endonuclease). In class 2 CRISPR systems, the functions of the effector complex (e.g., the cleavage of target DNA) are carried out by a single endonuclease (e.g., see Zetsche et al, Cell. 2015 Oct. 22; 163(3):759-71; Makarova et al, Nat Rev Microbiol. 2015 November; 13 (11):722-36; and Shmakov et al., Mol Cell. 2015 Nov. 5; 60(3):385-97). As such, the term "class 2 CRISPR/Cas protein" is used herein to encompass the endonuclease (the target nucleic acid cleaving protein) from class 2 CRISPR systems. Thus, the term "class 2 CRISPR/Cas endonuclease" as used herein encompasses type II CRISPR/Cas proteins (e.g., Cas9), type V CRISPR/Cas proteins (e.g., Cpf1, C2c1, C2C3), and type VI CRISPR/Cas proteins (e.g., C2c2). To date, class 2 CRISPR/Cas proteins encompass type II, type V, and type VI CRISPR/Cas proteins, but the term is also meant to encompass any class 2 CRISPR/Cas protein suitable for binding to a corresponding guide RNA and forming an RNP complex.

Type II CRISPR/Cas Endonucleases (e.g., Cas 9)

In natural Type II CRISPR/Cas systems, Cas9 functions as an RNA-guided endonuclease that uses a dual-guide RNA having a crRNA and trans-activating crRNA (tracrRNA) for target recognition and cleavage by a mechanism involving two nuclease active sites in Cas9 that together generate double-stranded DNA breaks (DSBs), or can individually generate single-stranded DNA breaks (SSBs). The Type II CRISPR endonuclease Cas9 and engineered dual-(dgRNA) or single guide RNA (sgRNA) form a ribonucleoprotein (RNP) complex that can be targeted to a desired DNA sequence. Guided by a dual-RNA complex or a chimeric single-guide RNA, Cas9 generates site-specific DSBs or SSBs within double-stranded DNA (dsDNA) target nucleic acids, which are repaired either by non-homologous end joining (NHEJ) or homology-directed recombination (HDR).

As noted above, in some cases, a genome targeting composition of the present disclosure includes a type II CRISPR/Cas endonuclease. A type II CRISPR/Cas endonuclease is a type of class 2 CRISPR/Cas endonuclease. In some cases, the type II CRISPR/Cas endonuclease is a Cas9 protein. A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 5-816. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein is a fusion protein comprising a Cas9 polypeptide that is fused to a heterologous protein (referred to as a fusion partner), where the heterologous protein provides an activity (e.g., one that is not provided by the Cas9 protein). The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive, or has reduced enzymatic activity relative to a wild-type Cas9 protein (e.g., relative to Streptococcus pyogenes Cas9).

Assays to determine whether given protein interacts with a Cas9 guide RNA can be any convenient binding assay that tests for binding between a protein and a nucleic acid. Suitable binding assays (e.g., gel shift assays) will be known to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

In some cases, a chimeric Cas9 protein includes a heterologous polypeptide that has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other cases, a chimeric Cas9 protein includes a heterologous polypeptide that has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologs from a wide variety of species have been identified and in some cases the proteins share only a few identical amino acids. Identified Cas9 orthologs have similar domain architecture with a central HNH endonuclease domain and a split RuvC/RNaseH domain (e.g., RuvCI, RuvCII, and RuvCIII) (e.g., see Table 1). For example, a Cas9 protein can have 3 different regions (sometimes referred to as RuvC-I, RuvC-II, and RucC-III), that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 1 may not represent the entire RuvC-like and/or HNH domains as accepted in the art, but Table 1 does present motifs that can be used to help determine whether a given protein is a Cas9 protein.

TABLE 1

Table 1 lists 4 motifs that are present in Cas9 sequences from various species. The amino acids listed in Table 1 are from the Cas9 from *S. pyogenes* (SEQ ID NO: 5).

| Motif # | Motif | Amino acids (residue #s) | Highly conserved |
|---|---|---|---|
| 1 | RuvC-like I | IGLDIGTNSVGWAV I (7-21) (SEQ ID NO: 1) | D10, G12, G17 |
| 2 | RuvC-like II | IVIEMARE (759-766) (SEQ ID NO: 2) | E762 |
| 3 | HNH-motif | DVDHIVPQSFLKDD SIDNKVLTRSDKN (837-863) (SEQ ID NO: 3) | H840, N854, N863 |
| 4 | RuvC-like III | HHAHDAYL (982-989) (SEQ ID NO: 4) | H982, H983, A984, D986, A987 |

In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 1-4, respectively (e.g., see Table 1), or to the corresponding portions in any of the amino acid sequences set forth in SEQ ID NOs: 5-816.

In other words, in some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, and are set forth as SEQ ID NOs:

1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 5, or to any of the amino acid sequences set forth as SEQ ID NOs: 6-816.

In some cases, a suitable Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs:1-4), or to the corresponding portions in any of the amino acid sequences set forth as SEQ ID NOs: 6-816.

As used herein, the term "Cas9 protein" encompasses a "chimeric Cas9 protein." As used herein, the term "Cas9 protein" encompasses a variant Cas9 that is a nickase. As used herein, the term "Cas9 protein" encompasses a variant Cas9 that exhibits reduced enzymatic activity (e.g., a "dead Cas9" or "dCas9").

Variant Cas9 Proteins—Nickases and dCas9

In some cases, a Cas9 protein is a variant Cas9 protein. A variant Cas9 protein has an amino acid sequence that is different by at least one amino acid (e.g., has a deletion, insertion, substitution, fusion) when compared to the amino acid sequence of a corresponding wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. In some cases, the variant Cas9 protein has no substantial nuclease activity. When a Cas9 protein is a variant Cas9 protein that has no substantial nuclease activity, it can be referred to as "dCas9." A protein (e.g., a class 2 CRISPR/Cas protein, e.g., a Cas9 protein) that cleaves one strand but not the other of a double stranded target nucleic acid is referred to herein as a "nickase" (e.g., a "nickase Cas9").

In some cases, a variant Cas9 protein can cleave the complementary strand (sometimes referred to in the art as the target strand) of a target nucleic acid but has reduced ability to cleave the non-complementary strand (sometimes referred to in the art as the non-target strand) of a target nucleic acid. For example, the variant Cas9 protein can have a mutation (amino acid substitution) that reduces the function of the RuvC domain. Thus, the Cas9 protein can be a nickase that cleaves the complementary strand, but does not cleave the non-complementary strand. As a non-limiting example, in some embodiments, a variant Cas9 protein has a mutation at an amino acid position corresponding to residue D10 (e.g., D10A, aspartate to alanine) of SEQ ID NO: 5 (or the corresponding position of any of the proteins set forth in SEQ ID NOs: 6-261 and 264-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). See, e.g., SEQ ID NO: 262.

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain Thus, the Cas9 protein can be a nickase that cleaves the non-complementary strand, but does not cleave the complementary strand. As a non-limiting example, in some embodiments, the variant Cas9 protein has a mutation at an amino acid position corresponding to residue H840 (e.g., an H840A mutation, histidine to alanine) of SEQ ID NO: 5 (or the corresponding position of any of the proteins set forth as SEQ ID NOs: 6-261 and 264-816) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid). See, e.g., SEQ ID NO: 263.

In some cases, a variant Cas9 protein has a reduced ability to cleave both the complementary and the non-complementary strands of a double stranded target nucleic acid. As a non-limiting example, in some cases, the variant Cas9 protein harbors mutations at amino acid positions corresponding to residues D10 and H840 (e.g., D10A and H840A) of SEQ ID NO: 5 (or the corresponding residues of any of the proteins set forth as SEQ ID NOs: 6-261 and 264-816) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "dead" Cas9 or simply "dCas9." See, e.g., SEQ ID NO: 264.

Other residues can be mutated to achieve the above effects (i.e. inactivate one or the other nuclease portions). As non-limiting examples, residues D10, G12, G17, E762, H840, N854, N863, H982, H983, A984, D986, and/or A987 of SEQ ID NO: 5 (or the corresponding mutations of any of the proteins set forth as SEQ ID NOs: 6-816) can be altered (i.e., substituted). Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or a A987 mutation of SEQ ID NO: 5 or the corresponding mutations of any of the proteins set forth as SEQ ID NOs: 6-816, e.g., D10A, G12A, G17A, E762A, H840A, N854A, N863A, H982A, H983A, A984A, and/or D986A), the variant Cas9 protein can still bind to target nucleic acid in a site-specific manner (because it is still guided to a target nucleic acid sequence by a Cas9 guide RNA) as long as it retains the ability to interact with the Cas9 guide RNA.

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816.

Type V and Type VI CRISPR/Cas Endonucleases

In some cases, a genome targeting composition of the present disclosure includes a type V or type VI CRISPR/Cas endonuclease (i.e., the genome editing endonuclease is a type V or type VI CRISPR/Cas endonuclease) (e.g., Cpf1, C2c1, C2c2, C2c3). Type V and type VI CRISPR/Cas endonucleases are a type of class 2 CRISPR/Cas endonucelase. Examples of type V CRISPR/Cas endonucleases include but are not limited to: Cpf1, C2c1, and C2c3. An example of a type VI CRISPR/Cas endonuclease is C2c2. In some cases, a subject genome targeting composition includes a type V CRISPR/Cas endonuclease (e.g., Cpf1, C2c1, C2c3). In some cases, a Type V CRISPR/Cas endonuclease is a Cpf1 protein. In some cases, a subject genome targeting composition includes a type VI CRISPR/Cas endonuclease (e.g., C2c2).

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the guide RNA.

Examples and guidance related to type V and type VI CRISPR/Cas proteins (e.g., cpf1, C2c1, C2c2, and C2c3 guide RNAs) can be found in the art, for example, see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97.

In some cases, the Type V or type VI CRISPR/Cas endonuclease (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases a type V CRISPR/Cas endonuclease is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the Cpf1 amino acid sequence set forth in any of SEQ ID NOs: 1088-1092.

In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the Cpf1 amino acid sequence set forth in any of SEQ ID NOs: 1088-1092.

In some cases, the Cpf1 protein exhibits reduced enzymatic activity relative to a wild-type Cpf1 protein (e.g., relative to a Cpf1 protein comprising the amino acid sequence set forth in any of SEQ ID NOs: 1088-1092), and retains DNA binding activity. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., a D→A substitution) at an amino acid residue corresponding to amino acid 917 of the Cpf1 amino acid sequence set forth in SEQ ID NO: 1088. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., an E→A substitution) at an amino acid residue corresponding to amino acid 1006 of the Cpf1 amino acid sequence set forth in SEQ ID NO: 1088. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., a D→A substitution) at an amino acid residue corresponding to amino acid 1255 of the Cpf1 amino acid sequence set forth in SEQ ID NO: 1088.

In some cases, a suitable Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092.

In some cases a type V CRISPR/Cas endonuclease is a C2c1 protein (examples include those set forth as SEQ ID NOs: 1112-1119). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c1 amino acid sequence set forth in any of SEQ ID NOs: 1112-1119.

In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c1 amino acid sequences set forth in any of SEQ ID NOs: 1112-1119). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c1 amino acid sequence set forth in any of SEQ ID NOs: 1112-1119.

In some cases, the C2c1 protein exhibits reduced enzymatic activity relative to a wild-type C2c1 protein (e.g., relative to a C2c1 protein comprising the amino acid sequence set forth in any of SEQ ID NOs: 1112-1119), and retains DNA binding activity. In some cases, a suitable C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 1112-1119.

In some cases a type V CRISPR/Cas endonuclease is a C2c3 protein (examples include those set forth as SEQ ID NOs: 1120-1123). In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c3 amino acid sequence set forth in any of SEQ ID NOs: 1120-1123.

In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c3 amino acid sequence set forth in any of SEQ ID NOs: 1120-1123.

In some cases, the C2c3 protein exhibits reduced enzymatic activity relative to a wild-type C2c3 protein (e.g., relative to a C2c3 protein comprising the amino acid sequence set forth in any of SEQ ID NOs: 1120-1123), and retains DNA binding activity. In some cases, a suitable C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 1120-1123.

In some cases a type VI CRISPR/Cas endonuclease is a C2c2 protein (examples include those set forth as SEQ ID NOs: 1124-1135). In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c2 amino acid sequence set forth in any of SEQ ID NOs: 1124-1135.

In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c2 amino acid sequence set forth in any of SEQ ID NOs: 1124-1135.

In some cases, the C2c2 protein exhibits reduced enzymatic activity relative to a wild-type C2c2 protein (e.g., relative to a C2c2 protein comprising the amino acid sequence set forth in any of SEQ ID NOs: 1124-1135), and retains DNA binding activity. In some cases, a suitable C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 1124-1135.

Guide RNA (for CRISPR/Cas Endonucleases)

A nucleic acid molecule that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA."

A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

A guide RNA can be referred to by the protein to which it corresponds. For example, when the class 2 CRISPR/Cas endonuclease is a Cas9 protein, the corresponding guide RNA can be referred to as a "Cas9 guide RNA." Likewise, as another example, when the class 2 CRISPR/Cas endonuclease is a Cpf1 protein, the corresponding guide RNA can be referred to as a "Cpf1 guide RNA."

In some embodiments, a guide RNA includes two separate nucleic acid molecules: an "activator" and a "targeter" and is referred to herein as a "dual guide RNA", a "double-molecule guide RNA", a "two-molecule guide RNA", or a "dgRNA." In some embodiments, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Cas9 Guide RNA

A nucleic acid molecule that binds to a Cas9 protein and targets the complex to a specific location within a target nucleic acid is referred to herein as a "Cas9 guide RNA."

A Cas9 guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid.

A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein to any desired sequence of any desired target nucleic acid, with the exception that the protospacer adjacent motif (PAM) sequence can be taken into account. Thus, for example, a Cas9 guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

A Cas9 guide RNA (e.g. a dual guide RNA or a single guide RNA) can be comprised of any corresponding activator and targeter pair. Non-limiting examples of nucleotide sequences that can be included in a Cas9 guide RNA (dgRNA or sgRNA) include sequences set forth in SEQ ID NOs: 827-1075, or complements thereof. For example, in some cases, sequences from SEQ ID NOs: 827-957 (which are from tracrRNAs) or complements thereof, can pair with sequences from SEQ ID NOs: 964-1075 (which are from crRNAs), or complements thereof, to form a dsRNA duplex of a protein binding segment.

Targeting Segment of a Cas9 Guide RNA

The first segment of a subject guide nucleic acid includes a guide sequence (i.e., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Examples of various Cas9 proteins and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al., Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Guide RNAs Corresponding to Type V and Type VI CRISPR/Cas Endonucleases (e.g., Cpf1 Guide RNA)

A guide RNA that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

A type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt,).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex).

The target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

The guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

The guide sequence of a type V or type VI CRISPR/Cas guide RNA (e.g., cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotides and 23 complementary nucleotides with the target nucleic acid sequence.

The duplex-forming segment of a type V or type VI CRISPR/Cas guide RNA (e.g., cpf1 guide RNA) (e.g., of a targeter RNA or an activator RNA) can have a length of from 15 nt to 25 nt (e.g., 15 nt, 16 nt, 17 nt, 18 nt, 19 nt, 20 nt, 21 nt, 22 nt, 23 nt, 24 nt, or 25 nt).

The RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 15 bp, 9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an example, a duplex-forming segment of a Cpf1 guide RNA can comprise a nucleotide sequence selected from (5' to 3'): AAUUUCUACUGUUGUAGAU (SEQ ID NO: 1093), AAUUUCUGCUGUUGCAGAU (SEQ ID NO: 1094), AAUUUCCACUGUUGUGGAU (SEQ ID NO: 1095), AAUUCCUACUGUUGUAGGU (SEQ ID NO: 1096), AAUUUCUACUAUUGUAGAU (SEQ ID NO: 1097), AAUUUCUACUGCUGUAGAU (SEQ ID NO: 1098), AAUUUCUACUUUGUAGAU (SEQ ID NO: 1099), and AAUUUCUACUUGUAGAU (SEQ ID NO: 1100). The guide sequence can then follow (5' to 3') the duplex forming segment.

A non-limiting example of an activator RNA (e.g. tracrRNA) of a C2c1 guide RNA (dual guide or single guide) is an RNA that includes the nucleotide sequence GAAUUUUUCAACGGGUGUGCCAAUGGCCACUUUCCAGGUGGCAAAGCCCGUUGA GCUUCUCAAAAAG (SEQ ID NO: 1101). In some cases, a C2c1 guide RNA (dual guide or single guide) is an RNA that includes the nucleotide sequence In some cases, a C2c1 guide RNA (dual guide or single guide) is an RNA that includes the nucleotide sequence GUCUAGAGGACAGAAUUUUUCAACGGGUGUGCCAAUGGCCACUUUCCAGGUGGC AAAGCCCGUUGAGCUUCUCAAAAAG (SEQ ID NO: 1102). In some cases, a C2c1 guide RNA (dual guide or single guide) is an RNA that includes the nucleotide sequence UCUAGAGGACAGAAUUUUUCAACGGGUGUGCCAAUGGCCACUUUCCAGGUGGCA AAGCCCGUUGAGCUUCUCAAAAAG (SEQ ID NO: 1103). A non-limiting example of an activator RNA (e.g. tracrRNA) of a C2c1 guide RNA (dual guide or single guide) is an RNA that includes the nucleotide sequence ACUUUCCAGGCAAAGCCCGUUGAGCUUCUCAAAAAG (SEQ ID NO: 1104). In some cases, a duplex forming segment of a C2c1 guide RNA (dual guide or single guide) of an activator RNA (e.g. tracrRNA) includes the nucleotide sequence AGCUUCUCA (SEQ ID NO: 1105) or the nucleotide sequence GCUUCUCA (SEQ ID NO: 1106) (the duplex forming segment from a naturally existing tracrRNA.

A non-limiting example of a targeter RNA (e.g. crRNA) of a C2c1 guide RNA (dual guide or single guide) is an RNA with the nucleotide sequence CUGAGAAGUGGCACNNNNNNNNNNNNNNNNNNNN (SEQ ID NO: 1107), where the Ns represent the guide sequence, which will vary depending on the target sequence, and although 20 Ns are depicted a range of different lengths are acceptable. In some cases, a duplex forming segment of a C2c1 guide RNA (dual guide or single guide) of a targeter RNA (e.g. crRNA) includes the nucleotide sequence CUGAGAAGUGGCAC (SEQ ID NO: 1108) or includes the nucleotide sequence CUGAGAAGU (SEQ ID NO: 1109) or includes the nucleotide sequence UGAGAAGUGGCAC (SEQ ID NO: 1110) or includes the nucleotide sequence UGAGAAGU (SEQ ID NO: 1111).

Examples and guidance related to type V or type VI CRISPR/Cas endonucleases and guide RNAs (as well as information regarding requirements related to protospacer adjacent motif (PAM) sequences present in targeted nucleic acids) can be found in the art, for example, see Zetsche et al., Cell. 2015 Oct. 22; 163(3):759-71; Makarova et al., Nat Rev Microbiol. 2015 November; 13(11):722-36; and Shmakov et al., Mol Cell. 2015 Nov. 5; 60(3):385-97.

Target Cells

A target nucleic acid (e.g., target genomic DNA) can be located within a eukaryotic cell, for example, inside of a eukaryotic cell in vitro, inside of a eukaryotic cell in vivo, inside of a eukaryotic cell ex vivo. Suitable target cells (which can comprise target nucleic acids) include, but are not limited to: a single-celled eukaryotic organism; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell of an invertebrate animal (e.g. fruit fly, cnidarian, echinoderm, nematode, etc.); a cell of a vertebrate animal (e.g., fish, amphibian, reptile, bird, mammal); a cell of a mammal (e.g., a cell of a rodent such as a mouse or rat, a cell of a non-human primate, a cell of a human, etc.); and the like. Any type of cell may be of interest (e.g. a stem cell, e.g. an embryonic stem (ES) cell, an induced pluripotent stem (iPS) cell, a hematopoietic stem cell, a germ cell (e.g., an oocyte, a sperm, an oogonia, a spermatogonia, etc.), a somatic cell, e.g. a fibroblast, an oligodendrocyte, a glial cell, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

Target cells include in vivo target cells. Target cells include retinal cells (e.g., Müller cells, ganglion cells, amacrine cells, horizontal cells, bipolar cells, and photoreceptor cells including rods and cones, Müller glial cells, and retinal pigmented epithelium); neural cells (e.g., cells of the thalamus, sensory cortex, zona incerta (ZI), ventral tegmental area (VTA), prefontal cortex (PFC), nucleus accumbens (NAc), amygdala (BLA), substantia nigra, ventral pallidum, globus pallidus, dorsal striatum, ventral striatum, subthalamic nucleus, hippocampus, dentate gyrus, cingulate gyrus, entorhinal cortex, olfactory cortex, primary motor cortex, or cerebellum); liver cells; kidney cells; immune cells (e.g., T cells, B cells, and the like); cardiac cells; skeletal muscle cells; smooth muscle cells; lung cells; and the like.

Nucleic Acids

In some cases, a subject method or composition/kit includes a nucleic acid (RNA or DNA) encoding a genome editing endonuclease (e.g., a zinc finger nuclease, a TALEN, a class 2 CRISPR/Cas endonuclease, etc.) and/or a CRISPR/Cas guide RNA. In some cases, a subject method or composition/kit includes a DNA encoding a genome editing endonuclease (e.g., a zinc finger nuclease, a TALEN, a class 2 CRISPR/Cas endonuclease, etc.) and/or a DNA encoding a CRISPR/Cas guide RNA.

Many vectors, e.g. plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, etc.

Vectors may be provided directly to the subject cells. In other words, cells can be contacted with vectors comprising nucleic acid encoding a genome editing endonuclease (e.g., a zinc finger nuclease, a TALEN, a class 2 CRISPR/Cas endonuclease, etc.) and/or a CRISPR/Cas guide RNA such that the vectors are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising the nucleic acid. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also introduced by direct micro-injection (e.g., injection of RNA into a zebrafish embryo).

Vectors used for providing the nucleic acids encoding a genome editing endonuclease, e.g., a zinc finger nuclease, a TALEN, a class 2 CRISPR/Cas endonuclease, etc., and/or a CRISPR/Cas guide RNA to target cells can include suitable promoters for driving expression, that is, transcriptional activation, of the nucleic acid of interest. In other words, the nucleic acid of interest (a nucleotide sequence encoding a genome editing endonuclease, e.g., a zinc finger nuclease, a TALEN, a class 2 CRISPR/Cas endonuclease, etc., and/or a CRISPR/Cas guide RNA) can be operably linked to a promoter (e.g., a promoter operable in the target cell). This may include ubiquitously acting promoters, for example, the CMV-β-actin promoter, the EF-1 alpha promoter, and the like, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing a genome editing endonuclease, e.g., a zinc finger nuclease, a TALEN, a class 2 CRISPR/Cas endonuclease, etc., and/or a CRISPR/Cas guide RNA, to target cells may include nucleic acid sequences that encode for selectable markers in the target cells, so as to identify cells that have taken up the introduced nucleic acid.

As noted above, a genome editing endonuclease, e.g., a zinc finger nuclease, a TALEN, a class 2 CRISPR/Cas endonuclease, etc., and/or a CRISPR/Cas guide RNA may be introduced into cells as RNA. Methods of introducing RNA into cells are known in the art and may include, for example, direct injection, transfection, or any other method used for the introduction of DNA.

A genome editing endonuclease (e.g., a zinc finger nuclease, a TALEN, a class 2 CRISPR/Cas endonuclease such as a Cas9 protein, and the like) may be introduced into cells as a polypeptide (e.g., in some cases complexed with a guide RNA, thus forming an RNP). Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a genome editing endonuclease (e.g., a zinc finger nuclease, a TALEN, a class 2 CRISPR/Cas endonuclease such as a Cas9 protein, and the like) may be fused to a polypeptide permeant domain to promote uptake by the cell. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 1080). As another example, the permeant peptide comprises the HIV-1 tat basic region amino acid sequence, which may include, for example, amino acids 49-57 of naturally-occurring tat protein. Other permeant domains include polyarginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A genome editing endonuclease (e.g., a zinc finger nuclease, a TALEN, a class 2 CRISPR/Cas endonuclease such as a Cas9 protein, and the like) may be produced in vitro or by eukaryotic cells or by prokaryotic cells, and it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

A genome editing endonuclease (e.g., a zinc finger nuclease, a TALEN, a class 2 CRISPR/Cas endonuclease such as a Cas9 protein, and the like) may be isolated and purified, e.g., in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used can comprise at least 20% by weight of the desired product, more usually at least 75% by weight, e.g., at least 95% by weight, and for therapeutic purposes, e.g., at least 99.5% by weight, in relation to contaminants related to the method of preparation of the product and its purification. The percentages can be based upon total protein.

Methods and Administration (Introduction into a Cell)

In some embodiments, a subject method is a method of editing genomic DNA of a eukaryotic cell and the method includes introducing into a eukaryotic cell a composition comprising: (a) a linear non-homologous DNA composition comprising linear DNA (e.g., in an amount effective to enhance frequency of insertions and/or deletions (indels) within the genomic DNA), and (b) a genome targeting composition comprising: (i) a genome editing endonuclease, or (ii) a nucleic acid encoding the genome editing endonuclease, where the method results in modification of the genomic DNA (e.g., introduction of an indel into the genomic DNA). In some cases where the genome editing endonuclease is a class 2 CRISPR/Cas endonuclease (e.g., a Cas9 protein), the genome targeting composition includes a corresponding CRISPR/Cas guide RNA (e.g., a Cas9 guide RNA), or a nucleic acid encoding the CRISPR/Cas guide RNA.

In some cases, a subject method is a method of stimulating non-homologous end-joining in a eukaryotic cell and the method includes introducing into a eukaryotic cell a composition comprising: (a) a linear non-homologous DNA composition comprising linear DNA (e.g., in an amount effective to enhance frequency of insertions and/or deletions (indels) within the genomic DNA), and (b) a genome targeting composition comprising: (i) a genome editing endonuclease, or (ii) a nucleic acid encoding the genome editing endonuclease, where the method results in modification of the genomic DNA (e.g., introduction of an indel into the genomic DNA). In some cases where the genome editing endonuclease is a class 2 CRISPR/Cas endonuclease (e.g., a Cas9 protein), the genome targeting composition includes a corresponding CRISPR/Cas guide RNA (e.g., a Cas9 guide RNA), or a nucleic acid encoding the CRISPR/Cas guide RNA.

In some cases, a subject method is a method of enhancing the frequency of insertions and/or deletions (indels) during genome editing in a eukaryotic cell, and the method includes introducing into a eukaryotic cell a composition comprising: (a) a linear non-homologous DNA composition comprising linear DNA (e.g., in an amount effective to enhance frequency of insertions and/or deletions (indels) within the genomic DNA), and (b) a genome targeting composition comprising: (i) a genome editing endonuclease, or (ii) a nucleic acid encoding the genome editing endonuclease, where the method results in modification of the genomic DNA (e.g., introduction of an indel into the genomic DNA). In some cases where the genome editing endonuclease is a class 2 CRISPR/Cas endonuclease (e.g., a Cas9 protein), the genome targeting composition includes a corresponding CRISPR/Cas guide RNA (e.g., a Cas9 guide RNA), or a nucleic acid encoding the CRISPR/Cas guide RNA.

Any of the above methods can also include a step measuring the frequency of indels resulting from the method (e.g., compared to a similar method that does not include a linear non-homologous DNA composition). For example, in some cases, a linear non-homologous DNA composition and a genome targeting composition are introduced into a population of cells, and the frequency of indels at the targeted genomic site is measured (e.g., and in some cases compared to the frequency of indels achieved using a similar method that does not include a linear non-homologous DNA composition).

The components of the methods and compositions (and kits) described herein can be introduced into a cell using any convenient method. For example, a genome targeting composition can be introduced into cells in various forms, including: (i) as an RNP (e.g., comprising a class 2 CRISPR/Cas endonuclease, e.g., a Cas9 protein, and a corresponding guide RNA, e.g., a Cas9 guide RNA); (ii) as protein (e.g., a genome editing endonuclease, e.g., a zinc finger nuclease, a TALEN, a class 2 CRISPR/Cas endonuclease, etc.); (iii) as RNA (e.g., a CRISPR/Cas guide RNA, an RNA encoding a genome editing endonuclease, etc.); (iv) as DNA (e.g., a DNA encoding a genome editing endonuclease, a DNA encoding a CRISPR/Cas guide RNA, etc.); and (v) any combination thereof. A linear non-homologous DNA composition can likewise be introduced using any convenient method, and can be introduced together with a genome targeting composition as part of the same composition, or can be introduced separately from the genome targeting composition.

Examples of ways to introduce the above components include but are not limited to: viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

The components can be introduced into a cell in vivo (e.g., administered to an individual) using any convenient method (e.g., local or systemic, injection, local or system injection, oral, parenteral, subcutaneous, intravenous, intracranial, intraspinal, intraocular, into spinal fluid, and the like). In some cases, introduction can include nucleofection, electroporation, and the like. In some cases, introduction does not include nucleofection or electroporation.

Kits and Compositions

In some cases, a subject kit and/or subject composition includes (a) a linear non-homologous DNA composition (described in detail above), and (b) a genome targeting composition (e.g., comprising a genome editing endonuclease and/or or a nucleic acid encoding the genome editing endonuclease, e.g., a zinc finger nuclease, a TALEN, a class 2 CRISPR/Cas endonuclease, etc.). In some cases, when the genome targeting composition of subject kit and/or subject composition includes a class 2 CRISPR/Cas endonuclease (or a nucleic acid encoding the class 2 CRISPR/Cas endonuclease), a kit or composition of the present disclosure also includes a corresponding guide RNA (or DNA encoding the guide RNA). Components (a) and (b) of a subject kit can be in the same or separate containers.

A composition and/or kit can further include one or more additional reagents, e.g., selected from: a dilution buffer; a reconstitution solution; a wash buffer; a control reagent; a control expression vector or RNA polynucleotide; a reagent for in vitro production of a genome editing endonuclease from DNA or RNA, a reagent for in vitro production of a CRISPR/Cas guide RNA from DNA, and the like.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

The experiments below demonstrate that addition of linear DNA greatly stimulated Cas9-mediated gene disruption in human cell lines by increasing the frequency of insertions and deletions, including efficient capture of the non-homologous DNA at the edited locus. This activity appears to drive cells towards end-joining instead of error-free repair pathways, dramatically increasing the probability of obtaining a homozygous gene knockout.

Results

While investigating parameters to optimize rates of homology directed repair (HDR) during genome editing experiments, it was found that the frequency of error-prone repair outcomes also tended to increase when single stranded HDR donor DNA was present in the editing reaction. Prompted by this observation, a systematic exploration of the parameters underlying DNA-mediated stimulation of error-prone repair events was undertaken. To avoid confounding effects stemming from the use of plasmid or other nucleic acid mediated delivery of Cas9, editing experiments were performed using nucleofection to directly introduce a ribonucleoprotein complex of Cas9 complexed with sgRNA (RNP) into cells.

Targeting the EMX1 locus, a sub-optimal RNP whose activity was approximately 20% in HEK293T cells was selected. The addition of a 127-mer single stranded DNA oligonucleotide derived from BFP, which lacks homology to the targeted locus and whose sequence is absent in the human genome, dramatically increased the appearance of insertions and deletions (indels) as measured by a T7E1 assay (FIG. 1A). Henceforth, such non-homologous oligonucleotides are referred to as "N-oligos". The ability of N-oligos to increase editing efficiency was titratable and depended upon oligo length, with shorter oligos losing efficacy. Native and denatured salmon sperm DNA were also capable of stimulating indels to a similar extent as synthetic single stranded oligonucleotides. Neither the charged agents Heparin and Spermidine (FIG. 3), nor dI-dC had a significant effect on editing. Free DNA ends were required, as closed circular plasmid was ineffective. Importantly, DNA-mediated stimulation of indel formation was specific to the targeted site and did not increase editing at predicted off-target sites as measured by TIDE analysis (FIG. 4).

Figure 1B:
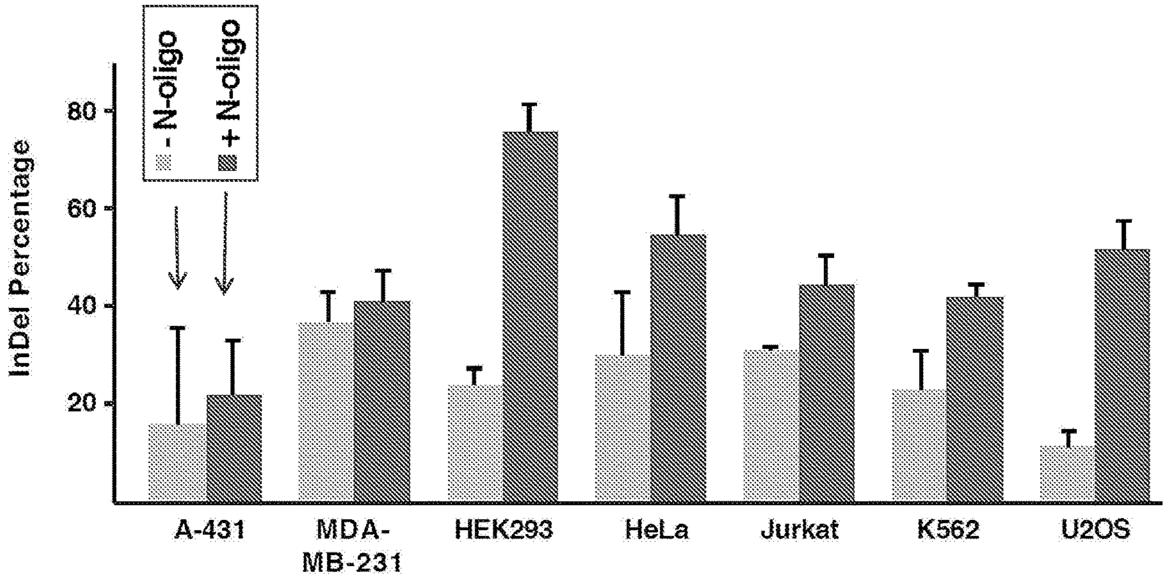
Figure 1C:
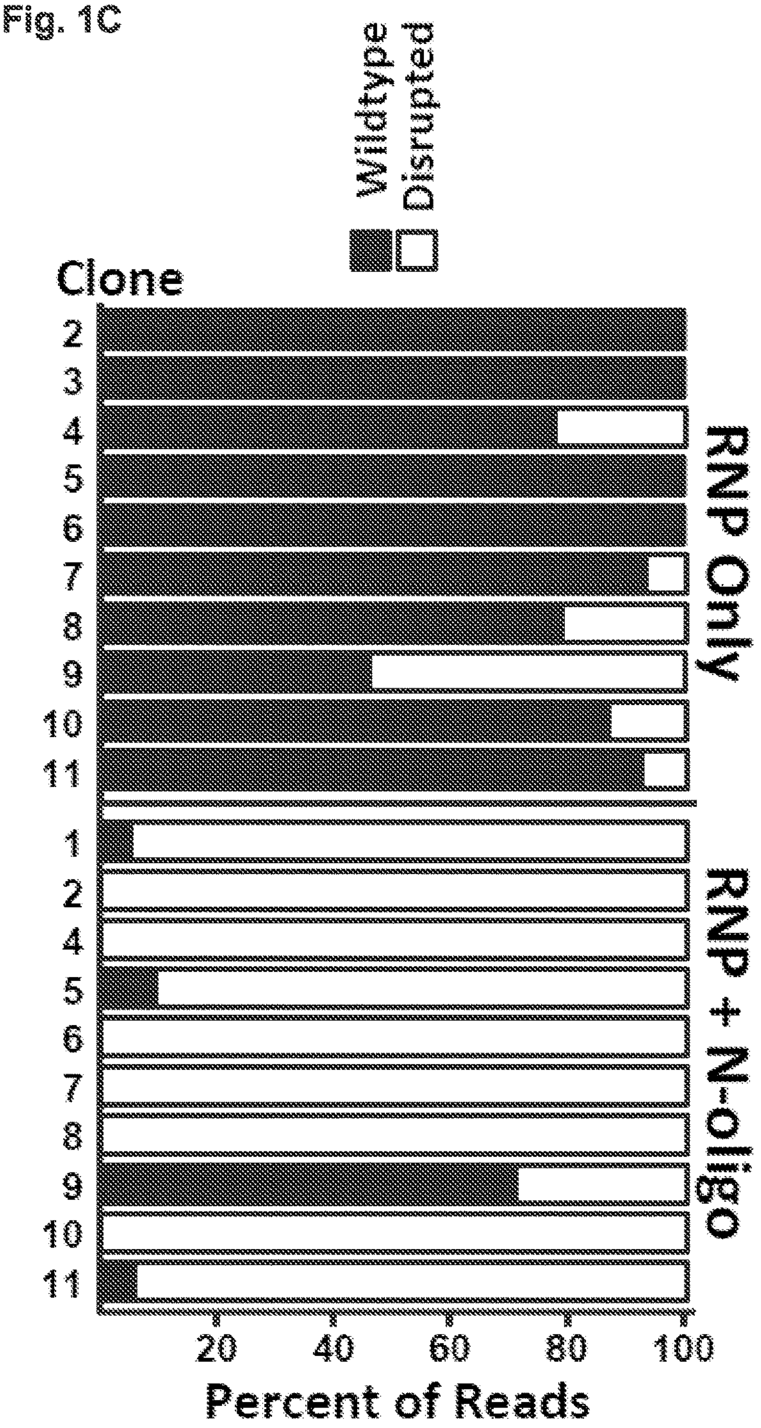

FIG. 1A-1C: Nonhomologous DNA increased gene disruption in multiple cell types. (FIG. 1A) Single and double stranded linear nonhomologous DNA stimulates indel formation in HEK293 cells. Cas9 was targeted to the EMX1 locus with or without nucleic acid carrier agents (non-homologous liner DNAs) (-, no nucleic acid). Indel formation was measured using a T7 endonuclease I assay (mean±standard deviation of at least two independent experiments). (FIG. 1B) N-oligo DNA boosted editing rates in multiple cell types. Editing was performed as described in panel A in multiple cell types either with (dark grey bars) or without (light gray bars) 4.5 μg of N-oligo. (FIG. 1C) N-oligo increased the frequency of homozygous gene disruption. HEK293 cells edited in panel B were clonally isolated and amplicons were sequenced to determine genotype. Each horizontal bar represents a single clone with wildtype sequence or with mutations disrupting EMX1, divisions sized according to the percentage of sequencing reads in each category. Zygosity is summarized in the lower table.

Figures 3, 4:
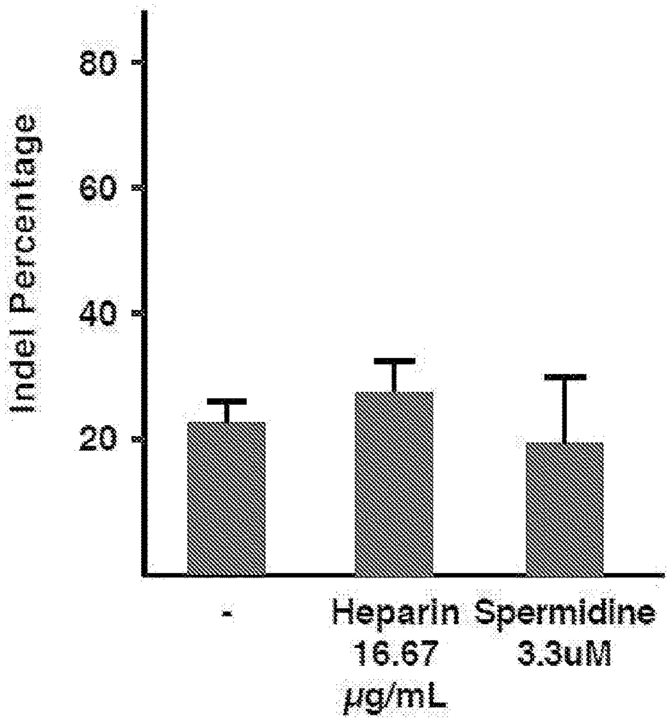
FIG. 3 depicts data related to heparin and spermidine and editing at the EMX1 locus in HEK293 cells.
FIG. 4 depicts data related to linear non-homologous DNA and off-target sites. From top to bottom, SEQ ID NOs.: 1186-1190.

FIG. 3. Heparin and spermidine did not stimulate editing at the EMX1 locus in HEK293T cells. Editing was performed as described in FIG. 1A.

FIG. 4. N-oligo did not stimulate measurable editing at predicted off-target sites. TIDE analysis was performed at EMX1 and four predicted off-target sites following editing experiments performed in the presence or absence of 4.5 μg of salmon sperm DNA. Total efficiency is presented for each case. N/S—not significant, apparent editing at this locus was not significant relative to background.

It was next asked whether the use of N-oligos to increase editing could be generalized to different cell types and genomic loci. N-oligos stimulated indel formation in five out of the seven cell lines tested, with tissue types ranging from bone to blood, including a five-fold increase in indels in U2OS cells (FIG. 1B). N-oligo stimulation of indels was observed at the YOD1 and JOSD1 loci. This stimulation at the YOD1 locus “rescued” an otherwise completely ineffective guide, more than doubling the rate of indel formation from nearly undetectable to approximately 17% (FIG. 5).

Figure 5:
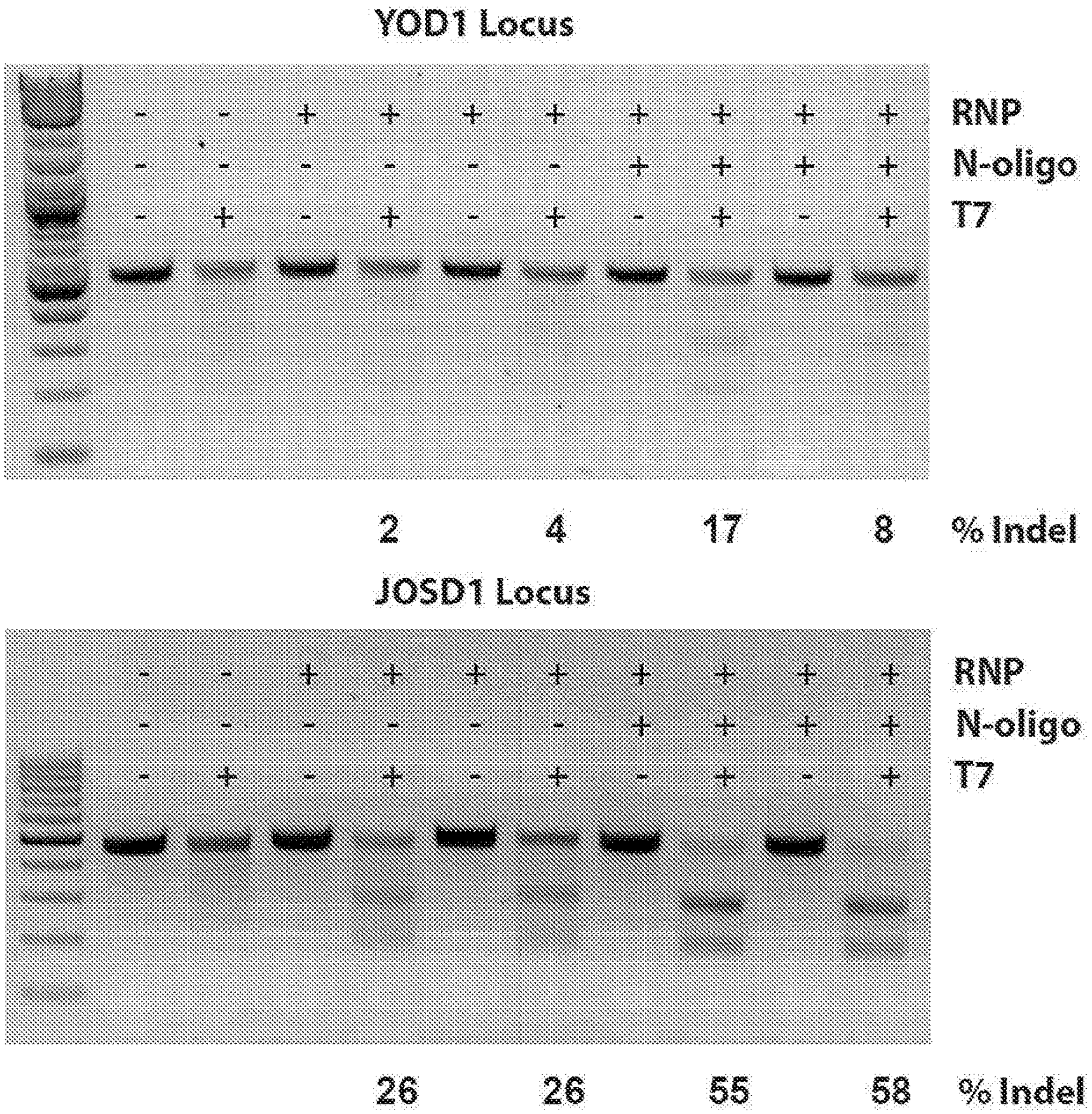
FIG. 5 depicts data related to editing at the YOD1 and JOSD1 loci in HEK293 cells.

FIG. 5. N-oligo stimulated editing at the YOD1 and JOSD1 loci in HEK293 cells. Editing experiments were performed with or without N-oligo as indicated. Indel percentage was assayed by T7 endonuclease cleavage and gel densitometry.

Because the T7E1 indel formation assay operates on an edited pool of cells and does not report on individual alleles, TA/TOPO cloning and Sanger sequencing was used to determine if increased indel frequency corresponded to a higher number of clonal homozygous knockouts. HEK293T cells were the focus because these cells have a tetraploid genome and are thus a stringent test case for the formation of homozygous knockouts. Characterizing clonally isolated edited cells, editing with RNP alone yielded 40% heterozygous clones and no homozygous knockouts, whereas RNP with N-oligos yielded 40% heterozygotes and 60% homozygous knockouts (FIG. 1C). Hence, the use of N-oligos is a simple and effective technique to increase the frequency of homozygous gene disruption.

Figure 2A:
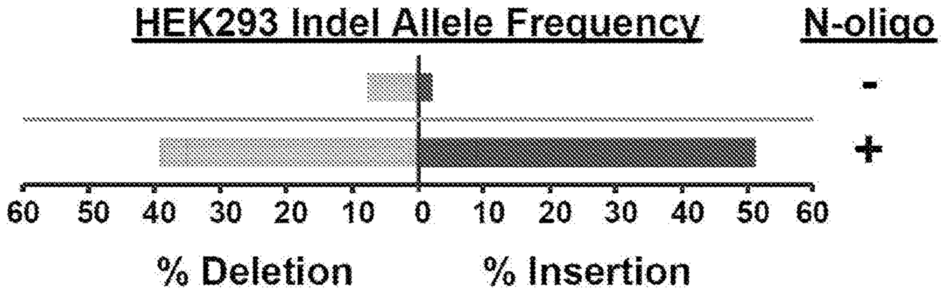
FIG. 2A-2D depict data related to linear non-homologous DNA promoting error-prone repair events. For FIG. 2B, from top to bottom and left to right, SEQ ID NOs.:1178-1185.
Figure 2B:
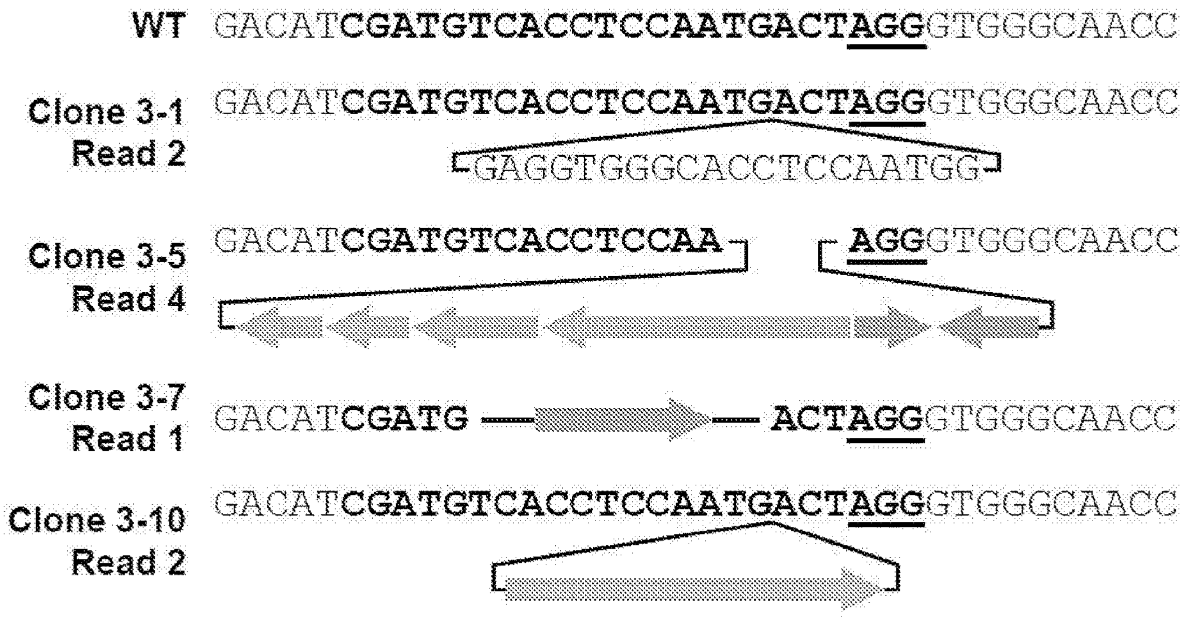
Figure 6:
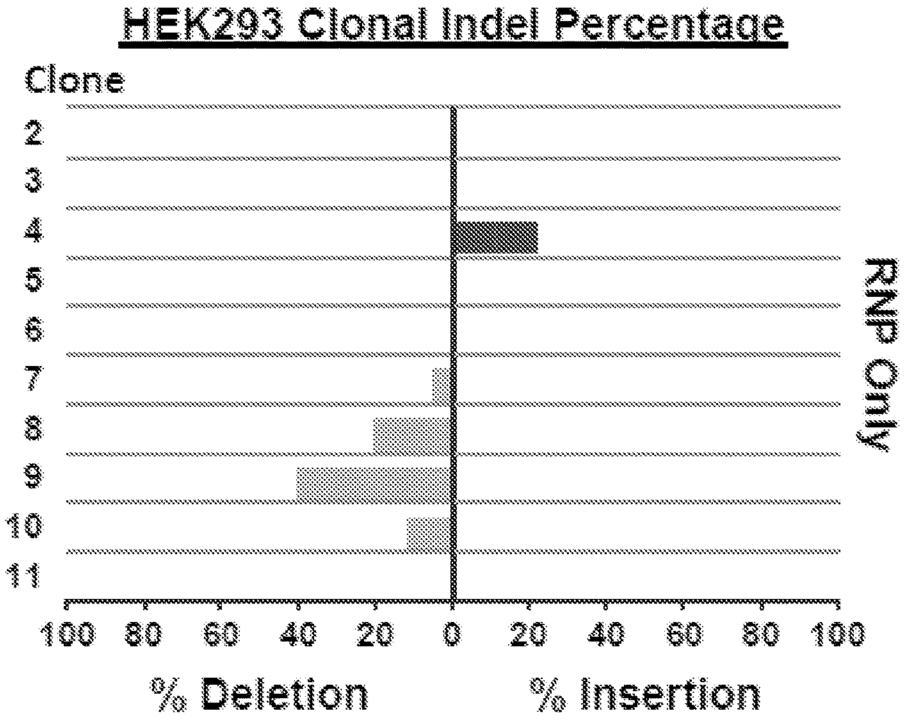
FIG. 6 depicts data related to insertions and deletions in HEK293 cells.
Figure 7:
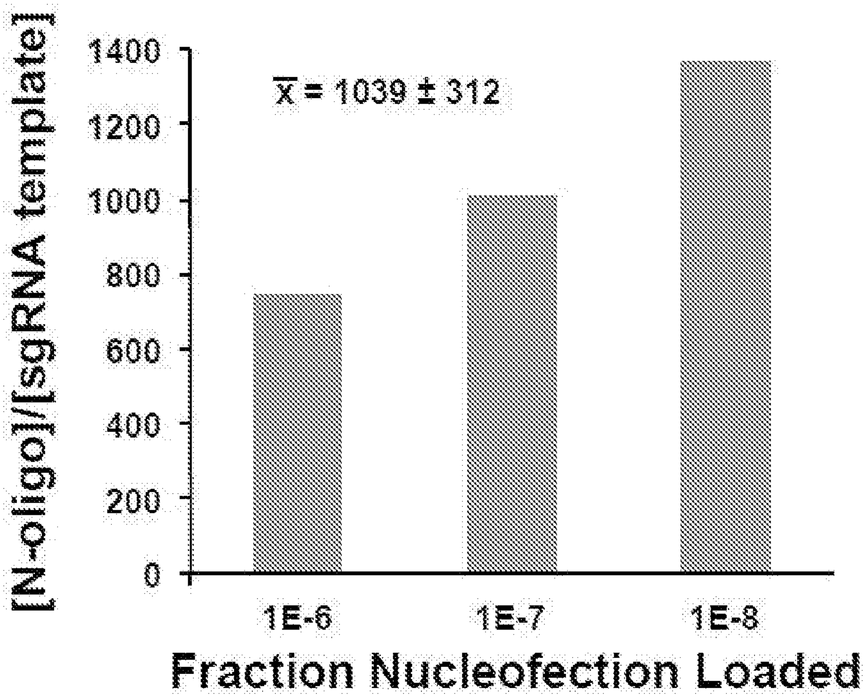
FIG. 7 depicts data related to the presence of linear non-homologous DNA in excess of sgRNA template.

Sequence analysis of the alleles in HEK293 editing reactions revealed that N-oligo treatment increased the rate of both insertions and deletions relative to RNP treatment alone (FIG. 2A). These indels included simple deletion of sequence around the cut site and insertion of random sequence, but also insertion of N-oligo sequence and insertion of the DNA template used for in vitro transcription of the sgRNA (example indels, FIG. 2B; all indels FIG. 6). The frequent presence of sgRNA template sequence was striking, as the N-oligo was approximately 1000-fold more abundant in the nucleofection reactions (FIG. 7). The occasional insertion of non homologous DNA into double strand breaks has been reported in yeast and mice and the insertion of short phosphorothioate-protected oligos forms the basis of the GUIDE-Seq method to detect off-target genome editing events, but the ability of non-homologous single stranded DNA to greatly increase gene knockout by stimulating these events is surprising.

FIG. 2A-2D. N-oligo stimulation of gene disruption promoted error-prone repair events. (FIG. 2A) N-oligo stimulated insertions and deletions in HEK293 cells. The allele frequency of deletions (left, green) and insertions (blue, right) are shown for nucleofections performed with or without N-oligo. Editing is summarized for each clone in FIG. 6. (FIG. 2B) Inserted sequences were derived from single and double stranded heterologous DNA. Wildtype EMX1 sequence is presented at top with the protospacer (bold), PAM (bold underline), and cut site (triangle) diagrammed Four example alleles are presented below with sgRNA template (green) and/or N-oligo (blue) sequence inserted in both orientations. (FIG. 2C) N-oligo stimulated deletions in U2OS cells. Multiple sequence reads from edited cell populations are presented as described in FIG. 2A. (FIG. 2D) Insertion of nonhomologous DNA primarily occurred in HEK293 and K562 cells. DNA harvested from edited cell populations was evaluated using a panel of PCR reactions (diagrammed at top). Primers N1 and N2 anneal to the N-oligo sequence; primers T1 and T2 anneal to residual sgRNA template FIG. 6. N-oligo stimulated insertions and deletions in HEK293 cells. Sequence reads from clonal cell populations were binned into three categories (wild-type (WT), unmodified; deletions, clear removal of sequence; and insertions, added sequence with or without flanking deletions) and presented in table form. Bar graphs present clonal indel percentages.

FIG. 7. N-oligo was present in excess of sgRNA template. Nucleofection mixtures were serially diluted and the abundance of N-oligo or sgRNA template were quantified by quantitative PCR (qPCR). Fold enrichment of N-oligo over sgRNA template are presented for three serial dilutions of nucleofection mixtures. Inset number is the mean+/−standard deviation of these three values.

Figure 2C:
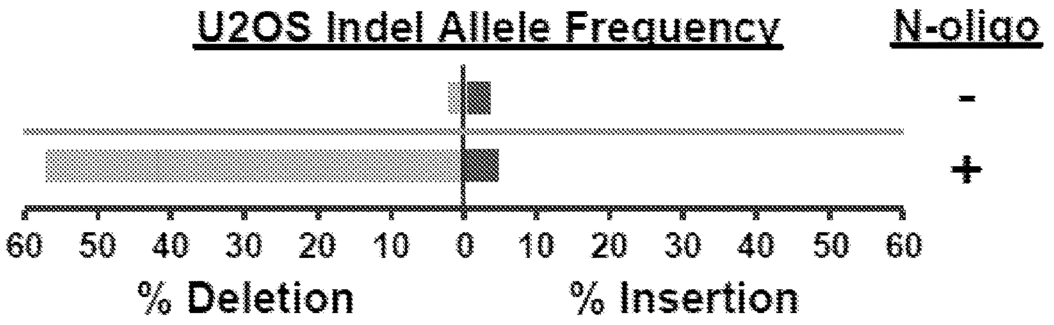
Figure 2D:
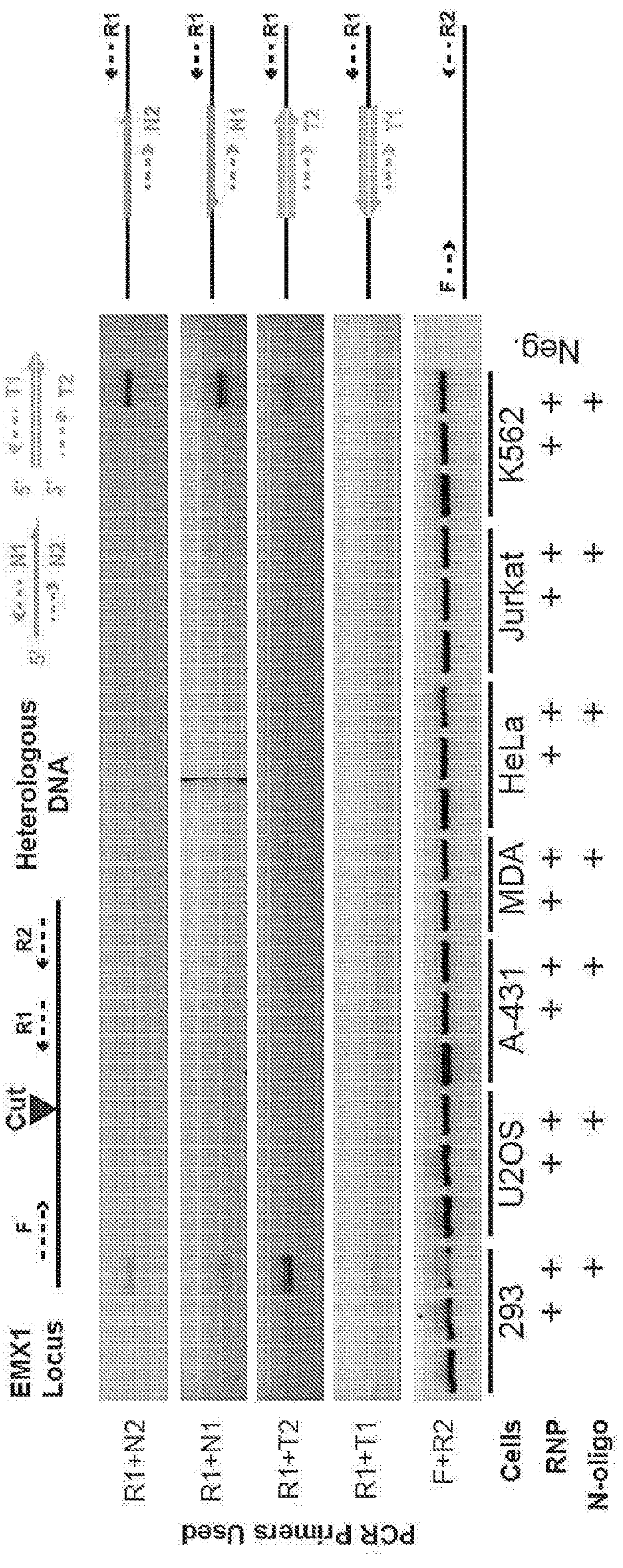

The observations of sequence insertion in HEK293T cells motivated the investigation of the nature of N-oligo stimulated indel formation in other cell types. Sanger sequencing of U2OS editing outcomes revealed that N-oligo treatment primarily stimulated the appearance of large deletions, and not insertions, as compared to RNP alone editing (FIG. 2C). To determine the propensity of various cell types to insert sequences into a Cas9 break point, a PCR assay was designed to amplify either the N-oligo or sgRNA transcription template in various orientations. This assay confirmed sequence insertion in K562 and HEK293T cells, but not in any of the other cell lines that show robust N-oligo indel stimulation (FIG. 2D, FIG. 1B). The ability of N-oligos to stimulate gene disruption with such different molecular outcomes suggests that they stimulate classical or alternative end-joining pathways, thereby boosting the rate of error-prone DSB repair.

Figure 8A:
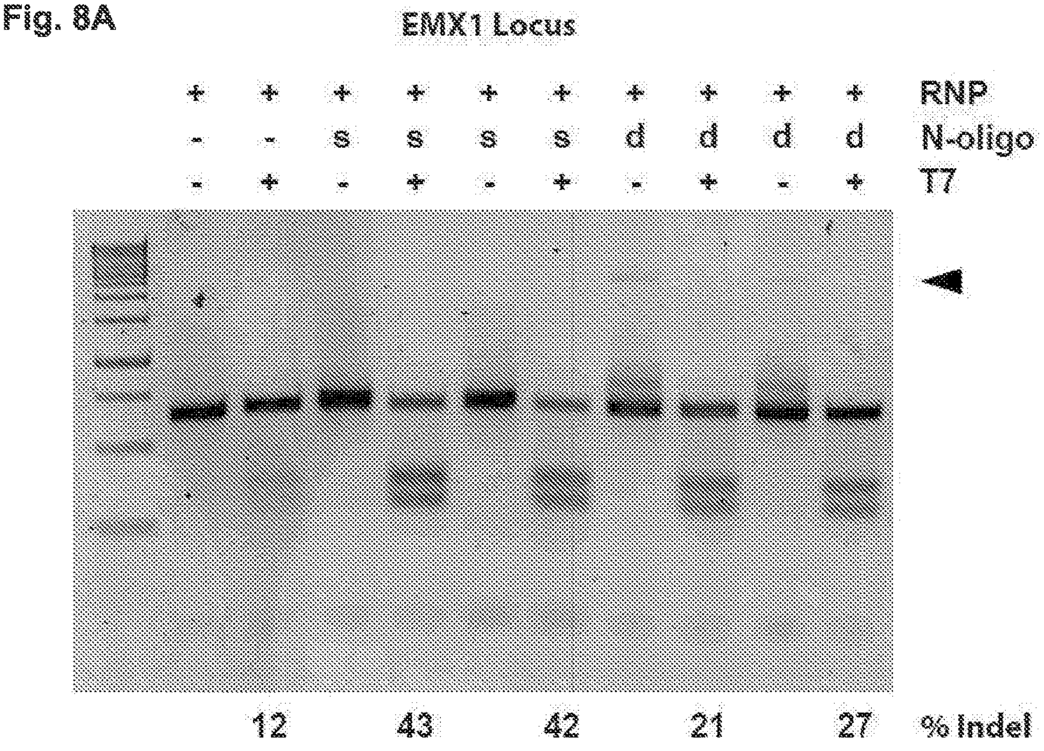
FIG. 8A-8B depict data related to showing that sgRNA template DNA was not required for N-oligo increases to gene disruption.
Figure 8B:
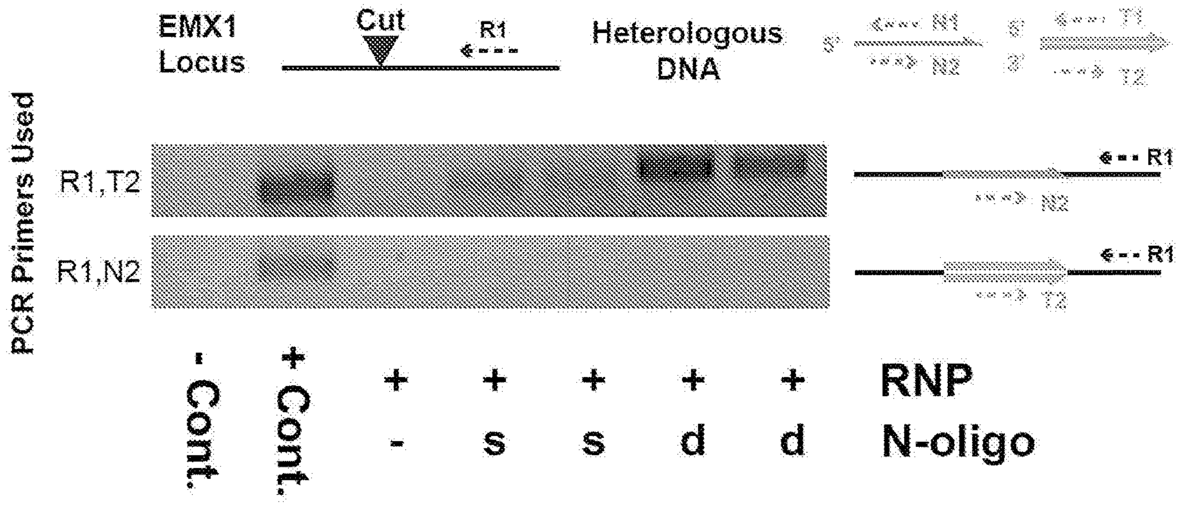

Given the large excess of N-oligo over sgRNA template, it was tested whether providing double stranded non-homologous DNA would also effectively stimulate insertion in these cells. Single and double stranded N-oligos were tested for their potential to increase indels at the EMX1 locus, double purifying the sgRNA before use to ensure that the double stranded sgRNA template was completely removed. Double stranded N-oligo stimulated indels, though about two-fold less effectively than single stranded N-oligo (FIG. 8A). Using a PCR assay for sequence integration, no evidence was found of sgRNA template insertion in doubly-purified samples, but greater integration of the duplex N-oligo relative to single-stranded N-oligo (FIG. 8B). This result suggests that explicitly designing a duplex N-oligo could further bias cells towards a specific outcome, for example inserting a cassette that encodes stop codons in multiple frames and orientations may further bias cells towards a specific repair outcome. This strategy has been proposed for HDR-mediated gene disruption, but to our knowledge has not been attempted with non-homologous integration of oligonucleotides.

FIG. 8A-8B. sgRNA template DNA is not required for N-oligo increases to gene disruption. (FIG. 8A) Extensively purified sgRNA (free of sgRNA template DNA) was used in editing experiments at the EMX1 locus. T7 editing rates increased dramatically with the addition of single or double stranded DNA. (FIG. 8B) PCR for N-oligo or sgRNA template insertion indicates that insertion events are derived from the N-oligo rather than the sgRNA template. Double stranded N-oligos (d) tend to insert more efficiently than single stranded N-oligos(s).

Taken together, the data presented here support a model in which cells fidelitously repair most Cas9-generated DSBs using error-free repair pathways that do not produce measurable indels, but occasional error-prone repair causes indels that ablate portions of the Cas9 protospacer and/or PAM, thereby preventing further cutting and producing a measurable outcome. The addition of N-oligo during editing appears to stimulate error-prone end-joining pathways that differ among cell types (e.g. end-joining of exogenous nucleic acid in HEK293T and large deletions in U205) but have the net effect of increasing the rate of gene disruption. The use of N-oligos can be extremely valuable in generating homozygously gene-disrupted cell lines or organisms, and will be particularly effective in challenging polyploid contexts.

Materials and Methods

Cell Lines and Cell Culture

A-431, HEK293, HeLa, Jurkat, K562, MDA-MB-231, and U2OS cells were acquired from the UC Berkeley Tissue Culture Facility. A-431, HeLa, and MDA-MB-231 cells were maintained in DMEM glutamax medium supplemented with 10% fetal bovine serum, 1% sodium pyruvate, 1% non-essential amino acids, and 100 μg/mL penicillin-streptomycin. HEK293 and U2OS cells were maintained in DMEM medium supplemented with 10% fetal bovine serum, 1% sodium pyruvate, and 100 μg/mL penicillin-streptomycin. Jurkat and K562 cells were maintained in RPMI medium supplemented with 10% fetal bovine serum, 1% sodium pyruvate, and 100 μg/mL penicillin-streptomycin.

Cas9 and RNA Preparation

*S. pyogenes* Cas9 (pMJ915, Addgene #) with two nuclear localization signal peptides and an HA tag at the C-terminus were purified by a combination of affinity, ion exchange, and size exclusion chromatography steps as described, except protein was eluted at 40 uM in 20 mM HEPES KOH pH 7.5, 5% glycerol, 150 mM KCl, 1 mM dithiothreitol (DTT).

sgRNAs were generated by HiScribe (NEB E2050S) T7 in vitro transcription using PCR-generated DNA as a template (dx.doi.org/10.17504/protocols.io.dm749m).

Cas9 RNP Assembly and Nucleofection 100 pmoles of Cas9-2NLS was diluted to a final volume of 5 uL with Cas9 buffer (20 mM HEPES (pH 7.5), 150 mM KCl, 1 mM $MgCl_2$, 10% glycerol and 1 mM TCEP) and mixed slowly into 5 μL of Cas9 buffer containing 120 pmoles of L2 sgRNA. The resulting mixture was incubated for ten minutes at room temperature to allow RNP formation. 2E+05 cells were harvested, washed once in PBS, and resuspended in 20 uL of nucleofection buffer (Lonza, Basel, Switzerland). 10 uL of RNP mixture, 4.5 μL of N-oligo, and cell suspension were combined in a Lonza 4d strip nucleocuvette. Reaction mixtures were electroporated, incubated in the nucleocuvette at RT for ten minutes, and transferred to culture dishes containing pre-warmed media (dx.doi.org/10.17504/protocols.io.dm649d). Editing outcomes were measured two days post-nucleofection by T7E1 (see below). Resuspension buffer and electroporation conditions were the following for each cell line: A-431 in SF with EQ-100, HEK293 in SF with DS-150, HeLa in SE with CN-114, Jurkat in SE with CL-120, K562 in SF with FF-120, MDA-MB-231 in SE with CH-125, and U2OS in SE with CM104.

PCR Amplification of Edited Regions

PCR amplification of EMX1 was done using primers oCR295 and oCR296. PCR amplification of YOD1 was done using YOD1f and YOD1r. PCR amplification of JOSD1 was done using JOSD1f and JOSD1r. PCR reactions were performed with 200 ng of genomic DNA and Kapa Hot Start high-fidelity polymerase with the GC buffer. The thermocycler was set for one cycle of 95° C. for 5 min, 30 cycles of 98° C. for 20 sec, 62° C. for 15 sec, 72° C. for 30 sec, and one cycle of 72° C. for 1 min, and held at 4° C.

T7EI Assay

The rate of Cas9 mediated gene disruption was measured by T7 endonuclease I digestion of hybridized PCR. 200 ng of PCR DNA in 1×NEB Buffer 2 was hybridized in a thermocycler under the following conditions: 95° C. for 5 min, 95-85° C. at −2° C./sec, 85-25° C. at −1° C./sec, and held at 4° C. 10 units of T7EI (NEB, M0302) were added to the sample and was incubated at 37° C. for 15 min. The sample was then immediately run on a 2% agarose gel containing ethidium bromide. Band intensities were quantified by imageJ. Indel percentage was calculated using the following equation: $(1-(1-(\text{cut product intensities}/\text{uncut}+\text{cut product intensities}))^{1/2})\times 100^5$.

Insert Based PCR Assay

To assay the insertion of N-oligo and sgRNA template DNA into the cut site, a reverse primer (oGJR102) was designed to pair with forward primers homologous to the: BFP N-oligo inserted in the forward direction (oGJR097), BFP N-oligo inserted in the reverse direction (oGJR098), the T7 promoter of the sgRNA template inserted in the forward direction (oGJR099), and the T7 promoter of the sgRNA template inserted in the reverse direction (oGJR100). Presence of EMX1 DNA in the PCR reaction was verified using the EMX1 PCR performed above. PCR reactions were performed with 200 ng of genomic DNA and Kapa Hot Start high-fidelity polymerase. The thermocycler was set for one cycle of 95° C. for 5 min, 30 cycles of 98° C. for 20 sec, 64° C. for 15 sec, 72° C. for 30 sec, and one cycle of 72° C. for 1 min, and held at 4° C. The sample was then run on a 2% agarose gel containing ethidium bromide.

qPCR on RNP sgRNA template and N-oligo DNA present in the nucleofection reaction mixture was quantified on a Mastercycler 2 qPCR machine (Eppendorf, Hamburg). Primers oCR427 and oCR428, sgRNA template; oGJR103 and oGJR104, N-oligo were used at a final concentration of 500 nM in Power SYBR green reaction mixture (Thermo Fisher). Reaction conditions were 95° C. for 10 minutes followed by 40 cycles of 95° C. for 30 seconds and 65° C. for 60 seconds. The ratio of N-oligo to sgRNA template was quantified using the equation $r=2^\wedge(Ct_{sgRNA}-Ct_{N\text{-}oligo})$. Ratios from three serial dilutions of template DNA were averaged and presented as mean±standard deviation.

TIDE Analysis

Off-target analysis was performed on the top 4 targets. Sequences are presented in FIG. 4. Genomic sequences were amplified using KAPA polymerase and Sanger sequenced by the UC Berkeley Sequencing Core. PCR reactions were performed using 200 ng of genomic DNA and the thermocycler was set for one cycle of 95° C. for 5 min, 30 cycles of 98° C. for 20 sec, the annealing temperature for 15 sec, 72° C. for 30 sec, and one cycle of 72° C. for 1 min, and held at 4° C. Off-Target 1 PCR was done with oGJR051 and oGJR096 with a 64° C. annealing temperature, off-Target 2 PCR was done with oGJR090 and oGJR091 with a 62° C. annealing temperature, off-Target 3 PCR was done with oGJR053 and oGJR071 with a 64° C. annealing temperature, and off-Target 4 PCR was done with oGJR054 and oGJR072 with a 66° C. annealing temperature.

Example 2

Selection-Free Genome Editing of the Sickle Mutation in Human Adult Hematopoietic Stem/Progenitor Cells Sickle Cell Disease (SCD) is a recessive genetic disorder caused by a single nucleotide polymorphism (SNP) in the ß-globin gene (HBB). Sickle hemoglobin damages erythrocytes, causing vasoocclusion, severe pain, progressive organ damage, and premature death. The data disclosed herein show the optimization of design and delivery parameters of a ribonucleoprotein (RNP) complex comprising Cas9 protein and unmodified sgRNA together with a single-stranded DNA oligonucleotide donor (ssODN) to facilitate efficient replacement of the SCD mutation in human HSPCs. Corrected HSPCs from SCD patients produced less sickle hemoglobin RNA and protein and correspondingly increased wild-type hemoglobin when differentiated into erythroblasts. When engrafted in immunocompromised mice, ex vivo treated human hematopoietic stem/progenitor cells (HSPCs) maintained SCD gene edits throughout sixteen weeks. These results demonstrate that an accessible approach combining Cas9 RNP with an ssODN can mediate efficient HSPC genome editing and facilitates gene editing treatments for SCD and other hematopoietic diseases.

Sickle Cell Disease (SCD) is a recessive genetic disorder that affects at least 90,000 predominantly African-American individuals in the US and hundreds of thousands worldwide. SCD is caused by a single nucleotide polymorphism (SNP) in the seventh codon of the gene for β-globin (HBB), one of two globins that make up the major adult form of hemoglobin. The resulting glutamate-to-valine substitution renders hemoglobin prone to polymerization under hypoxic conditions, leading to characteristic "sickle" shaped red blood cells (RBCs). Sickle RBCs have a markedly reduced lifespan in the bloodstream, damage the vasculature, and cause vasoocclusion. Major clinical manifestations of SCD are chronic anemia, severe pain episodes, and progressive damage to vital organs such as the brain, lung and kidney. In the United States, the disease causes a 30-year decrement in lifespan, and a greatly diminished quality of life.

RBCs are produced from re-populating hematopoietic stem cells (HSCs) in the bone marrow, and allogeneic hematopoietic cell transplantation (HCT) from an unaffected HLA-matched donor is currently the only lasting cure for SCD. However, HCT has been employed sparingly because of the difficulty in identifying donors, risks associated with the toxicity of the transplant regimen (requiring preparation with chemotherapy and immune suppression), and potentially fatal graft-versus-host disease. Recent transplant advances have reduced these risks in children and extended treatment to selected adults and individuals for whom only a haploidentical HLA donor is available. Still, the vast majority of individuals with SCD do not pursue allogeneic HCT due to an unfavorable risk-reward profile, especially during early childhood. A curative treatment for SCD that can be safely applied to more people remains an urgent need.

Because sickle RBCs have a markedly shorter lifespan in circulation compared to wild type RBCs, even low levels of genotypic correction are predicted to generate a clinical benefit. Indeed, observations in patients after allogeneic HCT suggest that clinical improvement may occur when as few as 2-5% of long-term engrafted cells carry a normal HBB allele. An ideal gene editing treatment would exceed this modest target, but to date even this level of gene editing has not been achieved.

During gene editing, a targeted nuclease creates a double strand break (DSB) that can be repaired by one of two mechanisms: error-prone non-homologous end joining (NHEJ) that leads to genomic insertions and deletions (indels), or templated homology-directed repair (HDR) to precisely insert, delete, or replace genomic sequence. To date gene editing has yet to achieve long-term correction of the SCD mutation in these cells at levels greater than 1%, based on engraftment in immune compromised mice.

Results

A goal of the work described herein was not only to develop an approach to edit HSPCs as a treatment for SCD, but also to use reagents that are inexpensive and accessible to a wide variety of researchers.

Figure 9A:
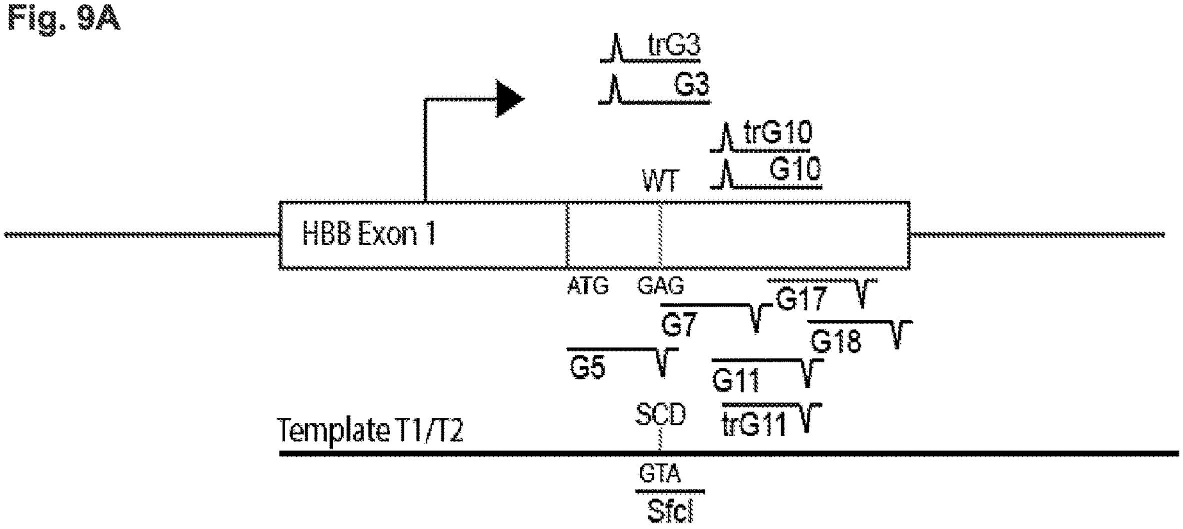
FIG. 9A-9E depict data related to editing the SCD SNP in K562 cell.

A pipeline to enable efficient, RNP/ssODN-based correction of the SCD mutation was developed without introducing a selective marker (FIG. 9A). An erythroleukemia cell line was used to explore a panel of Cas9 RNPs that cut near the SCD mutation. The most effective RNPs were then used to develop ex vivo editing methods in human HSPCs, achieving up to 33% sequence replacement. Efficient correction of the sickle mutation in SCD HSPCs is demonstrated in the work provided herein, with corresponding production of wild type adult hemoglobin (HbA) RNA and protein in edited, differentiated erythroblasts. After engrafting edited human HSPCs in immune-compromised mice, sequence replacement at the SCD locus was retained at four months post-engraftment at high levels.

Prioritizing SCD Editing Reagents in a Model Cell Line

Pairing Cas9 with various sgRNAs can lead to different activities on the same gene target. For HDR-mediated editing, each sgRNA can be paired with an HDR donor template that encodes the desired nucleotide changes. Coupled with subtleties of donor template design and reagent delivery, the complexity of this problem expands rapidly. A rapid pipeline to prioritize sgRNAs and HDR donors in a model cell line prior to more focused optimization in primary human HSPCs was therefore developed. Single-stranded DNA oligonucleotide donors (ssODNs) were used that are inexpensive and widely available, and co-delivered these with the Cas9 RNP by electroporation.

sgRNAs and ssODNs were searched for that are active in K562 cells, a human erythroleukemia line that resembles early committed hematopoietic progenitors. Two parameters when designing sgRNAs and ssODNs for HDR experiments are the distance between the sgRNA recognition site and the mutation, and the ability to silently ablate the sgRNA protospacer adjacent motif (PAM). The ablation of the PAM ensures that Cas9 cannot re-cut corrected alleles, thus preventing the introduction of indels into the corrected allele.

Figure 13A:
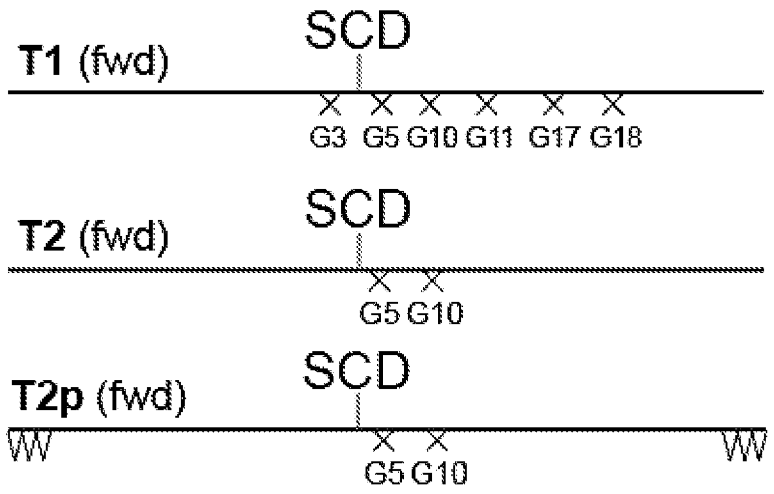
FIG. 13A-13G depict data related to FIG. 9.

To find maximally active sgRNAs compatible with SCD editing targets were identified in the first exon of the HBB gene and six of them were tested for which the PAM could be silently mutated (G3, G5, G10, G11, G17, G18) and one was tested for which it could not (G7) (FIG. 9A). Truncated versions of three guides were also tested (trG3, trG10, trG11; FIG. 19), a modification that is reported to reduce off-target cleavage without compromising on-target efficiency. An initial ssODN (T1) was designed that contains silent mutations in the PAMs of all sgRNAs and a WT-to-SCD edit (K562 cells are WT at HBB FIG. 13A). The combination of the WT-to-SCD SNP mutation and removal of the G5 PAM generated a silent SfcI restriction site, allowing easy tracking of HDR-mediated editing (FIG. 13A).

FIG. 13A-13G depict data related to FIG. 9. A) Initial templates are 195 nt long, and edit the WT SNP to SCD. To prevent re-cutting, template 1 encoded silent mutations for the PAMs of all the sgRNAs tested. Templates T2 and T2p had PAM mutations only for G10 and G5. Template T2p had three 3' and three 5' phosphorothioate linkages to prevent degradation by endogenous exonucleases. B) Editing outcomes of K562 cells edited with unprotected template T2 and phosphorothioate-protected T2p, analyzed by NGS. C) Genomic DNA from K562 cells edited with indicated RNPs and templates were analyzed by ddPCR using probes and primers as indicated in Materials and Methods. Error bars are SEM of 3 independent biological replicates, each consisting of 3 technical replicates. Template T88-107 is identical to T2. See text for details. D) T7 endonuclease 1 assay of PCR amplicons from the HBB SCD region or the corresponding region in HBD, from K562 cells edited with indicated RNPs, analyzed on a 2% agarose gel. Both the G5 and G10 RNPs cut efficiently at HBB, and G5 also cuts at HBD. E) Design of ssDNA templates, relative to the G10 cut site. Templates consist of a shorter "annealing" arm that anneals to the strand liberated by RNP binding, and a longer "homology" arm that drives incorporation of the desired edit. F) K562 cells were electroporated with the trG10 sgRNA as indicated, along with the indicated asymmetric template, defined by the lengths of the homology and annealing arms, respectively (homology length-annealing length). Editing outcomes were assessed by NGS. G) Conversion of HBB coding sequence to HBD at the HBB locus, assessed by NGS.

FIG. 19. Zygosity of clonal colonies of CD34+ HSPCs edited with the trG10 RNP. HSPCs were edited with 75 pmol of the trG10 RNP (similar to FIG. 10), and cloned by limiting dilution. 96 of the resulting clones were then genotyped by NGS. The fraction of all three alleles, the frequency of clones with at least one copy of each of the three alleles, and the frequency of all six genotypes are indicated.

Figure 9B:
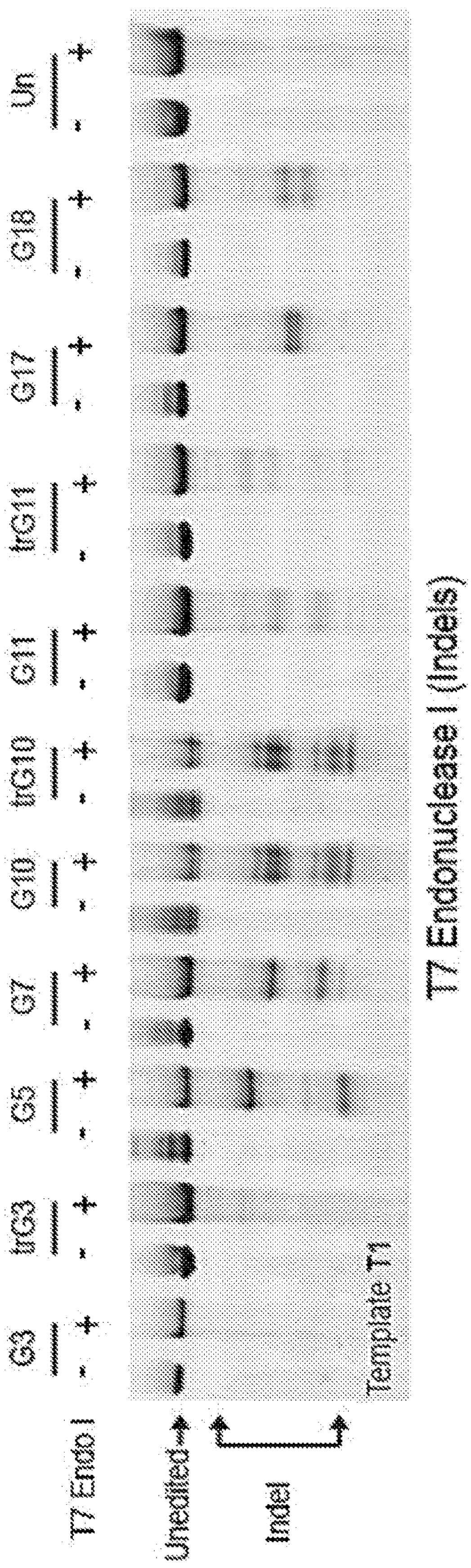
Figure 9C:
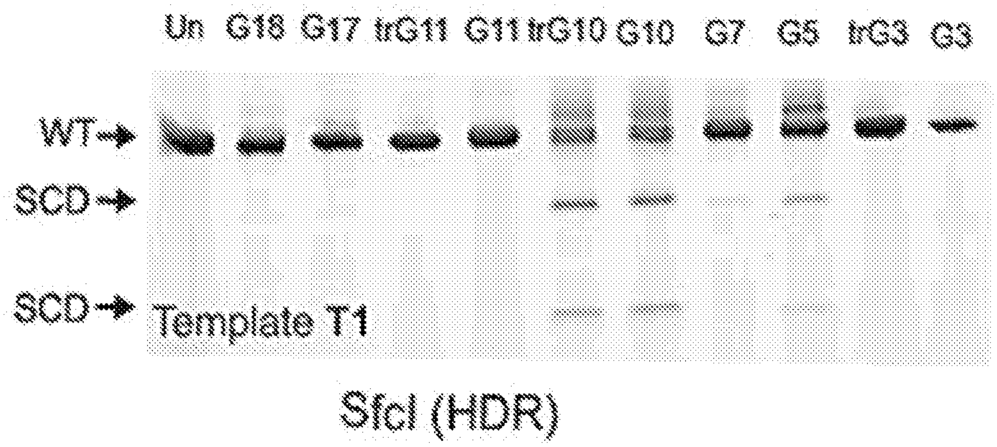
Figure 9D:
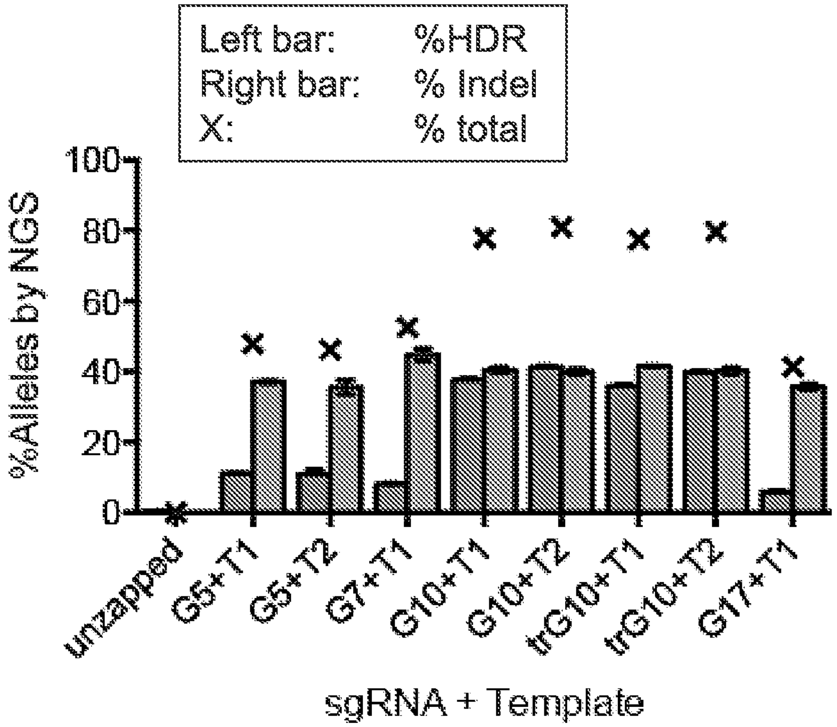

Cas9 RNPs were assembled from each candidate sgRNA and were individually delivered to K562 cells together with the ssODN by electroporation. A dose of 100 pmol of each RNP and template was used per 150,000 K562 cells. A T7 endonuclease I digest of PCR amplicons from edited cell pools, which in this case detects mismatches arising from both NHEJ- and HDR-mediated repair of Cas9 DSBs, revealed sequence modifications with all but two sgRNAs (G3 and trG3) (FIG. 9B). SfcI digest showed appreciable HDR-mediated editing of the SCD SNP with three sgRNAs, G5, G10, and trG10 (G10 with an 18-nt guide sequence) (FIG. 9C).

Figure 13B:
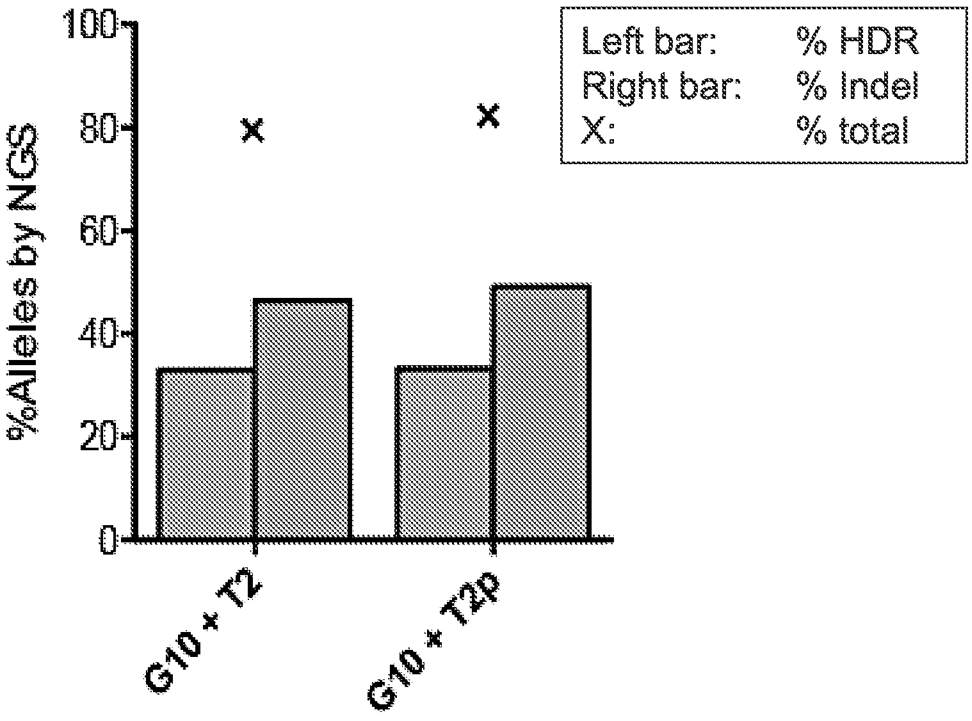
Figure 13C:
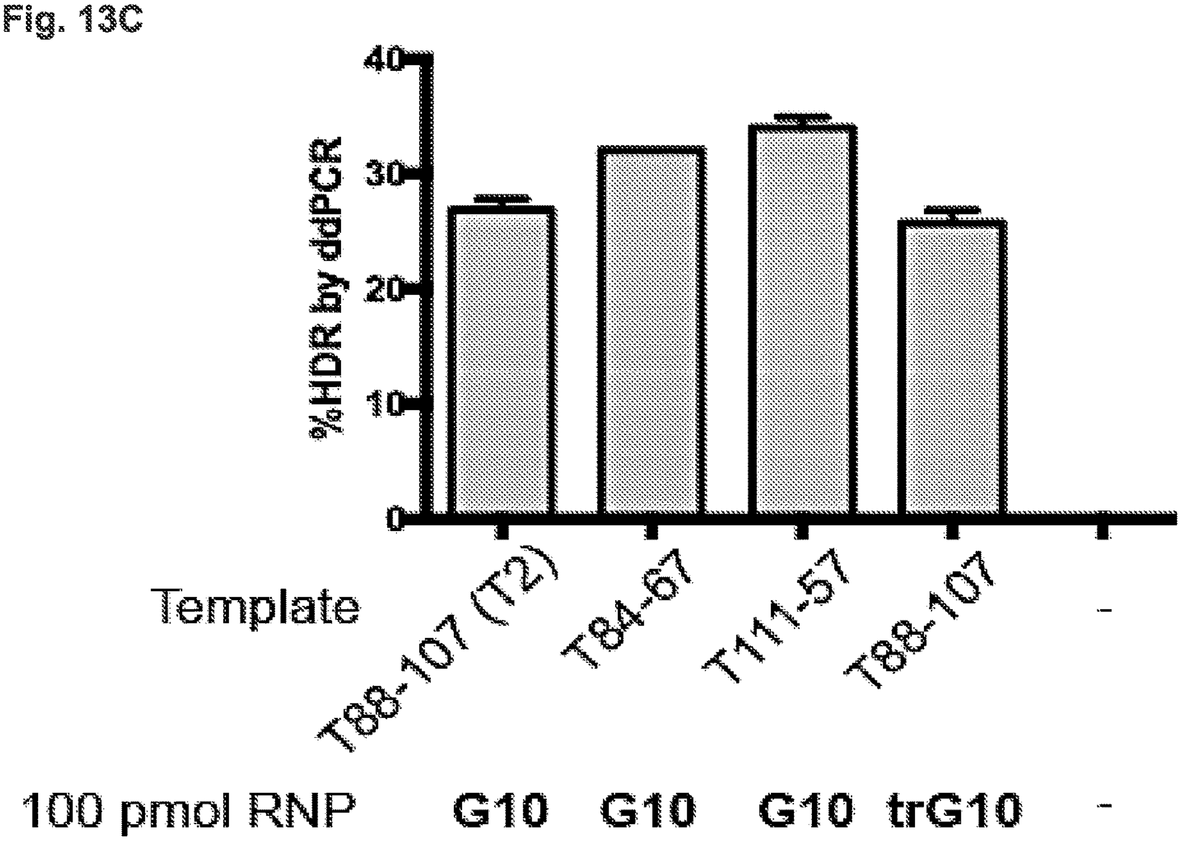
Figure 13D:
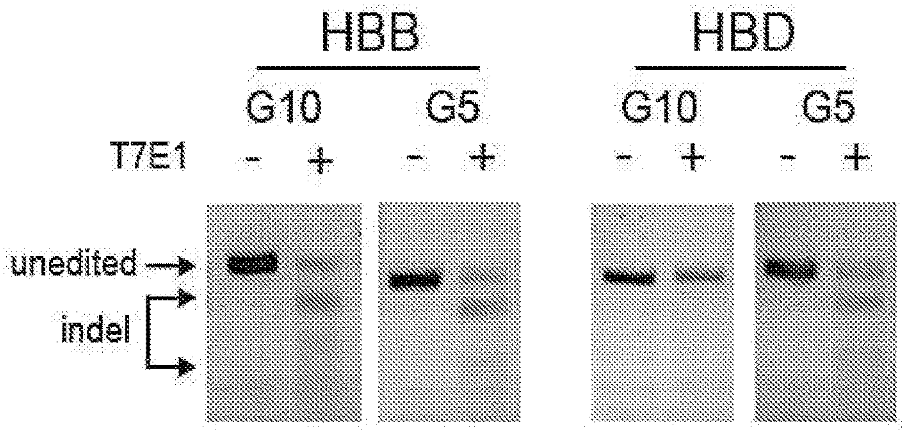

The frequency of HDR and indel formation at the SCD SNP was quantified by next-generation sequencing (NGS) of PCR amplicons derived from genomic DNA extracted from pools of edited cells (FIG. 9D), and by droplet digital PCR (ddPCR, FIG. 13C). When the trG10 Cas9 RNP was provided without an ssODN, 90% of NGS reads contained indels, indicating excellent delivery of the RNP and efficacious gene knockout (FIG. 13F). Experiments were performed using both the T1 ssODN and a derivative of T1 bearing only the WT-to-SCD edit and the G5 and G10 PAM mutations (T2) (FIG. 13A). Most candidate sgRNAs induced substantial quantities of indels (35-40% of reads) (FIG. 9B and 9D), and G5, G10, and trG10 also yielded high levels of WT-to-SCD HDR (11% of reads for G5, 41% of reads for G10) from multiple donor designs (FIG. 9 and FIG. 13). A phosphorothioate-protected ssODN did not improve HDR frequencies (FIG. 13B). The G5 guide targets a sequence very similar to one found in the closely related hemoglobin-delta (HBD) gene, and it was experimentally verified that this guide induced indels in HBD (FIG. 13D). Hence, the truncated trG10 guide was selected for further testing.

FIG. 9A-9E. Editing the SCD SNP in K562 cells. A) Schematic depicting experimental approach to editing in K562 cells. A panel of 10 sgRNAs that cut within 100 bp of the SCD SNP was selected. A WT-to-SCD edit was programmed by an ssDNA template (T1) bearing silent PAM mutations for the sgRNAs, which also introduces a SfcI restriction site. B) T7 endonuclease 1 assay depicting indel formation in pools of cells edited by candidate RNPs. C) Editing of candidate sgRNAs detected by SfcI digestion. G5, G10 and a truncated variant, trG10, efficiently edit in K562 cells. D) Gene modification of select sgRNAs and templates at the SCD SNP, assessed by NGS. See FIG. 13 for definitions of donors T1 and T2. (average of 3 biological replicates, error bars indicate standard deviation). E) Analysis of off-target cutting by the G10 RNP at sites predicted by the online CRISPR-Design tool, in K562 cells, determined by NGS.

Figure 13E:
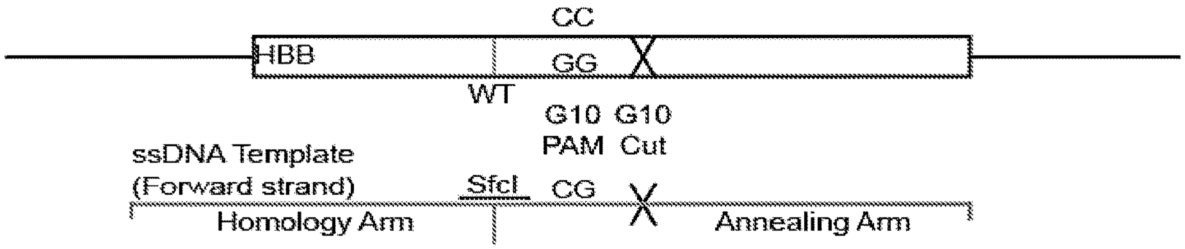
Figure 13F:
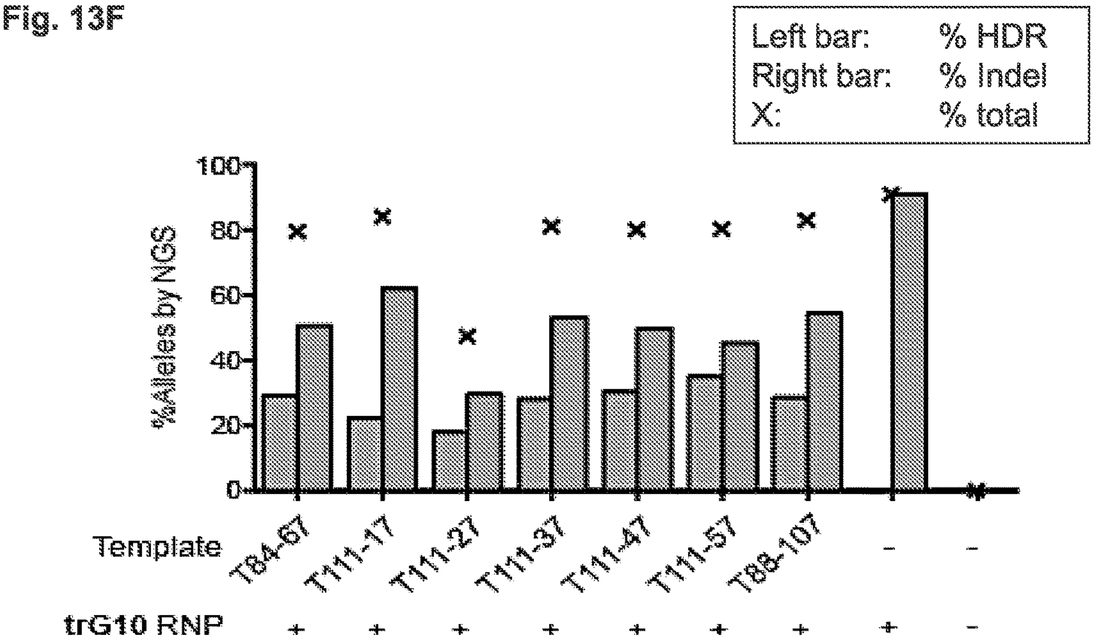

For sgRNAs that target the sense strand such as G10, the best template to employ matches the sense strand (annealing to the antisense strand) and has a long 5' homology arm and a shorter 3' annealing arm (FIG. 13E). Based on these principles, the templates will henceforth be named by the lengths of their 5' and 3' homology arms relative to the G10 cut site. For example, the initial template T2 is termed T88-107. Unless noted, all templates bear only the G5 and G10 PAM mutations. The effects of asymmetric templates containing the SCD-to-WT edit on HDR-mediated editing in K562 cells were tested (FIG. 13F). A template with a 111 nt 5' arm and a 57 bp 3' arm (T111-57) yielded an HDR frequency modestly higher than the original template T88-107 (33% vs. 28.5% in the same experiment). High rates of HDR in all conditions, and a modest increase in HDR using asymmetric templates, were also confirmed by ddPCR (FIG.

Figure 13G:
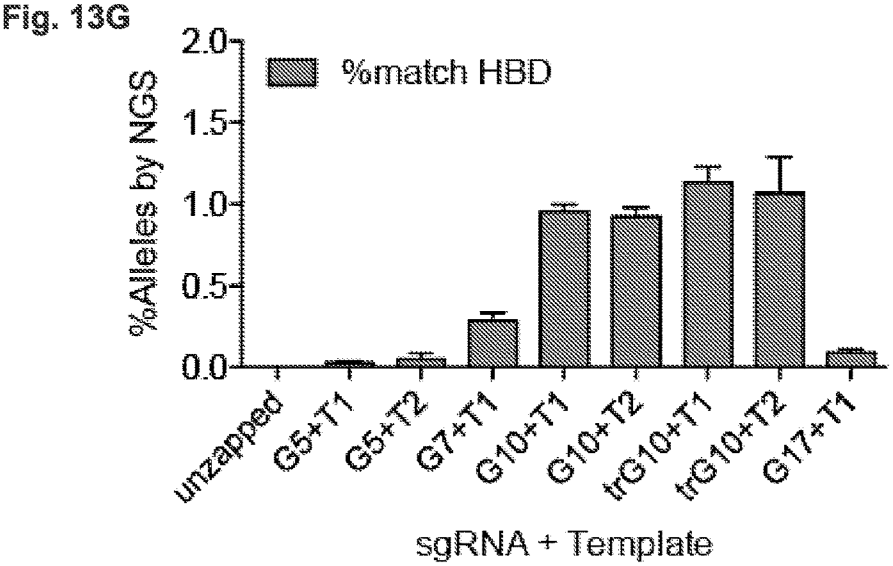

13C). Low but measureable rates of conversion (0.5-1%) between the HBB coding sequence and the homologous region in HBD were also detected, but this was only observed in samples treated with G7, G10 and trG10 (FIG. 13G).

Figure 9E:
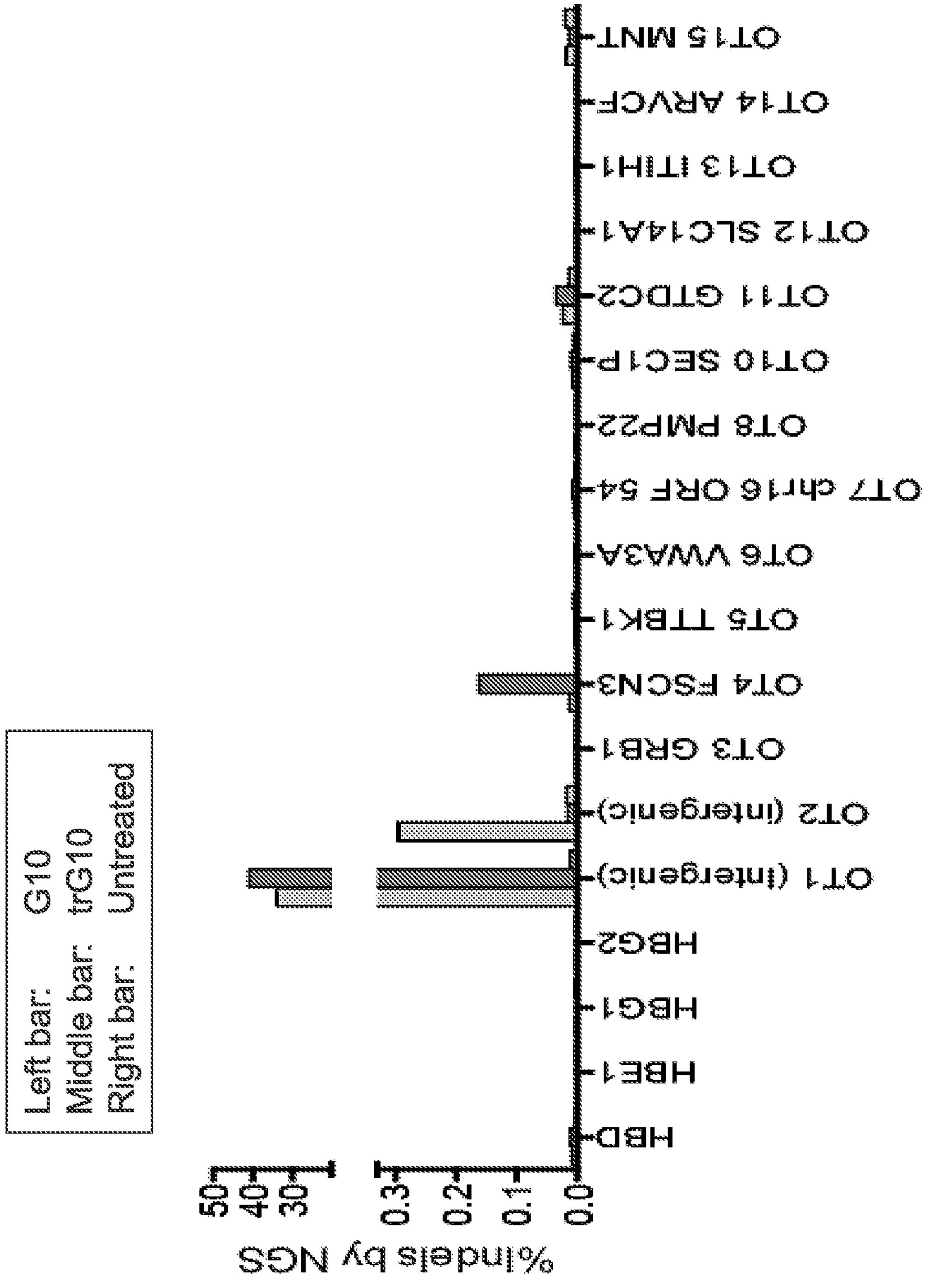

Off-target candidates were selected by sequence similarity using a popular off-target prediction tool, and NGS of PCR amplicons was used to analyze the off-target activity G10 and trG10 Cas9 RNPs in K562 cells (FIG. 9E). The two top-scoring off-targets (which are both intergenic), the top 13 exonic off-targets, and predicted off-target sites within the four globin genes (HBD, HBE1, HBG1, and HBG2, FIG. 14) were assessed.

Figure 14:
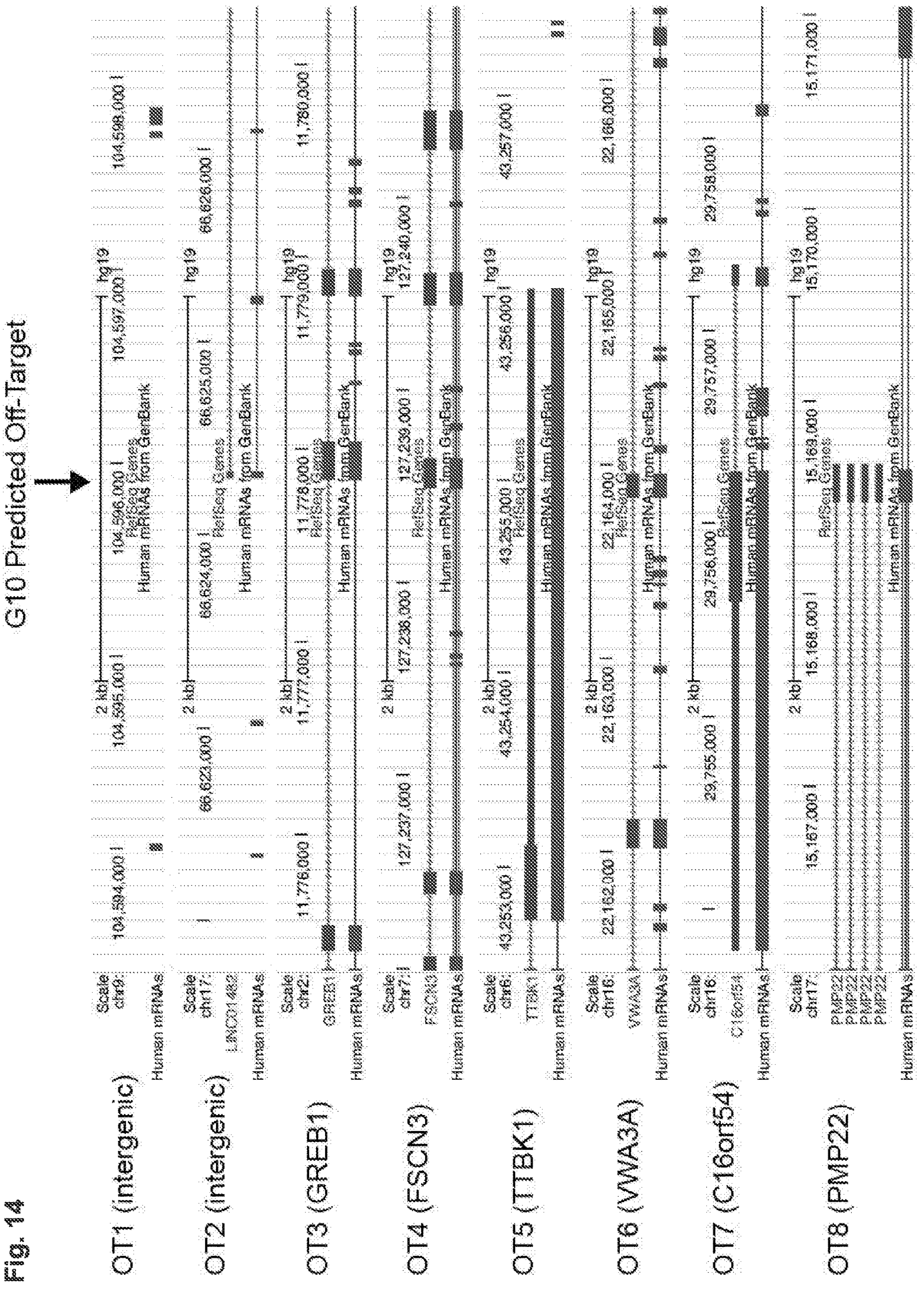
FIG. 14 depicts genomic context of predicted off-target cut sites for the G10 RNP.

FIG. 14 depicts genomic context of predicted off-target cut sites for the G10 RNP. Sites were selected using the online CRISPR-design tool, according to criteria discussed in the text. Screenshots of the 5 kb region near the off-target site were prepared using the UCSC genome browser.

Very little exonic off-target activity was observed, with most off-target sites showing no Cas9-dependent indel formation at rates within the limit of detection (~0.001%) (FIG. 9*e*). Substantial off-target activity was observed for both G10 and trG10 at a top-scoring intergenic site (OT1, chr9: 104,595,865, 55% indel formation), which lies ~3 kb from the nearest annotated genic sequence. Off-target activity was detected with G10 at the other intergenic site (OT2, chr17: 66,624,238, 0.30%), but this was absent with the truncated guide trG10. Low but detectable off-target activity was observed with both the G10 and trG10 RNPs at two exonic off-targets, FSCN3 and GTDC2. Indel formation was lower for the full-length G10 RNP. (FSCN3: 0.013% and 0.16% indel for G10 and trG10 respectively; GTDC2: 0.025% and 0.035% indel for G10 and trG10, respectively). Very few indels were observed at HBD (0.010% and 0.011% indel for G10 and trG10 respectively) and indels at other ß-globin genes (HBE1, HBG1, HBG2) were not detected over background (FIG. 9E).

Optimizing Candidate Cas9 RNPs and ssODNs to Edit CD34+ HSPCs

The results of RNP editing in K562 cells encouraged the investigation of this approach in HSPCs, recognizing that editing outcomes can differ between cell types. The trG10 sgRNA was used, which showed robust HDR and few off-target effects in K562, and HDR in adult mobilized peripheral blood HSPCs (which are the cells most relevant for therapeutic gene editing to address SCD) was re-optimized. Since these cells were obtained from healthy wild-type (WT) donors, the initial experiments used ssODNs bearing a WT-to-SCD mutation.

Figure 15A:
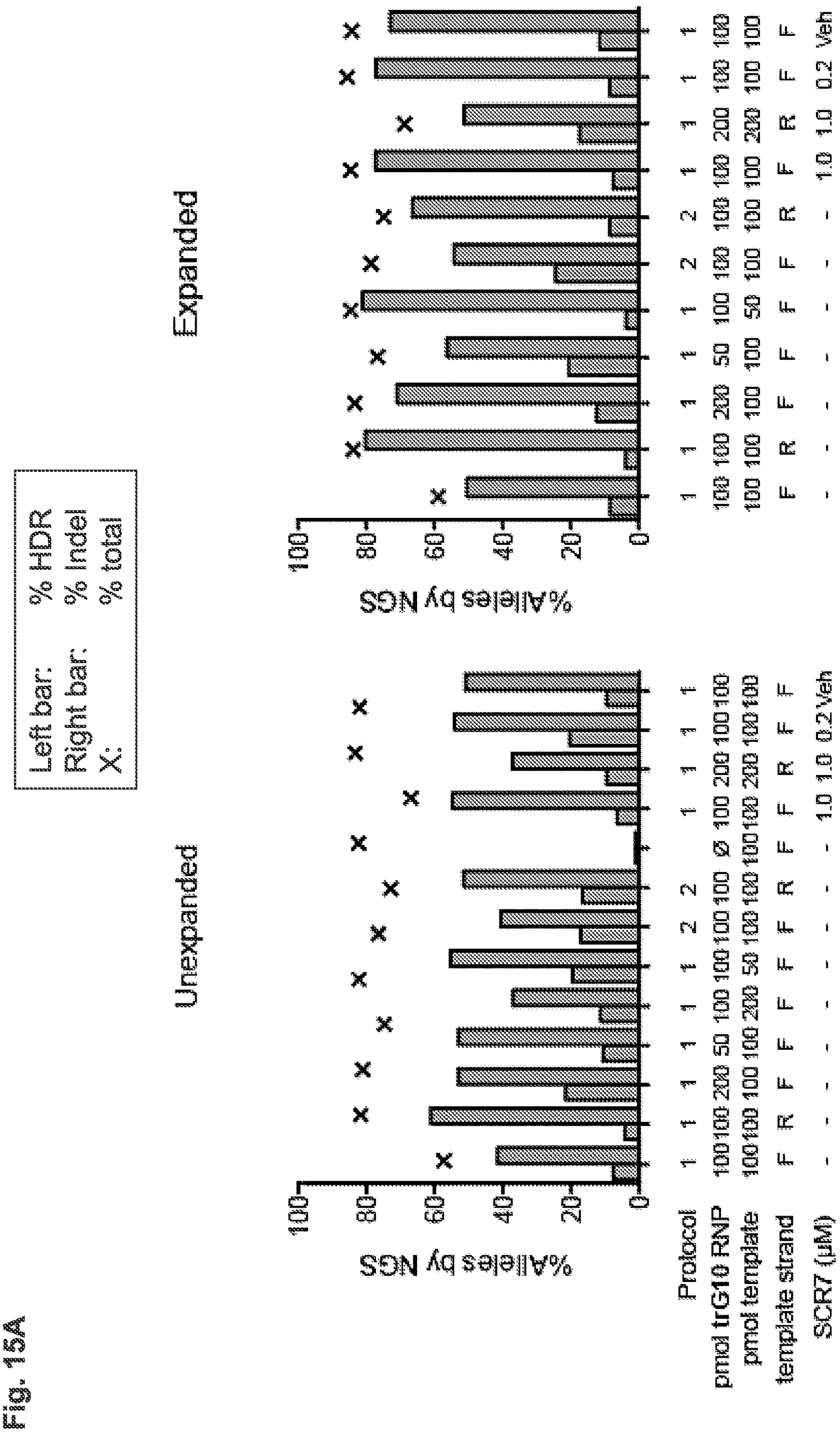
FIG. 15A-15E depict data related to FIG. 10.
Figure 15B:
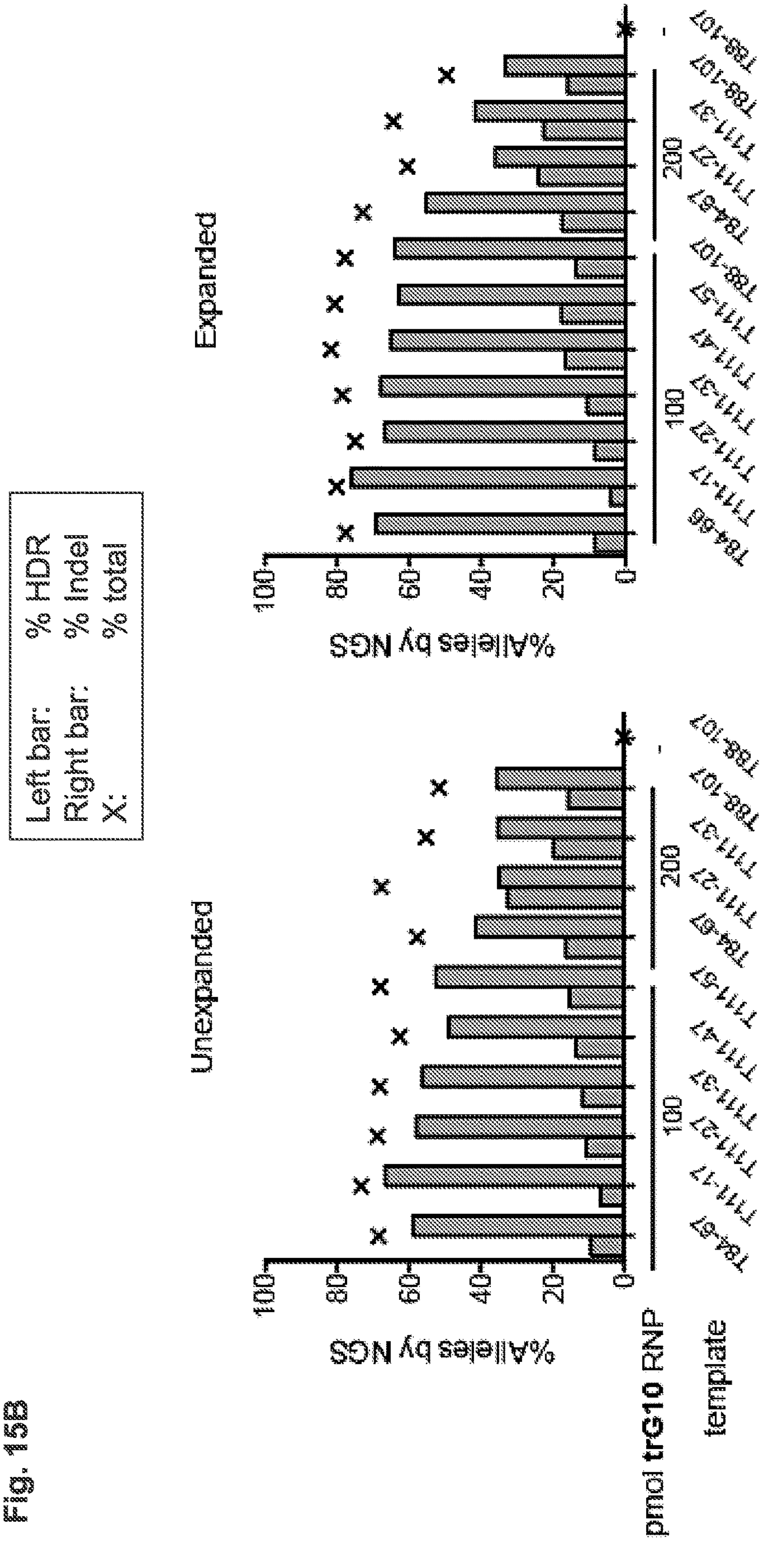

Electroporation conditions, template design, and RNP/ssODN dose were first optimized in HSPCs (FIG. 15A-15B). To selectively interrogate editing in viable cells, NGS was used to assay HSPCs cultured in erythroid expansion conditions for 7 days after editing (erythroid-expanded), along with edited HSPCs cultured for only 2 days (un-expanded). During initial treatments, treatment with even 100 pmol of RNP led to significant decline in viability, and so 75 pmol RNP was used in subsequent in vitro experiments (FIG. 10). In addition, the effects of the small molecule SCR7 on editing in HSPCs were tested. This NHEJ inhibitor has been reported to increase HDR-mediated editing in some cell types, but an improvement in HDR in HSPCs was not observed here (FIG. 15A).

FIG. 15A-15E depict data related to FIG. 10. A) Editing outcomes of un-expanded HSPCs (cultured for 2 days after editing in HSC expansion medium) and erythroid-expanded (cultured for 5 additional days in erythroid expansion medium) HSPCs after electroporation with the indicated doses of templates, trG10 RNP, and Scr7 (NHEJ inhibitor), and either protocol 1 (Lonza DO100) or protocol 2 (Lonza ER100). Either forward-strand matching (F) or reverse strand-matching (R) templates (template T88-107, and its reverse complement) were provided as indicated. B) Editing outcomes of HSPCs cultured in non-expanding and erythroid-expanded conditions, assessed by NGS. CD34+ HSPCs were edited with indicated templates and RNPs, and protocol 2. C) Viable cell counts of HPSCs 24-144 house after treatment with indicated electroporation protocol and dose of RNP (except untreated cells). Error bars indicate s.d. of 3 biological replicates for each condition. D) Genotyping of HSPCs by ddPCR. HSPCs (3 biological replicates) were edited with the indicated doses of trG10 RNP, along with the indicated asymmetric template, and cultured in non-expanding conditions for 2 days prior to genotyping by ddPCR (see Methods). Error bars indicate the SEM of the means from three technical replicates of three biological replicates, from a single healthy donor. E) Conversion of coding sequence of HBB to HBD, for HSPCs edited and cultured as in FIG. 10A, assessed by NGS.

Figure 10B:
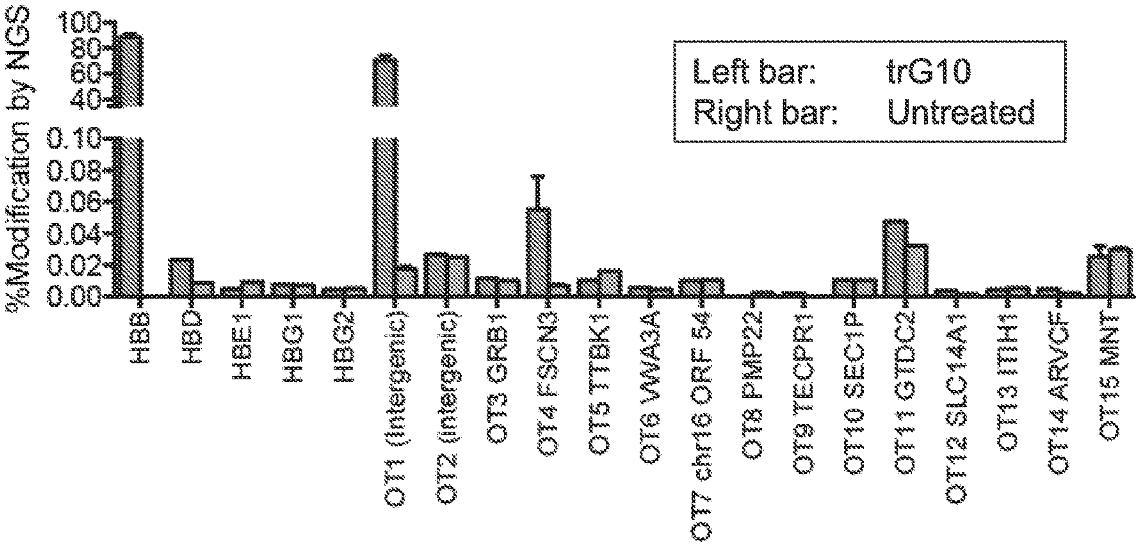
Figure 10C:
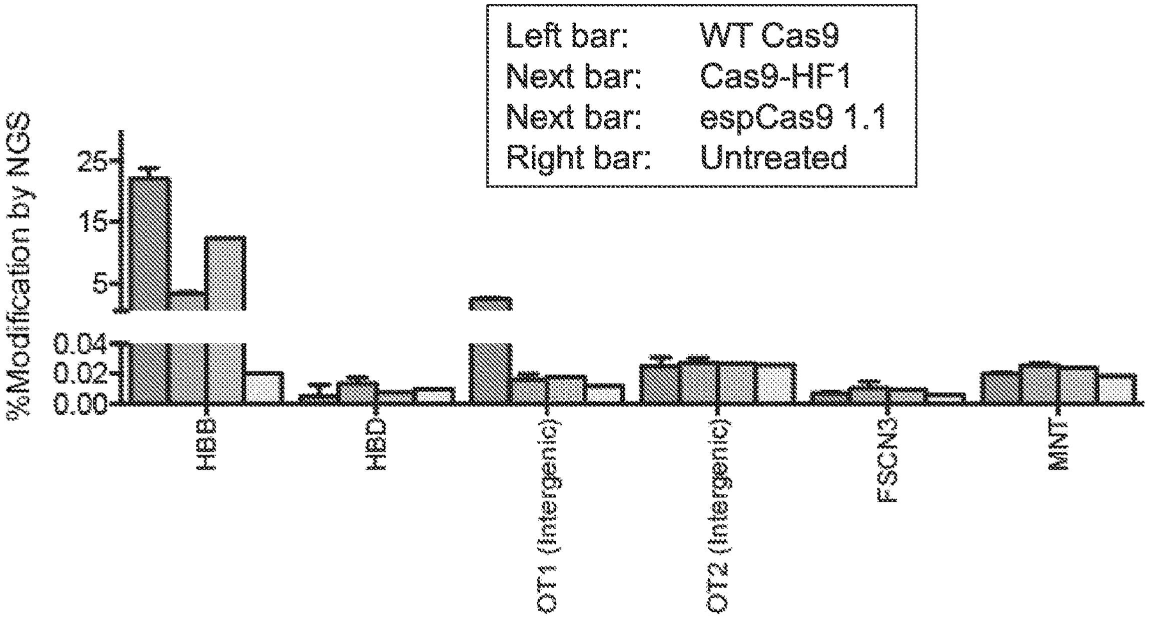

FIG. 10A-10C. Editing of wild-type human CD34+ HSPCs by the Cas9 RNP. A) Analysis of editing in un-expanded HSPCs (left) and erythroid-expanded HSPCs (right), using trG10 RNP and conditions as indicated. Templates, which are asymmetric about the G10 cut site, are designed as described in the text. All samples are 3 biological replicates, error bars are ±standard deviation B) Modification (HDR+Indel) at off-target sites in HSPCs edited with the trG10 RNP and template T88-107, compared to untreated cells. Samples for HBB, OT1, FSCN3, and MNT are from 3 biological replicates, with error bars±standard deviation. Targets were selected using the online CRISPR-design tool. C) Indel formation at on- and off-target sites by Cas9 mutants with increased specificity (HF1 and espCas9 1.1), in HSPCs, compared to WT Cas9, all complexed to the G10 sgRNA and no ssODN. The absence of an ssODN reduced indel formation overall. All samples are n=3 biological replicates, with error bars±standard deviation.

Figure 15C:
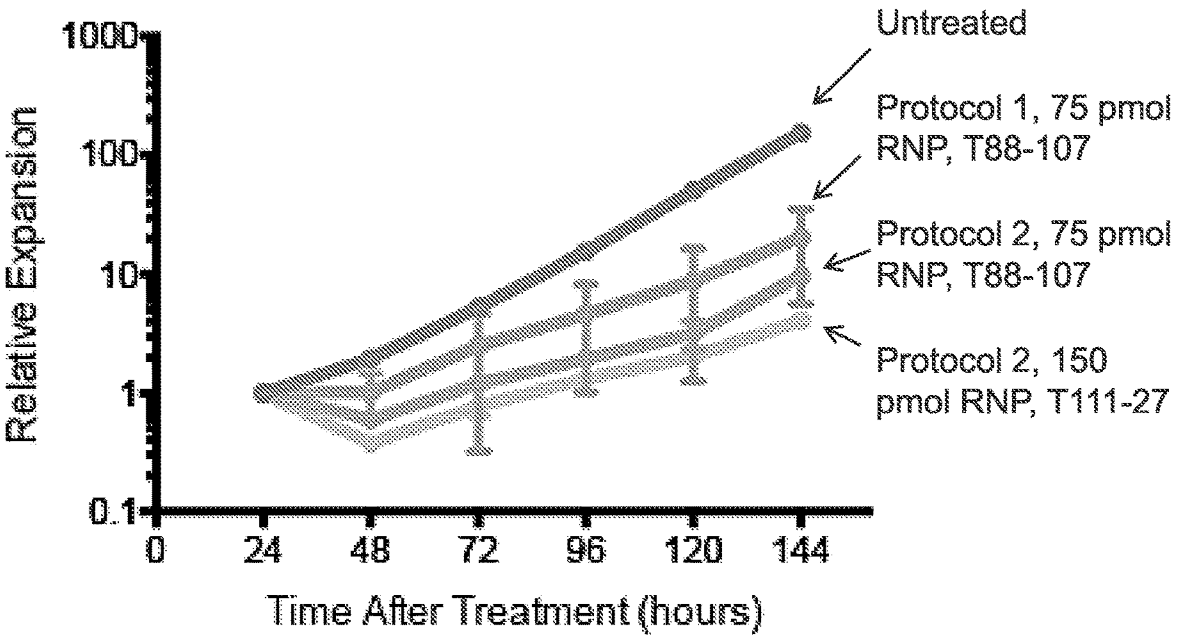
Figure 15D:
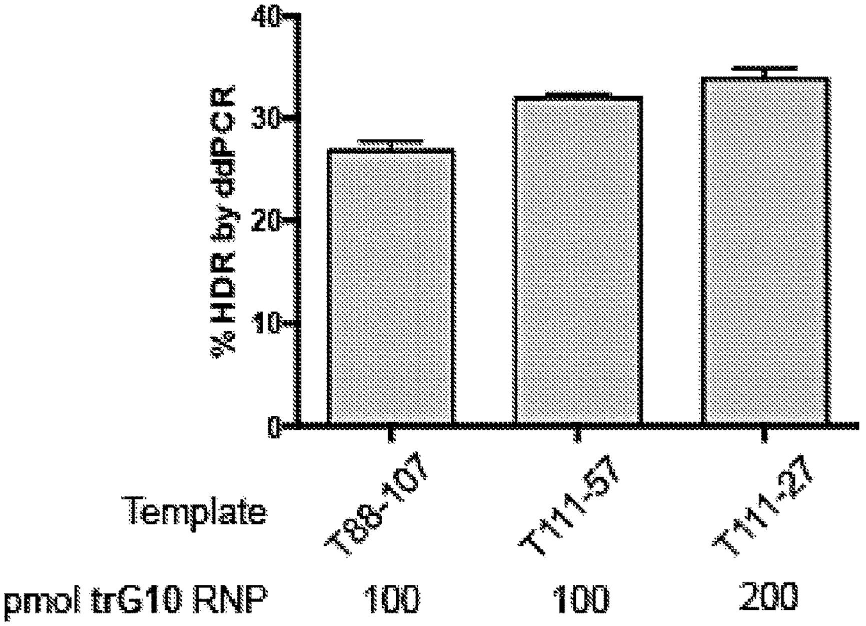
Figure 15E:
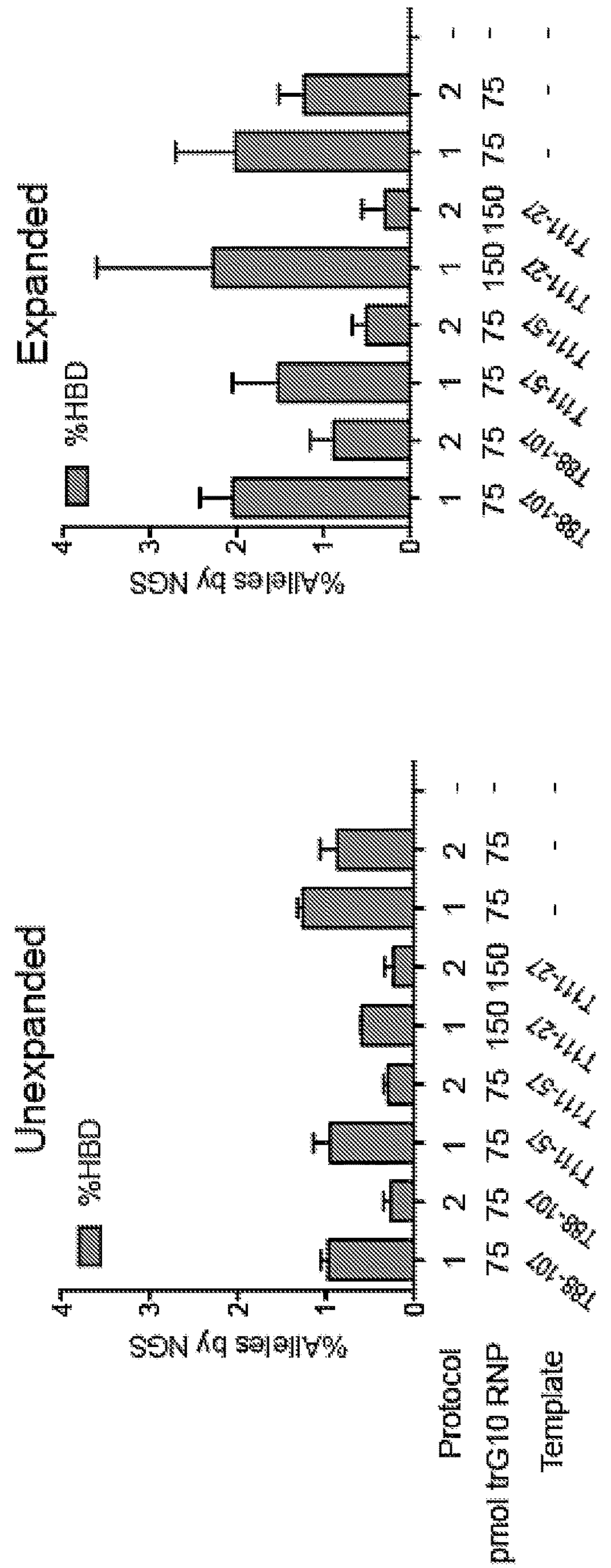

Appreciable initial levels of total editing were obtained at the sickle SNP in HSPCs, with HDR rates between 6-11% (FIG. 10A and FIG. 10B). After 5 days of erythroid expansion, HDR rates increased, with up to 33% editing at both high and low doses of RNP (150 and 75 pmol respectively). Total editing in expanded HSPCs was between 66 and 72%, indicating good delivery of the trG10 RNP to HSPCs. In general, higher editing was accompanied by some reduction in viability as measured by fewer viable cells remaining post-treatment, particularly at a 150 pmol dose of RNP (FIG. 15C). The asymmetric ssODN that was most effective in K562 cells (T111-57) drove HDR more efficiently at a lower Cas9 dose of 75 pmol RNP per 150,000 HSPCs, while a shorter template (T111-27) was more efficient at a higher dose of Cas9 (150 pmol RNP per 150,000 HSPCs) (FIG. 10A). In a separate experiment, high rates of HDR were confirmed in by ddPCR (FIG. 15D). These experiments demonstrate efficient in vitro editing of CD34+ HSPCs using the Cas9 RNP, including HDR-mediated sequence replacement using ssODNs without a selection marker. As was the case with K562 cells, in HSPCs low but measureable conversion of HBB coding sequence to HBD (0.2 to 2%) was detected, and rates of conversion increased after expansion of edited cells (FIG. 15E).

To analyze how allele frequencies in the HSPC population translate to the editing of alleles in individual HSPCs, the best editing condition was repeated in CD34+ HSPCs (75 pmol trG10 RNP and 100 pmol T111-57), the cells were recovered in HSPC expansion media for two days, and single edited HSPCs were plated by limiting dilution in erythroid expansion medium. After 14 days of growth, 96 edited clones were individually genotyped by multiplexed next generation sequencing (FIG. 19). In this experiment 21% HDR alleles were observed in the cell pool. However, these alleles were spread across 32% of cells. This increased prevalence of edited cells relative to edited alleles is predicted by the independent assortment of alleles within a population (although homozygous genotypes were still slightly overrepresented relative to prediction) and increases the potential benefit of a gene editing therapy for recessive diseases such as SCD.

Off-target activity of the trG10 RNP in HSPCs were analyzed using the target selection criteria described above for K562 cells (FIG. 10B). Most predicted genic off-targets showed no detectable indel formation, although cutting at the previously observed intergenic site remained high (OT1, 44% indel). The sites of off-target cleavage observed in HSPCs generally corresponded to observations in K562 cells, though the rates were often reduced (for example, FSCN3 ~0.05% in HSPCs vs. up to 0.16% in K562s).

As an additional test of the effects of off-target activity of the trG10 RNP, over-amplification PCR was used to detect the presence or absence of translocations between the on-target site at HBB and selected off-target sites (OT1, HBD, FSCN3, and MNT), in both K562 cells and HPSCs edited with trG10 (FIG. 16). Translocations between OT1 and HBD with HBB were observed in K562 cells. Translocations may have occurred between OT1 and HBB in HSPCs as well, but at a much lower frequency.

Figure 16A:
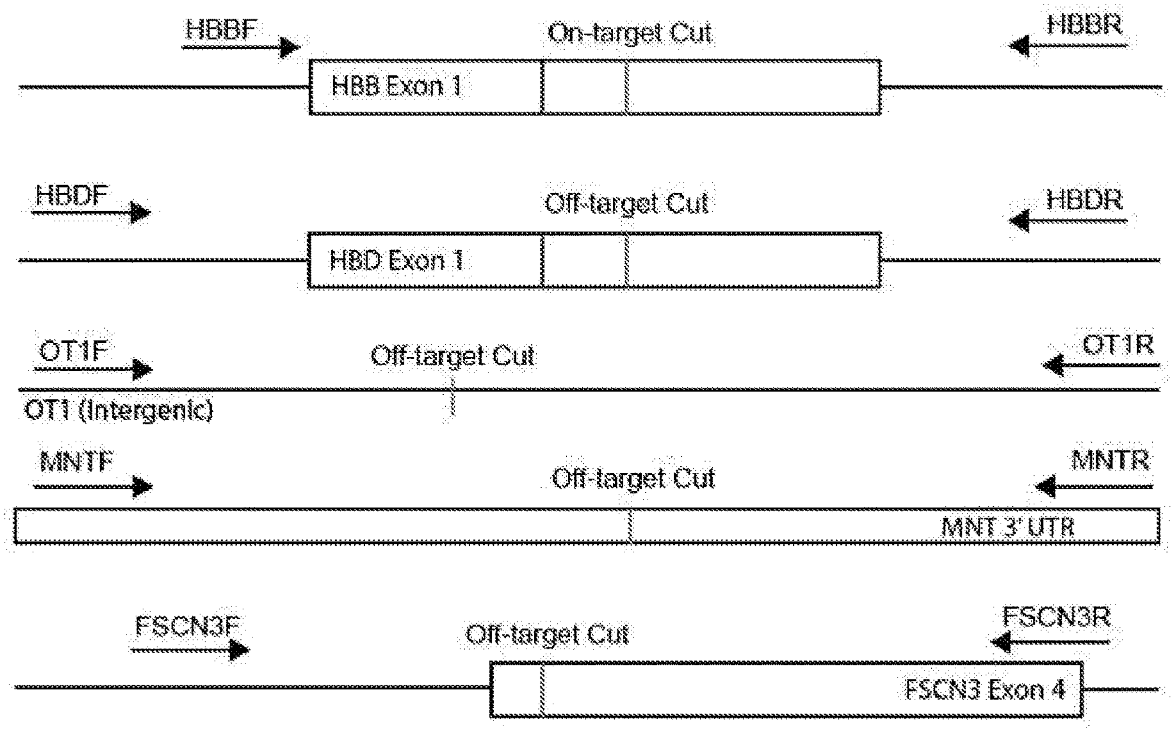
FIG. 16A-16C depict data related to FIG. 10—qualitative detection of chromosomal translocations by over-amplification PCR.
Figure 16B:
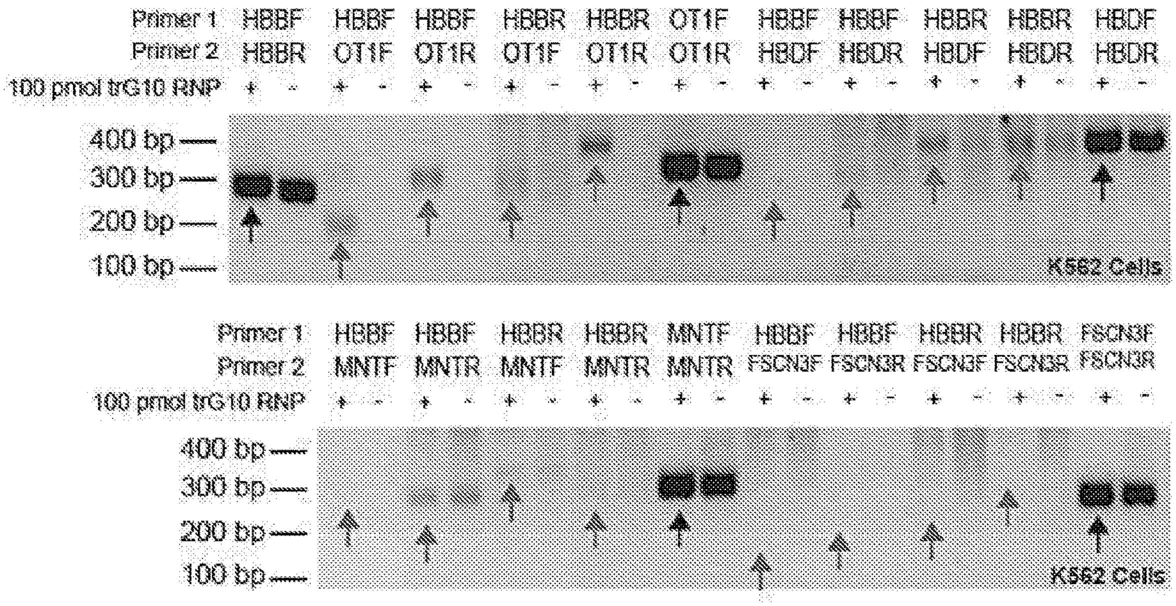
Figure 16C:
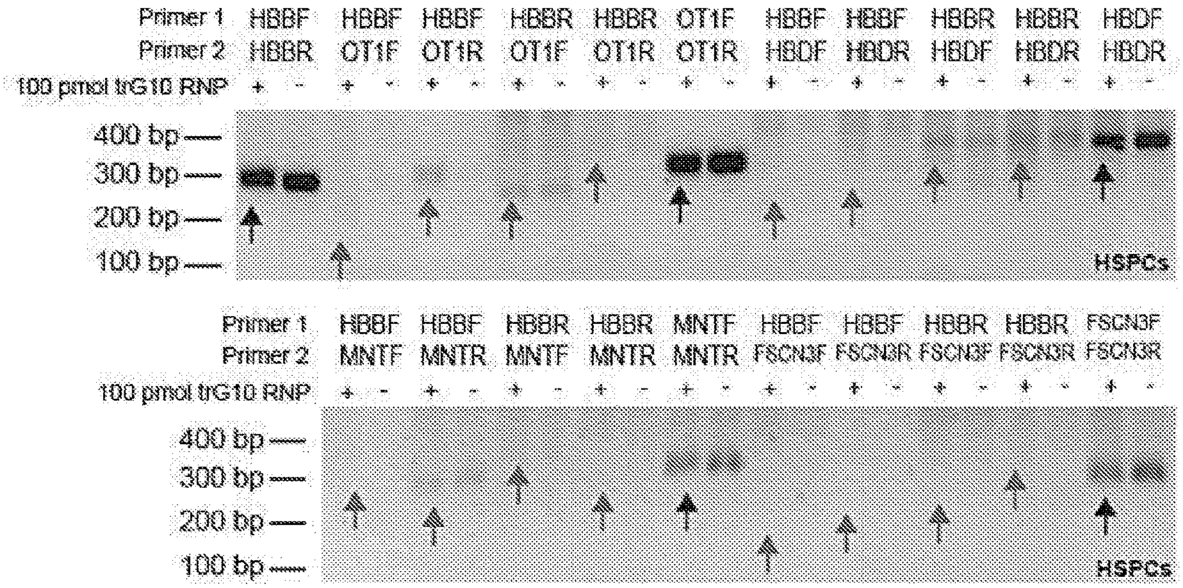

FIG. 16A-16C depict data related to FIG. 10—qualitative detection of chromosomal translocations by over-amplification PCR. A) Schematic depicting primers used to detect chromosomal translocations between HBB (on-target), HBD, OT1 (intergenic), FSCN3, and MNT. B-C) 2% agarose gel depicting translocations between on- and off-target sites in K562 cells and HSPCs edited with the trG10 RNP, compared to untreated cells. Arrows indicate trG10-presence (red arrows) or absence (green arrows) of trG10-dependent translocations, and positive controls (black arrows). Translocations between OT1 and HBD are observed in K562 cells. One translocation between OT1 and HBB is observed in HSPCs, but not between HBB and the other sites.

It was also tested whether trG10 has off-target activity at cancer-associated genes. Though these sites bear little similarity to the trG10 protospacer, even low levels of activity in such locations would be dangerous. A capture library (Illumina TruSight Cancer, see Methods for details) was used to sequence several hundred loci to about 8,000 fold coverage each. Relative to unedited cells, a small number of indel mutations were found enriched in K562 cells edited with the trG10 RNP, typically at less than 1% of alleles (FIG. 20). Almost all of these mutations were present in unedited cells, but are reported here because the mutation frequencies slightly increased after editing. In stark contrast, no indels were detected at cancer-associated genes in similarly edited HSPCs. These results highlight the importance of performing rare off-target event detection in the target primary cell type and suggest that the trG10 RNP may not have substantial genotoxic liabilities, although this can still be tested further through rigorous functional determination of genotoxicity using experiments such as serial transplantation and clinical scale engraftment.

Two mutant variants of the Cas9 protein have recently been reported to reduce off-target effects in cell lines, even at sites with relatively few PAM-distal mismatches, such as OT1 for the G10 sgRNA's intergenic OT1 off-target site. eSpCas9-1.1 and HF1 variants of Cas9 were expressed and purified, and were paired with the G10 sgRNA to form RNPs, which were used to edit wild type CD34+ HSPCs in the absence of an ssODN. NGS was used to determine the on- and off-target editing frequencies (FIG. 10C). As expected, for all enzymes the on-target indel formation was reduced in the absence of an ssODN (FIG. 10B vs 10C). Compared to wild type Cas9, both HF1 and eSpCas9-1.1 showed even further decreased on-target indel formation at the HBB locus, including an almost five-fold decrease in indels for HF1. However, both modified enzymes also completely eliminated all previously observed off-target events, including the prevalent OT1 intergenic off-target (FIG. 10C).

Figure 11A:
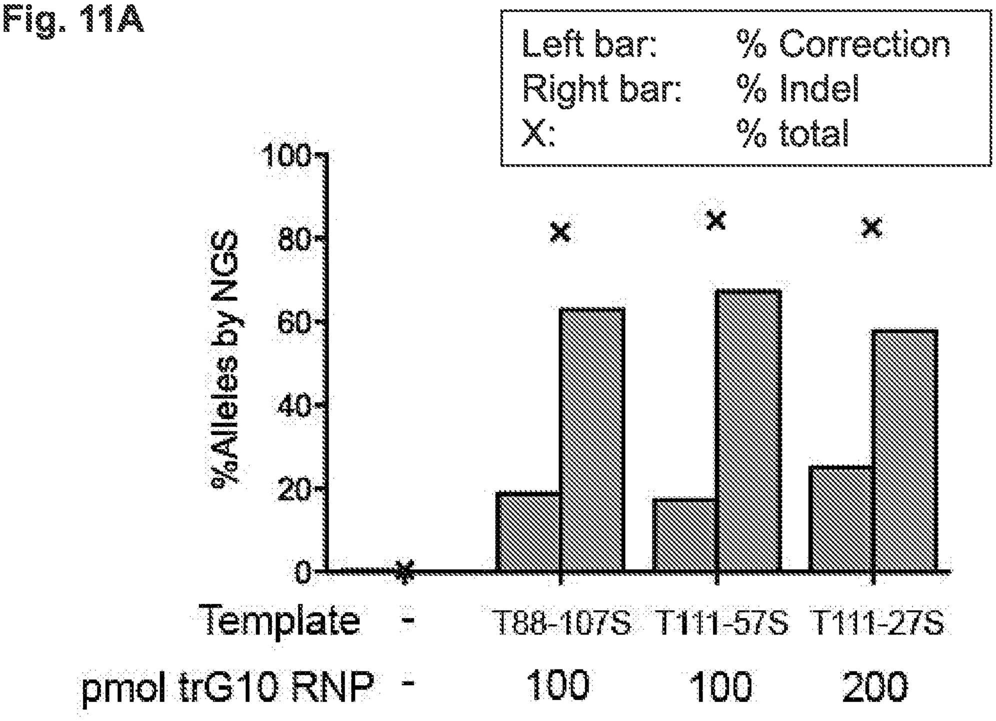
FIG. 11A-11D depict data related to correction of the SCD mutation in SCD HSPCs.
Figure 11B:
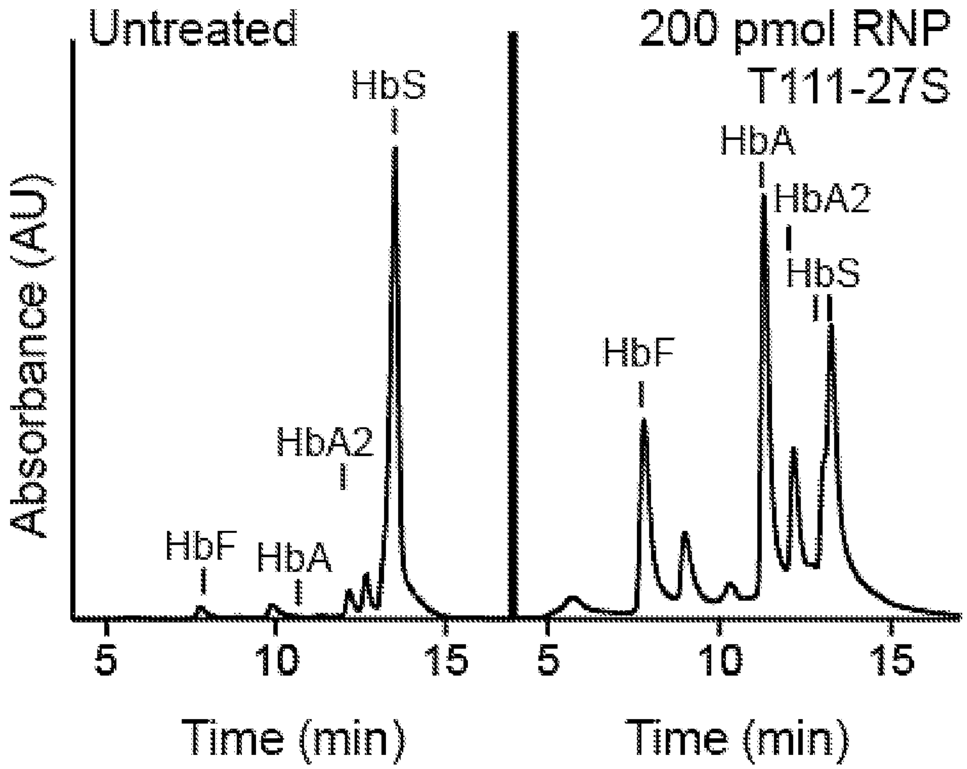
Figure 11C:
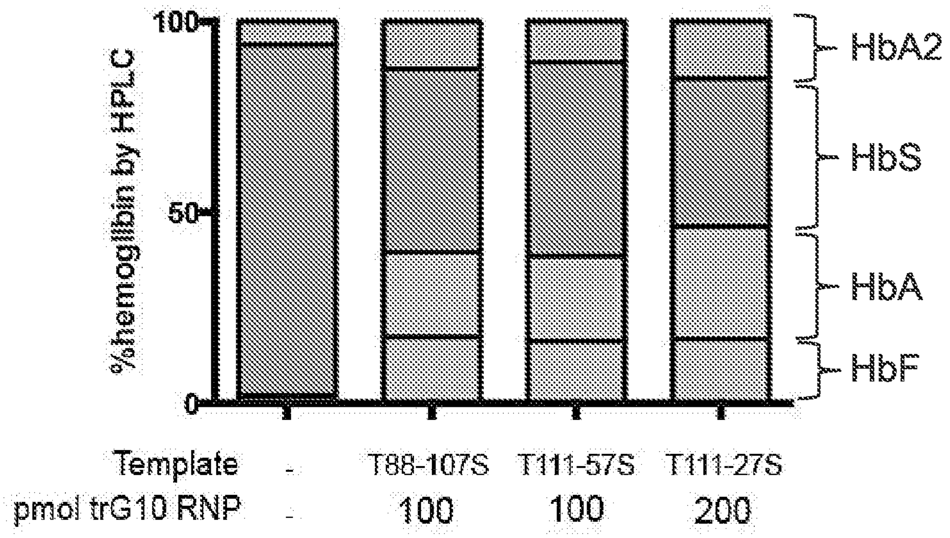

Correction of the SCD Mutation in HSPCs Leads to Production of Wild Type Hemoglobin The success in WT-to-SCD editing in HSPCs implies that the same method can be used to edit SCD to WT in HSPCs derived from SCD patients. Since human erythropoiesis does not occur when human HSPCs are xenografted into mice, and the availability of SCD HSPCs is limited, the effects of correcting the SCD mutation in HSPCs were evaluated in vitro, by carrying out erythroid differentiation of edited HSPCs. $CD34^+$ HSPCs were obtained from whole blood discarded after exchange transfusion of SCD patients. Since the HF1 and eSpCas9-1.1 proteins yielded reduced levels of on-target editing and the predominant off-target from wild type Cas9 lies in an intergenic region with no known function, the focus was on experiments using the most efficacious wild type Cas9. The SCD mutation was corrected using the trG10 RNP and ssODNs carrying an SCD-to-WT edit. These SCD-to-WT templates, denoted by the suffix "S", encode the same number of mutations as the WT-to-SCD templates, with the base identity different only at the SCD SNP. Measuring editing by both NGS and ddPCR, the SCD HSPCs were edited at levels similar to those observed in WT HSPCs from mobilized blood, with up to 25% of alleles corrected to WT at high RNP dose and 18% corrected at low RNP dose (FIG. 11A and FIG. 17).

FIG. 11A-11D depict data related to correction of the SCD mutation in SCD HSPCs. A) Editing the SCD mutation in un-expanded CD34+ HSPCs from the whole blood of SCD patients, assessed by NGS. B) HPLC trace depicting hemoglobin production in SCD HSPCs edited with 200 pmol of the trG10 RNP and the T111-27S donor, compared to untreated HSPCs, after differentiation into erythroblasts. Significant increases in HbA, HbF, and HbA2 are apparent. C) Stacked bars showing HPLC results, with HSPCs edited as indicated prior to differentiation into erythroblasts. D) Globin gene levels in SCD HSPCs edited as in FIG. 11C, determined by RNA-seq.

Figure 17:
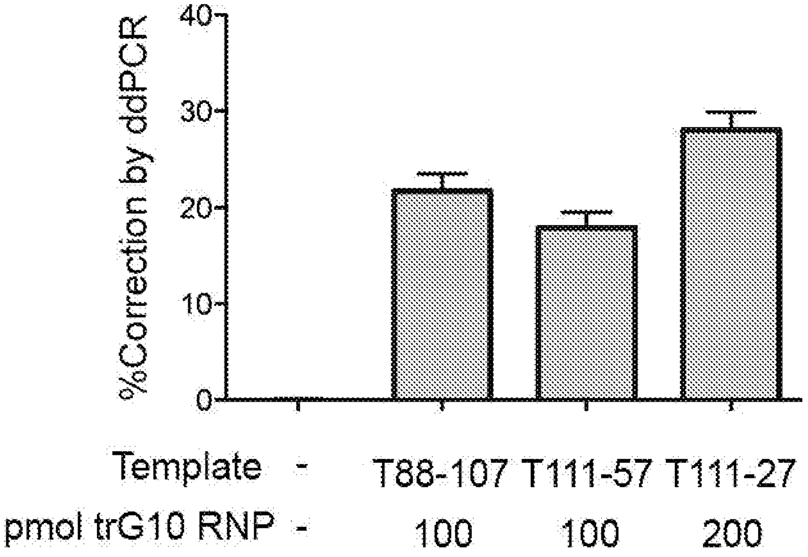
FIG. 17 depicts data related to FIG. 11—HDR-mediated correction of SCD HSPCs, assessed by ddPCR.

FIG. 17 depicts data related to FIG. 11—HDR-mediated correction of SCD HSPCs, assessed by ddPCR. HSPCs from SCD patients were edited with indicated templates and the trG10 RNP, and cultured for 2 days in non-expanding conditions (identical to conditions in FIG. 11). Editing was then assessed by ddPCR of genomic DNA extracted from edited cells, using TaqMan probes for the SCD (unedited) and WT (edited) alleles.

To analyze the hemoglobin production potential of corrected HSPCs, pools of treated HSPCs were differentiated into enucleated erythrocytes and late-stage erythroblasts; and hemoglobin was measured by HPLC. Corrected HSPC pools produced substantial amounts of wild-type adult hemoglobin (HbA), with a concomitant decrease in sickle hemoglobin (HbS) (22.2%-22.4% HbA, 48.0%-50.6% HbS at low-dose RNP, 29.3% HbA, and 38.7% HbS at high-dose RNP). A substantial increase in fetal hemoglobin (HbF) was also observed in edited cell pools (16.3%-17.4% HbF in edited cells vs 2.0% HbF in unedited cells).

Figure 11D:
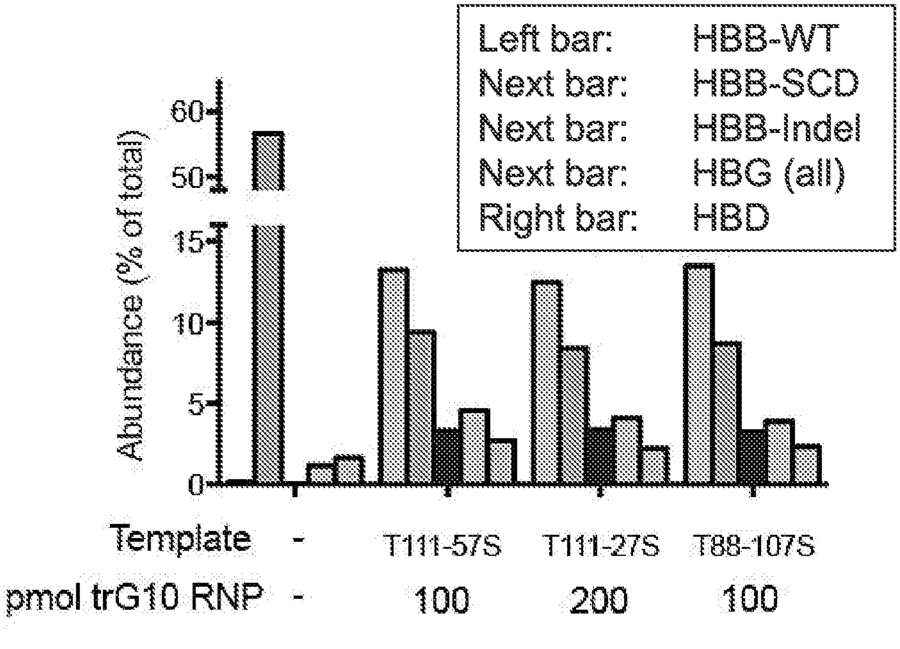

RNA-seq was used to measure globin transcript abundance in pools of edited SCD HSPCs differentiated to erythrocytes. Globin transcript levels showed a trend similar to protein levels after editing, with sickle HBB transcripts decreasing from 56.7% of all transcripts to ~9% and wild-type HBB transcripts increasing from 0.1% to 13% across all three editing conditions (FIG. 11D). Consistent with the increase in HbF protein, a ~3-fold increase in the expression of □-globin (HBG1 and HBG2) mRNA was observed. Thus, corrected pools of cells produce decreased sickle β-globin, increased adult wild-type ß-globin, and increased fetal β-like (□) globin.

Edited HSPCs Repopulate In Vivo

The trG10 Cas9 RNP and an ssODN donor template can efficiently edit the SCD mutation in CD34+ HSPCs, and erythrocytes derived from these cells have altered hemoglobin levels consistent with substantial gene correction. In order for gene correction to manifest in vivo, edited re-populating stem cells must engraft and repopulate within a recipient. A powerful method of assaying re-populating stem cells is through long-term xenograft in an immunodeficient mouse model, such as the NOD/SCID/IL-2rγ$^{null}$ (NSG) mouse. In this model, edited human stem cells must engraft in the mouse and persist over several months. After sixteen weeks, progenitor cells should be lost from the system and human cells in the bone marrow will be derived from long-term re-populating stem cells within the initial HSPC population. Since SCD HSPCs are difficult to obtain at the necessary scale, wild-type HSPCs were edited to SCD and were implanted in NSG mice.

Figure 12A:
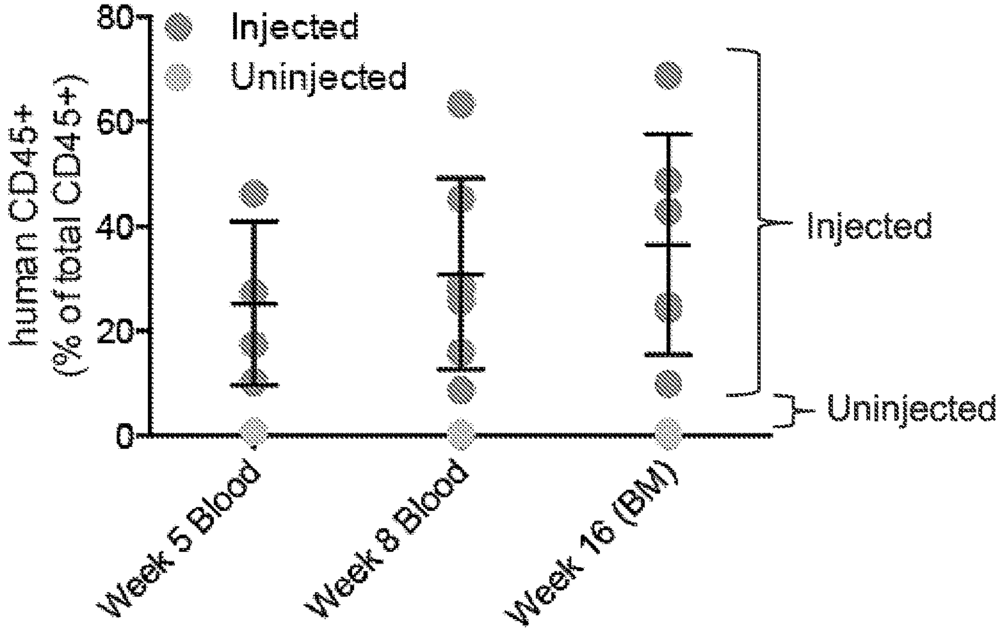
FIG. 12A-12D depict data related to engraftment of edited HSPCs into NSG mice.
Figure 12B:
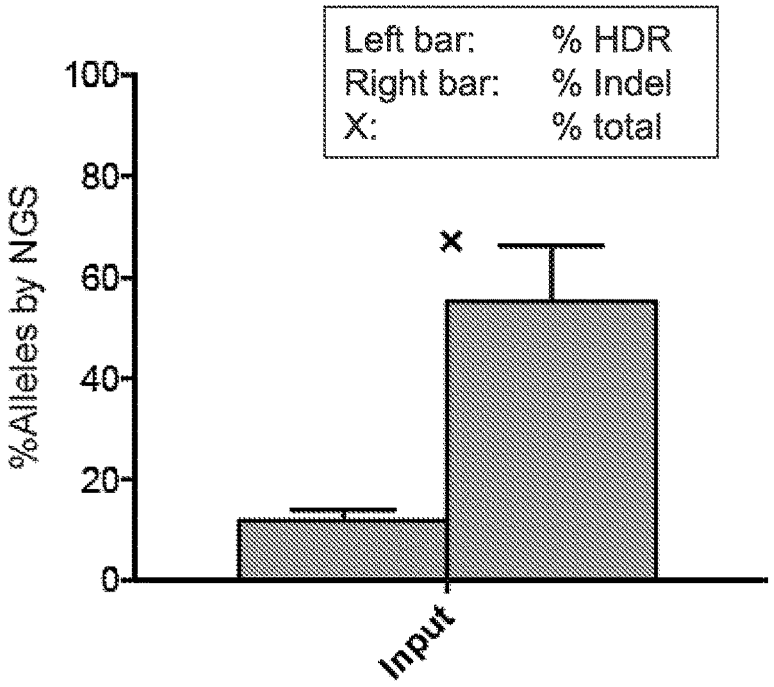

NSG mice were injected with pools of WT CD34$^+$ HSPCs edited with the trG10 RNP and the T88-107 template (7 mice over three treatments, $1\times10^6$ cells per mouse) (two NSG mice were not injected. Engraftment was monitored by fluorescence activated cell sorting (FACS) analysis of blood draws at five and eight weeks post-injection. Final engraftment was assessed at sixteen weeks post-injection, when mice were sacrificed and bone marrow (BM) cells were harvested and subjected to FACS-based lineage analysis (6 mice, FIG. 12A and FIG. 18). Substantial numbers of hematopoietic (CD45$^+$) cells were detectable in BM of all injected mice at 16 weeks (37%±21% human CD45, mean±s.d.), demonstrating that edited cells maintain long-term repopulating potential. Within BM, engrafted human CD45$^+$ cells were primarily B cells (CD19$^+$, 57%±18%, mean±s.d.), along with a significant minority of myeloid cells (CD33$^+$, 25%±18%, mean±s.d.) (FIG. 18B).

FIG. 12A-12D depict data related to engraftment of edited HSPCs into NSG mice. A) Engraftment of human CD45$^+$ cells in NSG mice injected with edited HSPCs, compared to 2 un-injected mice. B) Analysis by NGS of editing at the SCD SNP in cells prior to engraftment. Error bars indicate mean±standard deviation of three separate experiments with cells from two healthy donors. C) HDR-mediated editing (left) and indel formation (right) at the SCD SNP in human cells engrafted in mouse blood, spleen, and bone marrow (BM), at 5 and 16 weeks post-injection. Error bars indicate mean±standard deviation over either 6 mice (spleen) or 7 mice (BM and blood).

Figure 18A:
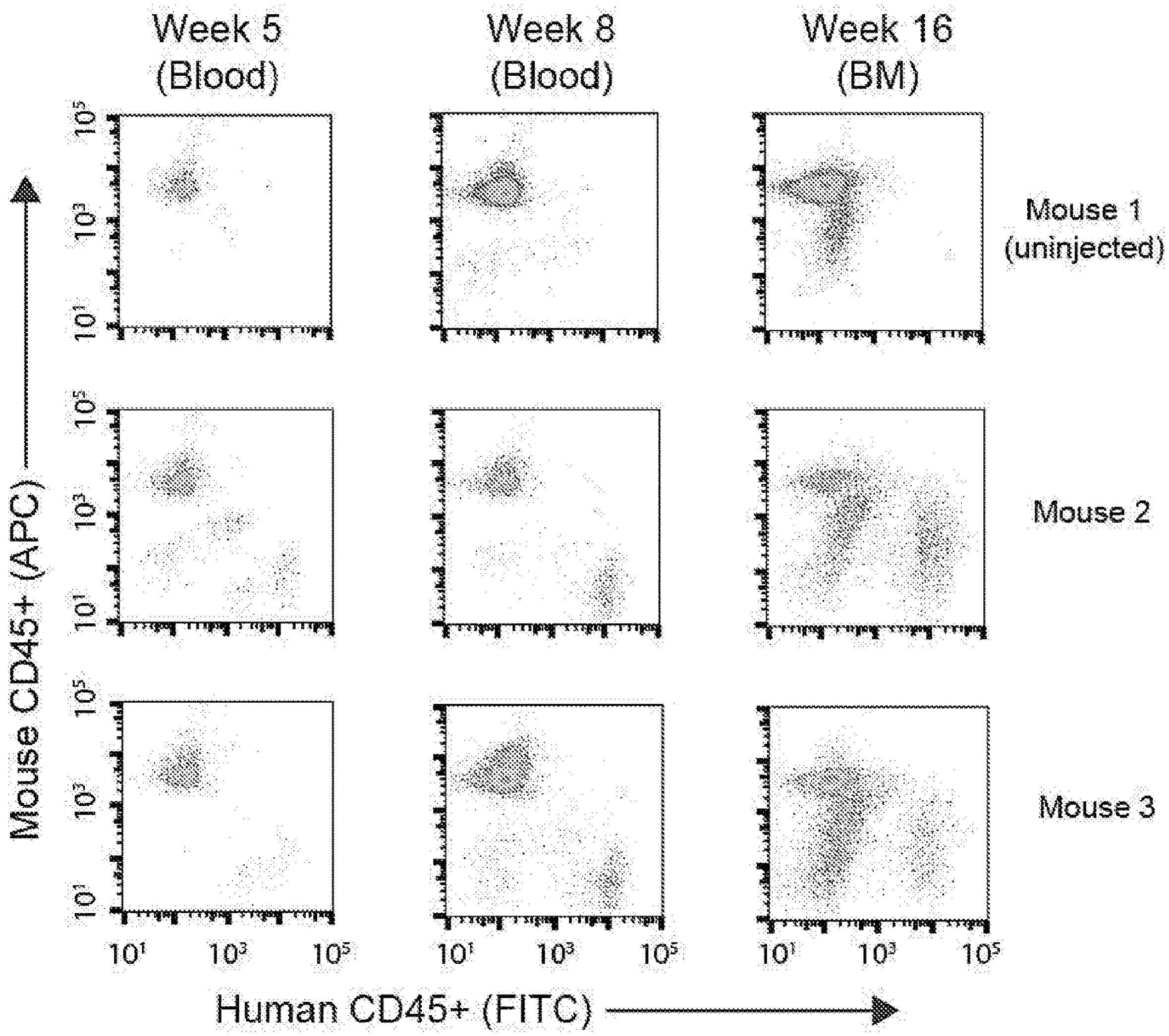
FIG. 18A-18C depict data related to FIG. 12.
Figure 18B:
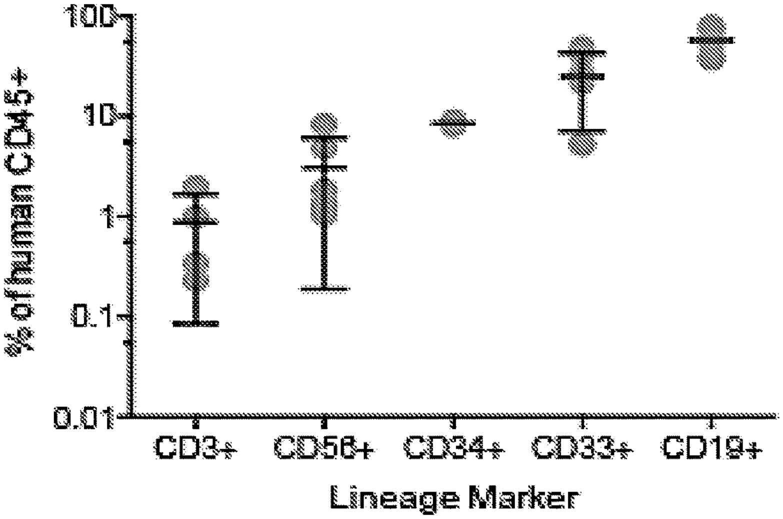

FIG. 18A-18B depict data related to FIG. 12. A) FACS plots depicting engraftment of edited HSPCs in NSG mouse. Mice were engrafted with either no cells (Mouse 1), or edited HSPCs (Mice 2-3). At indicated times, engraftment in either blood or bone marrow (BM) was determined by immunostaining and FACS analysis with human anti-CD45-FITC and mouse anti-CD45-APC. B) Lineage characterization of engrafted human cells. Bone marrow from mice 16 weeks post-injection was harvested, stained with antibodies against indicated human-specific markers along with human CD45. Error bars represent Mean±s.d. over four mice. C) Editing data as in FIG. 12C-12D, including indel and HDR within the CD34+ (progenitor) and CD19+ (B lymphocyte) compartments of the marrow of two mice, 16 weeks after injection.

Figure 12C:
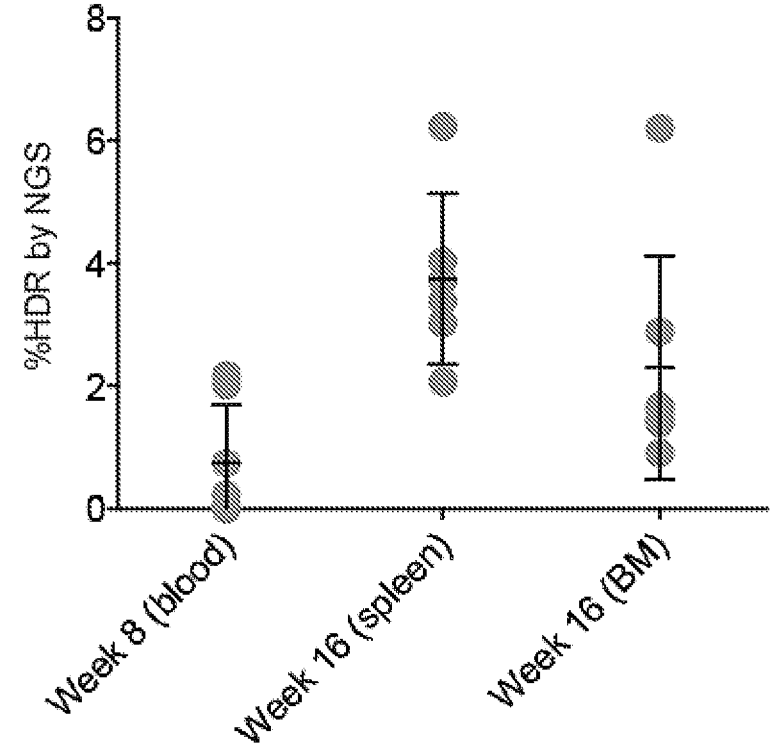
Figure 12D:
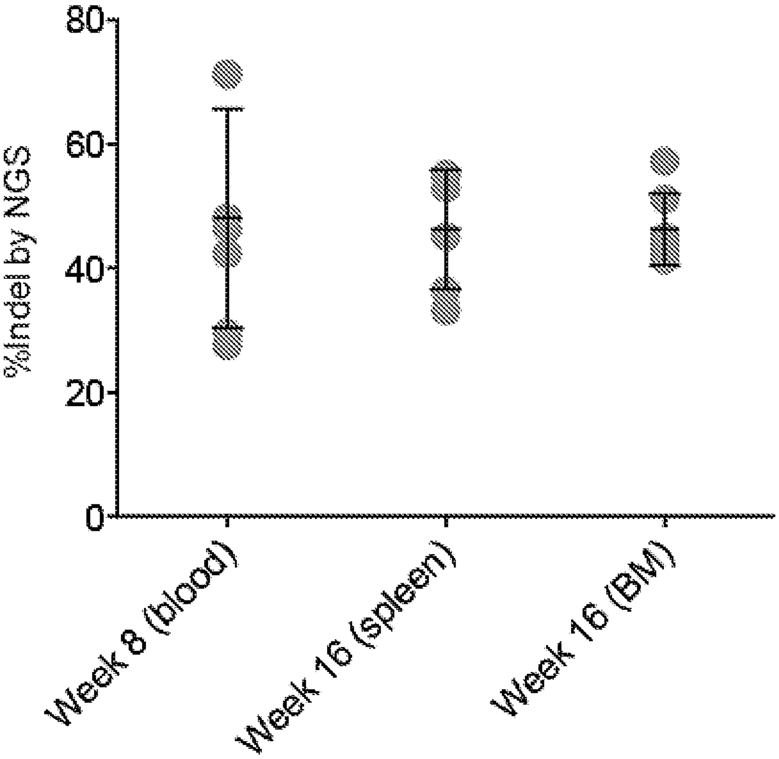
Figure 18C:
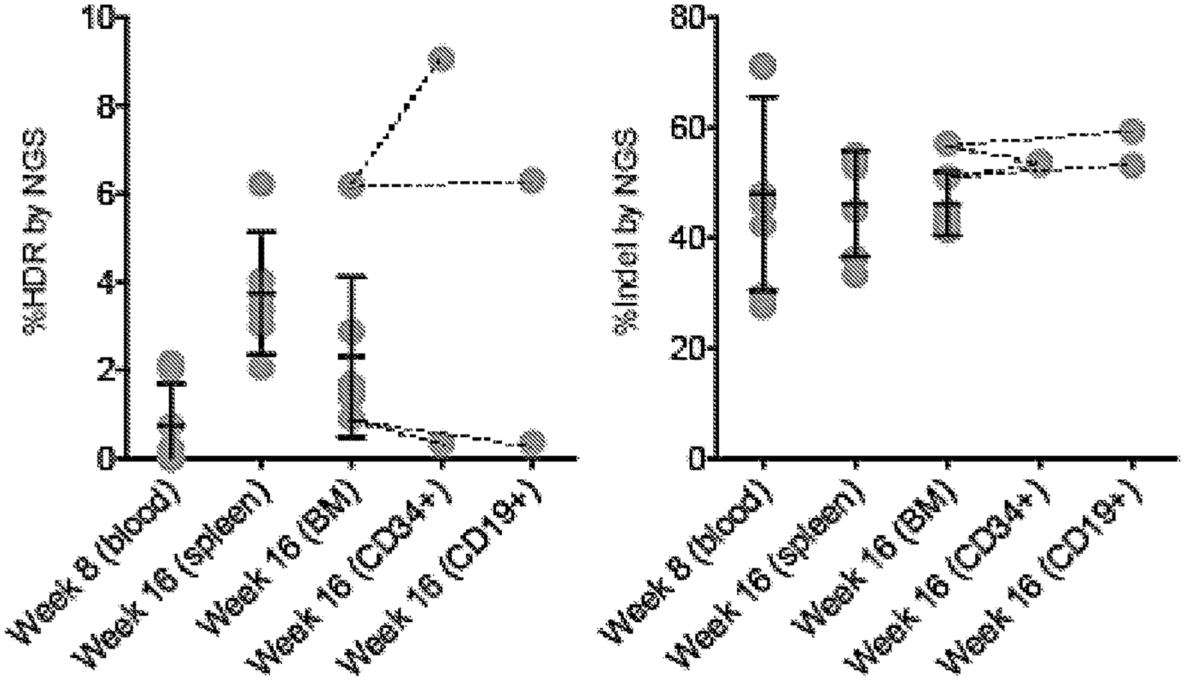

Genotyping of edited HSPCs was assessed by NGS immediately after editing and prior to injection (FIG. 12B), and from mice at weeks 8 (blood) and 16 (BM and spleen, FIG. 12C-12D). The input populations had 55%±19% indel alleles and 11.8%±3.7% HDR alleles (mean±s.d., FIG. 12B). NGS analysis revealed consistently high levels of indel alleles (46±6% in BM, mean±s.d.), along with maintenance of HDR-mediated editing at the SCD SNP throughout the lifetime of the xenograft in both BM and spleen (2.3±1.8% in bone marrow, 3.7±1.4% in spleen, mean±s.d.). Human cells engrafted in one mouse maintained HDR-mediated editing in BM at a remarkably high level (6.2%), although the reasons for this difference are unclear. To ensure that editing was present in the progenitor (CD34$^+$) cells and not over-represented in the B lymphocyte (CD19$^+$) populations, marrow from two mice was sorted for these markers and genotyped by NGS. Editing was maintained within both populations, indicating durable editing of the long-term stem cell (HSC) population (FIG. 18). Despite the decreased HDR rate, this level of sequence replacement using Cas9 RNP and ssODNs is more than 9-fold greater than previously reported editing of the SCD mutation in HSCs using ZFN mRNA electroporation and ssODNs.

FIG. 21. Estimates of cellular editing in mice engrafted with edited HSPCs, from measurement of allelic editing in bone marrow by NGS, 16 weeks post-injection. Estimates were calculated using the Hardy-Weinberg equation: $(p^2+q^2+r^2)=1$.

The approach described here allows researchers to edit SNPs at endogenous loci in human adult HSPCs using readily available reagents that are conducive to rapid iteration and optimization.

Methods

Synthesis of Cas9 RNPs. Cas9 RNP component synthesis and assembly was carried out based on published work. Cas9 was prepared by the UC Berkeley Macro Lab using a published protocol. Cas9 was stored and diluted in sterile-filtered Cas9 Buffer (20 mM HEPES pH 7.5, 150 mM KCl, 1 mM $MgCl_2$, 10% glycerol, 1 mM TCEP). TCEP was added to storage buffer only. sgRNA was synthesized by assembly PCR and in vitro-transcription. A T7 RNA polymerase substrate template was assembled by PCR from a variable 57-59 nt primer containing T7 promotor, variable sgRNA guide sequence, and the first 15 nt of the non-variable region of the sgRNA (T7FwdVar primers, 10 nM, FIG. 19), and an 83 nt primer containing the reverse complement of the invariant region of the sgRNA (T7RevLong, 10 nM), along with amplification primers (T7FwdAmp, T7RevAmp, 200 nM each). These primers anneal in the first cycle of PCR and are amplified in subsequent cycles. Phusion high-fidelity DNA polymerase was used for assembly (New England Biolabs, Inc.). Assembled template was used without purification as a substrate for in vitro transcription by T7 RNA polymerase using the HiScribe T7 High Yield RNA Synthesis kit (New England Biolabs, Inc.).

Resulting transcriptions reactions were treated with DNAse I, and RNA was purified either by treatment with a 5× volume of homemade SPRI beads (comparable to Beckman-Coulter AMPure beads) or the Qiagen RNeasy purification kit, and elution in DEPC-treated water. sgRNA concentrations were determined by fluorescence using the Qubit dsDNA HS assay kit (Life Technologies, Inc). Cas9 RNP was assembled immediately prior to electroporation of target cells (see below). To electroporate a 20 μL cell suspension (150,000-200,000 cells) with Cas9 RNP, a 5 μL solution containing a 1.2-1.3× molar excess of sgRNA in Cas9 buffer was prepared. A 5 μL solution containing 75-200 pmol purified Cas9 in Cas9 buffer was prepared and added to the sgRNA solution slowly over ~30 seconds, and incubated at room temperature for >5 minutes prior to mixing with target cells.

Editing HBB in K562 cells. K562 cells were obtained from the UC Berkeley Tissue Culture facilit, and cultured in IMDM with 10% FCS, penicillin-streptomycin (100 units/mL and 100 μg/mL), plus 2 mM GlutaMax. K562 cells were edited by electroporation using the Lonza 4d nucleofector and manufacturer's protocols (Lonza, Inc.). For each electroporation, 150,000-200,000 late log-phase K562 cells were pelleted (100×g, 5 minutes) and re-suspended in 20 μL Lonza SF solution. 20 μL cells, 10 μL Cas9 RNP containing the desired guide (see above, and FIG. 19), and 1 μL 100 μM ssDNA template carrying the desired edit at the SCD SNP were mixed and electroporated using the recommended protocol for K562 cells. After electroporation, K562 cells were incubated for 10 minutes in the cuvette, transferred to 1 mL of the above medium, and cultured for 48-72 h prior to genomic DNA extraction and genotyping.

Editing HBB in primary human CD34+ HSCs. Cryopreserved WT human mobilized peripheral blood $CD34^+$ HSPCs were purchased from Allcells, Inc. SCD $CD34^+$ HSPCs were prepared by Allcells Inc. from whole blood discarded during exchange transfusion of SCD patients at Benioff Children's Hospital Oakland, and cryopreserved. To edit HSCs, ~1 million HSPCs were thawed and cultured in StemSpan SFEM medium supplemented with StemSpan CC110 cocktail (StemCell Technologies) for 24 h prior to electroporation with Cas9 RNP. To electroporate HSPCs, 100,000-200,000 were pelleted (200×g, 10 minutes) and resuspended in 20 μL Lonza P3 solution, and mixed with 10 μL Cas9 RNP and 1 μL 100 μM ssDNA template programming the desired edit. This mixture was electroporated using the Lonza 4d nucleofector and either of two protocols ("1": D0100, "2": ER100). Electroporated cells were recovered in the cuvette with 200 μL StemSpan SFEM/CC110 for 10-15 minutes and transferred to culture in 1 mL StemSpan SFEM/CC110 for 48 hours post-electroporation. Half of the cells were removed for genotyping ("un-expanded HSPCs") while the remaining cells were transferred to erythroid expansion media (StemSpan SFEM II with StemSpan Erythroid Expansion supplement, [StemCell Technologies]) for 5 additional days prior to genotyping of expanded cells. To determine the zygosity of edits in HSPCs (FIG. 19), a culture of edited HSPCs (2 days after electroporation) in SFEM/CC110 was diluted to 10 cells/mL in SFEM with erythroid expansion media, and 100 μL per well was plated into 96-well plates. Clones were grown for 14 days, then 96 clones were pelleted and their genomic DNA extracted for genotyping by NGS.

Editing HBB with newly-developed Cas9 Variants in $CD34^+$ HSPCs. Plasmids encoding Cas9 variants HF1 and espCas91.1 were generated from the previously-published wild-type Cas9 construct, and expressed and purified from *E. coli* using an identical protocol by the UC Berkeley Macro Lab. HSPCs were prepared and edited essentially identically as with wild-type Cas9: 75 pmol Cas9 variant complexed with guide G10 was delivered to 150,000 CD34+ HSPCs with no HDR donor. Edited HSPCs were cultured for 5 days in expansion conditions prior to genomic DNA extraction and subsequent analysis of indel formation at selected targets by NGS.

Editing HSPCs prior to injection in NSG mice. For each mouse, 750,000-1,000,000 CD34+ HSPCs were edited. Editing was performed using a scaled-up reaction volume from in vitro experiments above. 750,000-1,000,000 HSPCs were thawed and recovered for 24 h prior to editing. Both stimulated and unstimulated conditions used StemSpan SFEM medium supplemented with StemSpan CC110 cocktail, stimulation was for 3 days while unstimulated was as above. Prior to editing, HSPCs were pelleted and resuspended in 100 μL P3. 500 pmol Cas9 RNP was prepared in 50 μL Cas9 buffer. RNP, cells, and 5 μL T88-107 100 μM donor template were mixed in a large-sized cuvette and electroporated using the Lonza 4d Nucleofector and protocol "2" (ER100). Cells were recovered by addition of 400 μL StemSpan SFEM/CC110 to the cuvette, prior to culture in recovery media for 24 hours at a density <1 million cells/mL. For the first and third mouse experiment (2 mice and 3 mice respectively), cells were cultured in SFEM/CC110 for 1 day prior to editing. For the second experiment (2 mice), cells were cultured for 3 days prior to editing.

Xenografting of human CD34+ HSPCs into NSG mice. NSG mice (JAX) were maintained in clean conditions. 7 week old female mice were subjected to 2.5 Gy X-irradiation 4 hours prior to tail vein injection of edited cells under isoflurane anesthesia. At 5 weeks and 8 weeks after injection, 200 μl blood was obtained from the submandibular vein under isoflurane anesthesia. 16 weeks after injection, mice were euthanized, and bone marrow and spleen were recovered for analysis.

Flow cytometry. Cells were prepared from peripheral blood, bone marrow, or spleen of NSG mice by standard methods, stained with antibodies to the indicated cell surface markers, and analyzed on a BD FACS Fortessa flow cytometer. Flow cytometry data was analyzed using the FlowJo software package. For genotyping of the sorted pools, mouse bone marrow sorted by FACS for the indicated cell surface marker. Sorted cells were pelleted and genotyped by NGS as described above. The following antibodies were used, all from BD Pharmigen: APC Rat anti-Mouse CD45, (561018, clone 30-F11), FITC Mouse anti-Human CD45 (555482, clone HI30), V450 Mouse anti-Human CD45 (560368, clone HI30), BV421 Mouse anti-Human CD3 (563797 clone SK7), BV421 Mouse anti-Human CD56 (562752, clone NCAM16.2), FITC Mouse anti-Human CD19 (340409, clone SJ25C1), FITC Mouse anti-Human CD33 (561818, clone HIM3-4), BV421 Mouse anti-Human CD34 (562577, clone 581).

Differentiation of HSCs into erythroblasts. After electroporation, cells were recovered and placed in StemSpan SFEM/CC110 for 24 hours. The cells were then transferred to StemSpan SFEM II with StemSpan Erythroid Expansion supplement and grown for 7 days with maintenance of optimal density (200,000-1,000,000 cells/mL). The resulting erythroid progenitors were transferred to StemSpan SFEM II with 3 U/ml erythropoietin (Life Technologies), 3% normal human AB serum (Sigma), and 1 μM mifepristone (Sigma). They were then cultured for a further 5 days with daily monitoring of cell morphology after Wright-Giemsa staining; at the conclusion the majority of the cells were enucleated. Cells were then lysed in hemolysate Reagent (Helena Laboratories) for preparation of hemoglobin for HPLC, or RNA extracted with the Direct-zol RNA Kit (Zymo Research).

Genotyping of edited cells. Pools of edited cells (K562 cells, CD34+ HSPCs, and nucleated cells from mouse blood) were lysed and their genomic DNA extracted using QuickExtract solution (Epicentre Inc.) to a final concentration of ~5,000 haploid genomes/μL. A 286 bp region around the SCD SNP and Cas9 cut site was amplified by PCR using Q5 DNA polymerase (New England Biolabs, Inc), and primers 1F and 1R (see FIG. 19). NHEJ-mediated indel formation within each pool was estimated by T7 endonuclease digestion using manufacturer's protocols (New England Biolabs, Inc). HDR-mediated editing was assessed by restriction digest with either SfcI (for WT→SCD edits) or Hpy188III (for SCD→WT edits). For analysis of editing by next-generation sequencing (NGS), a second, initial PCR products were cleaned with SPRI beads (1.8×), followed by amplification of 20-50 ng product in a second 6-8 cycle PCR using primers 4F and 1R, generating amplicons of an appropriate length for NGS, prior to Illumina TruSeq adaptor ligation and purification (Bioo Scientific DNAseq kit or Illumina TruSeq Nano HT kit). To avoid contamination of ssDNA donor sequence, 1F and 1R amplify outside thegenomic region matching donor, and 4F does not anneal to the ssDNA donor. Libraries from 12-96 pools of edited cells were pooled and run on a single MiSeq lane, using a paired-end 150 cycle read. HDR-mediated editing of the SCD SNP was also assessed by droplet digital PCR (ddPCR, QX200, Bio-Rad Laboratories, Inc.). ddPCR assays (lx assay: 900 nM primers, and 250 nM each probe) used TaqMan probes specific for unedited and HDR-edited alleles, with one primer positioned outside of the template matching region of HBB to prevent amplification of donor template. Assays were run using ddPCR supermix for probes (no dUTP) with the following thermal cycling protocol: 1) 95° C. 10 min; 2), 94° C. 30 s; 3), 55° C. 1 min; 4), 72° C. 2 min, 5) repeat steps 2-4 39 times; 5), 98° C. 10 min with all the steps ramped by 2° C./s.

NGS Data analysis. 20 million MiSeq reads were demultiplexed and analyzed using a custom analysis workflow written in Python. Each sample contained >75,000 reads, generally much more. For each sample, reads were called as "indel", "HDR", or "unedited". Any read containing an indel within a window of 12-16 bases around the predicted cut site was called as "indel", and remaining reads were called as "unedited" or "HDR" based whether they matched either the unedited sequence or the ssDNA donor sequence at the SCD SNP. To assess incorporation of HBD coding sequence into HBB, four single-nucleotide differences between HBB and HBD were used. If all four HBD differences were found, that allele was called as HBD. Indel alleles were excluded from this analysis.

HPLC analysis of edited SCD HSPCs. HPLC analysis was performed as previously described. Briefly, edited SCD HSPCs differentiated into erythroblasts were harvested and lysed in Hemolysate reagent (Helena Laboratories). Cell lysates were characterized by HPLC (Infinity 1260, Agilent) using a weak cation-exchange column (PolyCAT A, PolyLC, Inc.,). Analysis and peak integration was performed using OpenLAB CDS Chemstation software. FASC Reference Material (Trinity Biotech) was used to define the elution time of common hemoglobins (HbF, HbA, HbS, and HbA2).

RNA-seq analysis of edited SCD HSPCs. Total RNA from SCD erythroblasts (~5×10$^6$, differentiated in vitro as described above) was isolated with the Direct-zol RNA Kit (Zymo Research). RNA integrity was checked on an Agilent Bioanalyzer; cDNA was synthesized from this RNA following the Smart-seq2 method, and fragmented with the Covaris apparatus. From the Covaris fragments, indexed—libraries were constructed with the ThruPlex-FD prep kit (Rubicon Genomics) and sequenced on an Illumina HiSeq 2500 sequencer for 100 cycles (single read) at the Berkeley GSL. Resulting RNA-seq reads for each sample were quantified against version 80 of the human Ensembl annotation using the program kallisto with default parameters, yielding the relative abundance of each mRNA in transcripts-per-million, which was then normalized for comparison between samples.

Analysis of indel formation in cancer-associated genes. To look for indel formation at cancer-associated genes in edited cells, large pools of K562 cells and HSPCs were edited with the trG10 (1000 pmol RNP, 1 million cells) as above, and cultured for 3 days (K562 cells) or 5 days (HSPCs, in SFEM/CC110). Genomic DNA was purified from these cells and untreated cells using the Qiagen Blood and Tissue DNA Extraction Kit (4 genomic DNA samples). Cancer-associated exons and SNPs were enriched and prepared for Illumina sequencing using the Illumina TruSight Cancer capture kit, and manufacturer's instruction, and sequencing on an Illumina HiSeq 4000 sequencer, 2×150 paired-end read. Resulting reads were analyzed for indel mutations compared to reference (human genome hg19) sequence using the MuTect2 algorithm. Indels in either sample that passed filters for sequencing errors and significance are listed in FIG. 20.

FIG. 20. Indel mutations at cancer-associated genes in K562 cells and HSPCs edited with the trG10 RNP, compared to unedited cells. Cancer-associated genes were captured from genomic DNA using the Illumina TruSight Cancer panel and mutations were detected using the open source Mutect2 algorithm (see methods).

Detection of Translocation Events by over-amplification PCR. Genomic DNA extracts of K562 cells and HSPCs edited with the trG10 RNP were amplified for 35 cycles using primers for the on- and off-target editing sites indicated. All four combinations of primers for each site (two on- and two off-target) were used, and the products were visualized on a 2% agarose gel. The predicted translocation amplicon lengths were estimated from the predicted cut sites.

TABLE 2

Oligonucleotides used in this study.

| Type | Name | Sequence | SEQ ID NO: |
|---|---|---|---|
| Amplification of SCD SNP region in human HBB | 1F | gggcagagccatctattgctta | 1136 |
| | 1R | tgggaaaatagaccaataggcagag | 1137 |
| | 4F | actgtgttcactagcaacctcaa | 1138 |

TABLE 2-continued

Oligonucleotides used in this study.

| Type | Name | Sequence | SEQ ID NO: |
|---|---|---|---|
| Assembly of T7 Polymerase Substrates for sgRNA synthesis by in vitro transcription (UPPERCASE = guide) | FwdVar-G3 | ggatcctaatacgactcactatagCAGACTTCTCCACAGGAGTCgttttagagctagaa | 1139 |
| | FwdVar-trG3 | ggatcctaatacgactcactataGACTTCTCCACAGGAGTCgttttagagctagaa | 1140 |
| | FwdVar-G5 | ggatcctaatacgactcactatagCATGGTGCACCTGACTCCTGgttttagagctagaa | 1141 |
| | FwdVar-G7 | ggatcctaatacgactcactataGTGTGCCGTTACTGCCCTGgttttagagctagaa | 1142 |
| | FwdVar-G10 | ggatcctaatacgactcactatagCTTGCCCCACAGGGCAGTAAgttttagagctagaa | 1143 |
| | FwdVar-trG10 | ggatcctaatacgactcactatagTGCCCCACAGGGCAGTAAgttttagagctagaa | 1144 |
| | FwdVar-G11 | ggatcctaatacgactcactatagCGTTACTGCCCTGTGGGGCAgttttagagctagaa | 1145 |
| | FwdVar-trG11 | ggatcctaatacgactcactataGTTACTGCCCTGTGGGGCAgttttagagctagaa | 1146 |
| | FwdVar-G17 | ggatcctaatacgactcactatagCGTGGATGAAGTTGGTGGTGgttttagagctagaa | 1147 |
| | FwdVar-G18 | ggatcctaatacgactcactatagTGAAGTTGGTGGTGAGGCCCgttttagagctagaa | 1148 |
| | T7RevLong | AAAAAAGCACCGACTCGGTGCCACTTTTTCAAGTTGATAACGGACTAGCCTTATTTTAACTTGCTATTTCTAGCTCTAAAAC | 1149 |
| | T7FwdAmp | GGATCCTAATACGACTCACTATAG | 1150 |
| | T7RevAmp | AAAAAAGCACCGACTCGG | 1151 |
| Primers and Probes for ddPCR analysis | ddPCR forward | CATAAAAGTCAGGGCAGAG | 1152 |
| | ddPCR reverse | GTCTCCTTAAACCTGTCTTG | 1153 |
| | WT -> SCD HDR probe | FAM-CTCCTgtaGAGAAGTCTGC-Quencher | 1154 |
| | WT -> SCD unedited probe | HEX-TGACTCCTgagGAGAAGT-Quencher | 1155 |
| | SCD -> WT HDR probe | FAM-CTCCTgaaGAGAAGTCTGC-Quencher | 1156 |
| | SCD -> WT unedited probe | HEX-CCTgtgGAGAAGTCTGC-Quencher | 1157 |
| ddDNA donor templates for editing WT to SCD (Val7[gta] codon is lowercase) | T1: 195 bp template (FIG. 13) | TACATTTGCTTCTGACACAACTGTGTTCACTAGCAACCTCAAACAGACACCATGGTGCATCTGACTCCTgtaGAGAAGTCTGCGGTTACTGCCCTGTGGGGCAAAGTGAACGTGGATGAAGTTGGTGGTGAAGCCCTCGGCAGGTTGGTATCAAGGTTACAAGACAGGTTTAAGGAGACCAATAGAAACTGGGCA | 1158 |
| | T2 (T88-107): 195 bp template (FIG. 13) | TACATTTGCTTCTGACACAACTGTGTTCACTAGCAACCTCAAACAGACACCATGGTGCACCTGACTCCTgtaGAGAAGTCTGC**G**GTTACTGCCCTGTGGGGCAAGGTGAACGTGGATGAAGTTGGTGGTGAGGCCCTGGGCAGGTTGGTATCAAGGTTACAAGACAGGTTTAAGGAGACCAATAGAAACTGGGCA | 1159 |
| | T2p: 195 bp template (FIG. 13) “*^*” indicates phosphorothioate protection | T^A^C^ATTTGCTTCTGACACAACTGTGTTCACTAGCAACCTCAAACAGACACCATGGTGCACCTGACTCCTgtaGAGAAGTCTGCGGTTACTGCCCTGTGGGCAAGGTGAACGTGGATGAAGTTGGTGGTGAGGCCCTGGGCAGGTTGGTATCAAGGTTACAAGACAGGTTTAAGGAGACCAATAGAAACTGG^G^C^A | 1160 |
| | T84-67 | TTTGCTTCTGACACAACTGTGTTCACTAGCAACCTCAAACAGACACCATGGTGCACCTGACTCCTgtaGAGAAGTCTGCGGTTACTGCCCTGTGGGGCAAGGTGAACGTGGATGAAGTTGGTGGTGAGGCCCTGGGCAGGTTGGTATCAAG | 1161 |

TABLE 2-continued

Oligonucleotides used in this study.

| Type | Name | Sequence | SEQ ID NO: |
|---|---|---|---|
| | T84-37 | TTTGCTTCTGACACAACTGTGTTCA CTAGCAACCTCAAACAGACACCAT GGTGCACCTGACTCCTgtaGAGAAGT CTGCGGTTACTGCCCTGTGGGGCAA GGTGAACGTGGATGAAGTTGG | 1162 |
| | T84-27 | TTTGCTTCTGACACAACTGTGTTCA CTAGCAACCTCAAACAGACACCAT GGTGCACCTGACTCCTgtaGAGAAGT CTGCGGTTACTGCCCTGTGGGGCAA GGTGAACGTGG | 1163 |
| | T84-17 | TTTGCTTCTGACACAACTGTGTTCA CTAGCAACCTCAAACAGACACCAT GGTGCACCTGACTCCTgtaGAGAAGT CTGCGGTTACTGCCCTGTGGGGCAA G | 1164 |
| | T111-57 | TCAGGGCAGAGCCATCTATTGCTTA CATTTGCTTCTGACACAACTGTGTT CACTAGCAACCTCAAACAGACACC ATGGTGCACCTGACTCCTgtaGAGAA GTCTGCGGTTACTGCCCTGTGGGGC AAGGTGAACGTGGATGAAGTTGGT GGTGAGGCCCTGGGCAGGT | 1165 |
| | T111-47 | TCAGGGCAGAGCCATCTATTGCTTA CATTTGCTTCTGACACAACTGTGTT CACTAGCAACCTCAAACAGACACC ATGGTGCACCTGACTCCTgtaGAGAA GTCTGCGGTTACTGCCCTGTGGGGC AAGGTGAACGTGGATGAAGTTGGT GGTGAGGCC | 1166 |
| | T111-37 | TCAGGGCAGAGCCATCTATTGCTTA CATTTGCTTCTGACACAACTGTGTT CACTAGCAACCTCAAACAGACACC ATGGTGCACCTGACTCCTgtaGAGAA GTCTGCGGTTACTGCCCTGTGGGGC AAGGTGAACGTGGATGAAGTTGG | 1167 |
| | T111-27 | TCAGGGCAGAGCCATCTATTGCTTA CATTTGCTTCTGACACAACTGTGTT CACTAGCAACCTCAAACAGACACC ATGGTGCACCTGACTCCTgtaGAGAA GTCTGCGGTTACTGCCCTGTGGGGC AAGGTGAACGTGG | 1168 |
| | T111-17 | TCAGGGCAGAGCCATCTATTGCTTA CATTTGCTTCTGACACAACTGTGTT CACTAGCAACCTCAAACAGACACC ATGGTGCACCTGACTCCTgtaGAGAA GTCTGCGGTTACTGCCCTGTGGGGC AAG | 1169 |
| ssDNA donor templates for editing WT to SCD (Glu7[gaa] codon is lowercase) | T88-107S (similar to T2, edits WT-to-SCD) | TACATTTGCTTCTGACACAACTGTG TTCACTAGCAACCTCAAACAGACA CCATGGTGCACCTGACTCCTgaaGAG AAGTCTGCGGTTACTGCCCTGTGGG GCAAGGTGAACGTGGATGAAGTTG GTGGTGAGGCCCTGGGCAGGTTGG TATCAAGGTTACAAGACAGGTTTA AGGAGACCAATAGAAACTGGGCA | 1170 |
| | T111-57S | TCAGGGCAGAGCCATCTATTGCTTA CATTTGCTTCTGACACAACTGTGTT CACTAGCAACCTCAAACAGACACC ATGGTGCACCTGACTCCTgaaGAGA AGTCTGCGGTTACTGCCCTGTGGGG CAAGGTGAACGTGGATGAAGTTGG TGGTGAGGCCCTGGGCAGGT | 1171 |
| | T111-37S | TCAGGGCAGAGCCATCTATTGCTTA CATTTGCTTCTGACACAACTGTGTT CACTAGCAACCTCAAACAGACACC ATGGTGCACCTGACTCCTgaaGAGA AGTCTGCGGTTACTGCCCTGTGGGG CAAGGTGAACGTGGATGAAGTTGG | 1172 |

TABLE 2-continued

Oligonucleotides used in this study.

| Type | Name | Sequence | SEQ ID NO: |
|---|---|---|---|
| | T111-27S | TCAGGGCAGAGCCATCTATTGCTTA CATTTGCTTCTGACACAACTGTGTT CACTAGCAACCTCAAACAGACACC ATGGTGCACCTGACTCCTgaaGAGA AGTCTGCGGTTACTGCCCTGTGGGG CAAGGTGAACGTGG | 1173 |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11427837B2). An electronic copy of the "Sequence Listing" will also be available from the USPTO upon request and payment of the fee set forth in 37 CFR 1.19(b)(3).

What is claimed is:

1. A method of editing a genomic DNA of a eukaryotic cell, the method comprising introducing into the eukaryotic cell a composition comprising:

(a) a genome targeting composition comprising a genome editing endonuclease, or a nucleic acid encoding the genome editing endonuclease, wherein the genome editing endonuclease cleaves within a desired target sequence of the genomic DNA of the cell; and (b) a linear non-homologous single stranded DNA composition comprising linear DNA in an amount effective to enhance the frequency of insertions and/or deletions (indels) within the genomic DNA, wherein the method results in modification of the genomic DNA.

2. The method according to claim 1, wherein the modification of the genomic DNA is an insertion of sequence into the genomic DNA and/or a deletion of sequence from the genomic DNA.

3. The method according to claim 1, wherein the genome targeting composition comprises:

a) a zinc finger nuclease or a TAL-effector DNA binding domain-nuclease fusion protein (TALEN);

b) a nucleic acid encoding a zinc finger nuclease or a TALEN;

c) a ribonucleoprotein (RNP) complex comprising a class 2 CRISPR/Cas endonuclease complexed with a corresponding CRISPR/Cas guide RNA that hybridizes to a target sequence within the genomic DNA of the cell; or d) a nucleic acid encoding a class 2 CRISPR/Cas endonuclease, and a corresponding CRISPR/Cas guide RNA, or a nucleic acid encoding the corresponding CRISPR/Cas guide RNA, wherein the CRISPR/Cas guide RNA hybridizes to a target sequence within the genomic DNA of the cell.

4. The method according to claim 3, wherein the class 2 CRISPR/Cas endonuclease is a Cas9 polypeptide and the corresponding CRISPR/Cas guide RNA is a Cas9 guide RNA.

5. The method according to claim 3, wherein the class 2 CRISPR/Cas endonuclease is a Cpf1 polypeptide, a C2c1 polypeptide, a C2c3 polypeptide, or a C2c2 polypeptide.

6. The method according to claim 1, wherein the linearized non-homologous single stranded DNA composition is a homogenous DNA composition.

7. The method according to claim 1, wherein the linearized non-homologous single stranded DNA composition is a heterogeneous DNA composition.

8. A method of editing genomic DNA of a eukaryotic cell, the method comprising introducing into the eukaryotic cell a composition comprising:

(a) a linear non-homologous single stranded DNA composition comprising linear DNA in an amount effective to enhance frequency of insertions and/or deletions (indels) within the genomic DNA; and (b) a ribonucleoprotein (RNP) complex comprising a class 2 CRISPR/Cas endonuclease complexed with a corresponding CRISPR/Cas guide RNA that hybridizes to a target sequence within the genomic DNA of the cell, wherein the class 2 CRISPR/Cas endonuclease cleaves the genomic DNA, resulting in editing of the genomic DNA.

9. The method according to claim 8, wherein the class 2 CRISPR/Cas endonuclease is a Cas9 polypeptide and the corresponding CRISPR/Cas guide RNA is a Cas9 guide RNA.

10. The method according to claim 8, wherein the class 2 CRISPR/Cas endonuclease is a Cpf1 polypeptide, a C2c1 polypeptide, a C2c3 polypeptide, or a C2c2 polypeptide.

11. The method according to claim 8, wherein the linearized non-homologous single stranded DNA composition is a homogenous DNA composition.

12. The method according to claim 8, wherein said method results in a deletion of genomic DNA.

13. The method according to claim 8, wherein the linearized non-homologous single stranded DNA composition is a heterogenous DNA composition.

* * * * *

UNITED STATES PATENT AND TRADEMARK OFFICE

CERTIFICATE OF CORRECTION

PATENT NO. : 11,427,837 B2
APPLICATION NO. : 16/067750
DATED : August 30, 2022
INVENTOR(S) : Jacob Ellery Corn et al.

It is certified that error appears in the above-identified patent and that said Letters Patent is hereby corrected as shown below:

In the Specification

In Column 33, Line 20, please delete "Type Hs" and replace it with -- Type IIs --;

In Column 34, Line 53, please delete "Fold" and replace it with -- FokI --;

In Column 35, Line 26, please delete "Fold" and replace it with -- FokI --; and In Column 69, Line 42, please delete "U205" and replace it with -- U20S --.

Signed and Sealed this
Seventh Day of February, 2023

Katherine Kelly Vidal

Katherine Kelly Vidal
*Director of the United States Patent and Trademark Office*